US012655224B2

(12) United States Patent
Gunzelmann et al.

(10) Patent No.: US 12,655,224 B2
(45) Date of Patent: Jun. 16, 2026

(54) COMPOSITIONS OF IL-1R1 ANTIBODIES AND METHODS OF PRODUCING AND USING THE SAME

(71) Applicant: Kiniksa Pharmaceuticals, GmbH, Zug (CH)

(72) Inventors: Doug Gunzelmann, Lexington, MA (US); Shaun Grier, Lexington, MA (US); Jianwen Xu, Lexington, MA (US)

(73) Assignee: Kiniksa Pharmaceuticals, GmbH, Zug (CH)

(*) Notice: Subject to any disclaimer, the term of this patent is extended or adjusted under 35 U.S.C. 154(b) by 0 days.

(21) Appl. No.: 19/273,461

(22) Filed: Jul. 18, 2025

(65) Prior Publication Data

US 2025/0388686 A1     Dec. 25, 2025

Related U.S. Application Data

(63) Continuation of application No. 19/249,733, filed on Jun. 25, 2025.

(60) Provisional application No. 63/762,497, filed on Feb. 24, 2025, provisional application No. 63/663,761, filed on Jun. 25, 2024.

(51) Int. Cl.
| | |
|---|---|
| *C07K 16/28* | (2006.01) |
| *B01D 61/46* | (2006.01) |

(52) U.S. Cl.
CPC ........ *C07K 16/2866* (2013.01); *B01D 61/463* (2022.08); *C07K 2317/10* (2013.01); *C07K 2317/14* (2013.01); *C07K 2317/565* (2013.01)

(58) Field of Classification Search
CPC .... C07K 2317/56; C07K 16/24; C07K 16/28; C07K 2317/76; A61P 37/02
See application file for complete search history.

(56) References Cited

U.S. PATENT DOCUMENTS

| | | | |
|---|---|---|---|
| 7,438,910 | B2 | 10/2008 | Varnum et al. |
| 9,925,263 | B2 | 3/2018 | Larson et al. |
| 10,000,565 | B2 | 6/2018 | Basson et al. |
| 10,041,044 | B2 | 8/2018 | Walsh et al. |
| 10,517,933 | B2 | 12/2019 | Fatatis et al. |
| 10,646,569 | B2 | 5/2020 | Shenoy |
| 10,961,585 | B2 | 3/2021 | Hatchwell et al. |
| 11,385,238 | B2 | 7/2022 | Ren et al. |
| 11,504,431 | B2 | 11/2022 | Prausnitz et al. |
| 2003/0049255 | A1 | 3/2003 | Sims et al. |
| 2006/0171948 | A1 | 8/2006 | Weinstein et al. |
| 2007/0248597 | A1 | 10/2007 | Henley et al. |
| 2011/0014189 | A1 | 1/2011 | Soula et al. |
| 2013/0149312 | A1 | 6/2013 | Finch et al. |
| 2014/0199320 | A1 | 7/2014 | Jankovic et al. |
| 2014/0314746 | A1 | 10/2014 | Artlett et al. |
| 2016/0228371 | A1 | 8/2016 | Schultz et al. |
| 2018/0105589 | A1 | 4/2018 | Dillon et al. |
| 2019/0218614 | A1 | 7/2019 | Walsh et al. |
| 2020/0352857 | A1 | 11/2020 | Gu et al. |
| 2020/0355582 | A1 | 11/2020 | Wu |
| 2021/0041453 | A1 | 2/2021 | Benchaar et al. |
| 2021/0155701 | A1 | 5/2021 | Hoshino et al. |
| 2022/0089724 | A1 | 3/2022 | Peddareddigari |
| 2022/0137010 | A1 | 5/2022 | Wen |
| 2022/0137061 | A1 | 5/2022 | Wu et al. |
| 2022/0146413 | A1 | 5/2022 | Duff et al. |
| 2022/0187398 | A1 | 6/2022 | Hwang et al. |
| 2022/0211813 | A1 | 7/2022 | Soriano et al. |
| 2022/0260584 | A1 | 8/2022 | Bondarenko et al. |
| 2022/0356240 | A1 | 11/2022 | Saffitz |
| 2023/0035363 | A1 | 2/2023 | Xiang et al. |
| 2026/0022180 | A1 | 1/2026 | Gunzelmann et al. |

FOREIGN PATENT DOCUMENTS

| | | | |
|---|---|---|---|
| EP | 1712239 | A2 | 10/2006 |
| WO | 2004/022718 | A2 | 3/2004 |
| WO | 2008/030931 | A2 | 3/2008 |
| WO | 2009/036209 | A2 | 3/2009 |
| WO | 2010/052505 | A1 | 5/2010 |
| WO | 2013/045404 | A2 | 4/2013 |
| WO | 2013/049278 | A1 | 4/2013 |
| WO | 2014/129914 | A1 | 8/2014 |
| WO | 2015/038811 | A2 | 3/2015 |
| WO | 2015/063770 | A1 | 5/2015 |
| WO | 2015/083120 | A1 | 6/2015 |
| WO | 2015/195842 | A1 | 12/2015 |
| WO | 2018/064307 | A2 | 4/2018 |
| WO | 2018/206565 | A1 | 11/2018 |
| WO | 2019/067639 | A1 | 4/2019 |
| WO | 2022/061092 | A1 | 3/2022 |

(Continued)

OTHER PUBLICATIONS

Kisselev L., Structure, 2002, vol. 10: 8-9.*
Witkowski et al., Biochemistry 38:11643-11650, 1999.*
Whisstock et al., Quarterly Reviews of Biophysics 2003, vol. 36 (3): 307-340.*
Devos et al., Proteins: Structure, Function and Genetics, 2000, vol. 41: 98-107.*
Wypych et al. JBC , 2008, 283(23), pp. 16194-16205.*
Dada et al., Electrophoresis, 215, 36, pp. 2695-2702.*
Dillon et al., Structural and functional characterization of disulfide isoforms of the human IgG2 subclass. J Biol Chem. Jun. 6, 2008;283(23):16206-15.
Liu et al., Human IgG2 Antibody Disulfide Rearrangement in Vivo. The Journal of Biological Chemistry. Oct. 24, 2008;283(43):29266-29272.

(Continued)

*Primary Examiner* — Tekchand Saidha
*Assistant Examiner* — Mohammad Y Meah
(74) *Attorney, Agent, or Firm* — McCarter & English, LLP; Maria Laccotripe Zacharakis; Maneesh Gulati, Esq.

(57) ABSTRACT

The instant invention relates to compositions comprising a protein, e.g., an antibody, or antigen-binding portion thereof, e.g., an anti-IL-1R1 antibody or antigen binding portion thereof, and methods, e.g., cell culture and protein purification methods, for producing such compositions.

28 Claims, 13 Drawing Sheets

Specification includes a Sequence Listing.

(56) References Cited

FOREIGN PATENT DOCUMENTS

WO      2022/098595  A1      5/2022
WO      2022/167916  A1      8/2022

OTHER PUBLICATIONS

Joshi et al., Avoiding antibody aggregation during processing: establishing hold times. Biotechnol J. Sep. 2014;9(9):1195-205.
Strickley et al., A review of Formulations of Commercially Available Antibodies. J Pharm Sci. Jul. 2021;110(7):2590-2608.e56.
Wang et al., Antibody structure, instability, and formulation. J Pharm Sci. Jan. 2007;96(1):1-26.
Warne, Development of high concentration protein biopharmaceuticals: the use of platform approaches in formulation development. Eur J Pharm Biopharm. Jun. 2011;78(2):208-12.
International Search Report and Written Opinion for Application No. PCT/US2025/035283, dated Jan. 23, 2026, 15 pages.

* cited by examiner

| Lot | pI | icIEF | | |
|---|---|---|---|---|
| | | % Acidic | % Main | % Basic |
| 1 | 7.6 | 21.6 | 66.9 | 11.6 |
| 2 | 7.6 | 31.9 | 61.2 | 4.0 |
| 3 | 7.6 | 44.3 | 52.9 | 2.8 |

SEQUENCE LISTING

```
Sequence total quantity: 11
SEQ ID NO: 1              moltype = AA  length = 5
FEATURE                   Location/Qualifiers
source                    1..5
                          mol_type = protein
                          organism = synthetic construct
SEQUENCE: 1
FHWIA                                                        5

SEQ ID NO: 2              moltype = AA  length = 17
FEATURE                   Location/Qualifiers
```

-continued

```
source                    1..17
                          mol_type = protein
                          organism = synthetic construct
SEQUENCE: 2
IIHPGASDTR YSPSFQG                                                       17

SEQ ID NO: 3              moltype = AA  length = 9
FEATURE                   Location/Qualifiers
source                    1..9
                          mol_type = protein
                          organism = synthetic construct
SEQUENCE: 3
QRELDYFDY                                                                9

SEQ ID NO: 4              moltype = AA  length = 11
FEATURE                   Location/Qualifiers
source                    1..11
                          mol_type = protein
                          organism = synthetic construct
SEQUENCE: 4
RASQSIGSSL H                                                             11

SEQ ID NO: 5              moltype = AA  length = 7
FEATURE                   Location/Qualifiers
source                    1..7
                          mol_type = protein
                          organism = synthetic construct
SEQUENCE: 5
YASQSFS                                                                  7

SEQ ID NO: 6              moltype = AA  length = 9
FEATURE                   Location/Qualifiers
source                    1..9
                          mol_type = protein
                          organism = synthetic construct
SEQUENCE: 6
HQSSSLPLT                                                                9

SEQ ID NO: 7              moltype = AA  length = 118
FEATURE                   Location/Qualifiers
source                    1..118
                          mol_type = protein
                          organism = synthetic construct
SEQUENCE: 7
EVQLMQSGAE VKKPGESLKI SCKGSGYSFS FHWIAWVRQM PGKGLEWMGI IHPGASDTRY 60
SPSFQGQVTI SADNSNSATY LQWSSLKASD TAMYFCARQR ELDYFDYWGQ GTLVTVSS     118

SEQ ID NO: 8              moltype = AA  length = 107
FEATURE                   Location/Qualifiers
source                    1..107
                          mol_type = protein
                          organism = synthetic construct
SEQUENCE: 8
EIVLTQSPDF QSVTPKEKVT ITCRASQSIG SSLHWYQQKP DQSPKLLIKY ASQSFSGVPS 60
RFSGSGSGTD FTLTINSLEA EDAAAYYCHQ SSSLPLTFGG GTKVEIK             107

SEQ ID NO: 9              moltype = AA  length = 444
FEATURE                   Location/Qualifiers
source                    1..444
                          mol_type = protein
                          organism = synthetic construct
SEQUENCE: 9
EVQLMQSGAE VKKPGESLKI SCKGSGYSFS FHWIAWVRQM PGKGLEWMGI IHPGASDTRY 60
SPSFQGQVTI SADNSNSATY LQWSSLKASD TAMYFCARQR ELDYFDYWGQ GTLVTVSSAS 120
TKGPSVFPLA PCSRSTSEST AALGCLVKDY FPEPVTVSWN SGALTSGVHT FPAVLQSSGL 180
YSLSSVVTVP SSNFGTQTYT CNVDHKPSNT KVDKTVERKC CVECPPCPAP PVAGPSVFLF 240
PPKPKDTLMI SRTPEVTCVV VDVSHEDPEV QFNWYVDGVE VHNAKTKPRE EQFNSTFRVV 300
SVLTVVHQDW LNGKEYKCKV SNKGLPAPIE KTISKTKGQP REPQVYTLPP SREEMTKNQV 360
SLTCLVKGFY PSDIAVEWES NGQPENNYKT TPPMLDSDGS FFLYSKLTVD KSRWQQGNVF 420
SCSVMHEALH NHYTQKSLSL SPGK                                       444

SEQ ID NO: 10             moltype = AA  length = 214
FEATURE                   Location/Qualifiers
source                    1..214
                          mol_type = protein
                          organism = synthetic construct
SEQUENCE: 10
EIVLTQSPDF QSVTPKEKVT ITCRASQSIG SSLHWYQQKP DQSPKLLIKY ASQSFSGVPS 60
RFSGSGSGTD FTLTINSLEA EDAAAYYCHQ SSSLPLTFGG GTKVEIKRTV AAPSVFIFPP 120
```

-continued

```
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 11              moltype = AA  length = 569
FEATURE                    Location/Qualifiers
source                     1..569
                           mol_type = protein
                           organism = Homo sapiens
REGION                     1..569
                           note = NP_000868.1 interleukin-1 receptor type 1 isoform 1
                            precursor
SEQUENCE: 11
MKVLLRLICF IALLISSLEA DKCKEREEKI ILVSSANEID VRPCPLNPNE HKGTITWYKD  60
DSKTPVSTEQ ASRIHQHKEK LWFVPAKVED SGHYYCVVRN SSYCLRIKIS AKFVENEPNL  120
CYNAQAIFKQ KLPVAGDGGL VCPYMEFFKN ENNELPKLQW YKDCKPLLLD NIHFSGVKDR  180
LIVMNVAEKH RGNYTCHASY TYLGKQYPIT RVIEFITLEE NKPTRPVIVS PANETMEVDL  240
GSQIQLICNV TGQLSDIAYW KWNGSVIDED DPVLGEDYYS VENPANKRRS TLITVLNISE  300
IESRFYKHPF TCFAKNTHGI DAAYIQLIYP VTNFQKHMIG ICVTLTVIIV CSVFIYKIFK  360
IDIVLWYRDS CYDFLPIKAS DGKTYDAYIL YPKTVGEGST SDCDIFVFKV LPEVLEKQCG  420
YKLFIYGRDD YVGEDIVEVI NENVKKSRRL IIILVRETSG FSWLGGSSEE QIAMYNALVQ  480
DGIKVVLLEL EKIQDYEKMP ESIKFIKQKH GAIRWSGDFT QGPQSAKTRF WKNVRYHMPV  540
QRRSPSSKHQ LLSPATKEKL QREAHVPLG                                    569
```

1

COMPOSITIONS OF IL-1R1 ANTIBODIES AND METHODS OF PRODUCING AND USING THE SAME

RELATED APPLICATIONS

This application is a continuation application of U.S. patent application Ser. No. 19/249,733, filed on Jun. 25, 2025, which claims the benefit of priority to U.S. Provisional Application No. 63/663,761, filed on Jun. 25, 2024, and U.S. Provisional Application No. 63/762,497, filed on Feb. 24, 2025. The entire contents of each of the foregoing applications are incorporated hereby by reference.

SEQUENCE LISTING

This application contains a Sequence Listing which has been submitted electronically in XML format and is hereby incorporated by reference in its entirety. The XML copy, created on Jul. 17, 2025, is named 132261-00304.xml and is 12,211 bytes in size.

BACKGROUND OF THE INVENTION

Antibodies, such as monoclonal antibodies (mAbs), are an important class of therapeutic drugs in the pharmaceutical industry. Antibody therapeutics have been developed for treating many diseases such as cancer, inflammation and autoimmune disorders.

The production of monoclonal antibodies for pharmaceutical applications generally involves the use of upstream process technologies (e.g., cell culture) and downstream process technologies (e.g., protein purification). Typically, antibodies are produced as recombinant proteins in mammalian cell cultures to ensure proper folding and post-translational modification. Monoclonal antibodies produced from cell cultures need to be purified from host cell proteins and other impurities in order to be effectively utilized, for example, to improve the safety profile.

Proteins exhibiting varying levels of variants and impurities may be produced through the upstream and downstream process. Such protein variants and impurities include, but are not limited to, product-related substances, e.g., protein aggregates, fragments, or charged species, e.g., acidic or basic species; and/or process-related impurities, e.g., host cell proteins, nucleic acids, and residual media components.

SUMMARY OF THE INVENTION

The present disclosure is based on the identification and optimization of the upstream and downstream process technologies for production of antibodies or antigen-binding portions thereof, resulting in compositions having a consistently low level of variants and/or impurities, e.g., a consistently low level of product-related substances, e.g., product aggregates, or charged species, e.g., acidic species. Such variant and impurity-reduced compositions address the need for improved product characteristics, including, but not limited to, product stability, product safety and product efficacy.

Accordingly, in one aspect, the present invention provides a composition comprising an anti-IL-1R1 antibody, or antigen-binding portion thereof, wherein the composition comprises less than about 55%, e.g., about 54%, about 53%, about 52%, about 51%, about 50%, about 49%, about 48%, about 47%, about 46%, about 45%, about 44%, about 43%, about 42%, about 41%, about 40%, about 39%, about 38%, about 37%, about 36%, about 35%, about 34%, about 33%, about 32%, about 31%, about 30%, about 29%, about 28%, about 27%, about 26%, about 25%, about 24%, about 23%, about 22%, about 21%, about 20%, about 19%, about 18%, about 17%, about 16%, about 15%, about 14%, about 13%, about 12%, about 11%, or about 10% acidic species of the antibody.

In another aspect, the present invention provides a composition comprising an anti-IL-1R1 antibody, or antigen-binding portion thereof, wherein the composition comprises about 30-55%, about 31-55%, about 32-55%, about 33-55%, about 34-55%, about 35-55%, about 30-40%, about 31-40%, about 32-40%, about 33-40%, about 34-40%, about 35-40%, about 31-39%, about 31-38%, about 31-37%, about 31-36%, about 32-39%, about 32-38%, about 32-37%, about 32-36%, about 33-39%, about 33-38%, about 33-37%, about 33-36%, about 34-39%, about 34-38%, about 34-37%, or about 34-36% acidic species of the antibody. In some embodiments, the composition comprises about 30-55% acidic species. In some embodiments, the composition comprises about 34-36% acidic species.

In one aspect, the present invention provides a composition comprising an anti-IL-1R1 antibody, or antigen-binding portion thereof, wherein the composition comprises less than about 15%, e.g., about 14%, about 13%, about 12%, about 11%, about 10%, about 9%, about 8%, about 7%, about 6%, about 5%, about 4%, about 3%, about 2%, or about 1%, basic species of the antibody.

In another aspect, the present invention provides a composition comprising an anti-IL-1R1 antibody, or antigen-binding portion thereof, wherein the composition comprises about 1-5%, about 2-5%, about 2-4%, or about 1-4%, or about 1-5%, or about 1-6%, or about 1-7%, or about 1-8%, or about 1-9%, or about 1-10%, or about 1-11%, or about 1-12%, or about 1-13%, or about 1-14%, or about 1-15% basic species of the antibody. In some embodiments, the composition comprises about 1-15% basic species.

In one aspect, the present invention provides a composition comprising an anti-IL-1R1 antibody, or antigen-binding portion thereof, wherein the composition comprises more than about 40%, e.g., about 41%, about 42%, about 43%, about 44%, about 45%, about 46%, about 47%, about 48%, about 49%, about 50%, about 55%, about 60%, about 61%, about 62%, about 63%, about 64%, about 65%, about 66%, about 67%, about 68%, about 69%, about 70%, about 75%, about 80%, about 85%, about 90%, about 95% or about 99% main species of the antibody.

In another aspect, the present invention provides a composition comprising an anti-IL-1R1 antibody, or antigen-binding portion thereof, wherein the composition comprises about 40-70%, about 40-70%, about 40-65%, about 40-60%, about 40-55%, about 40-50%, about 55-75%, about 55-70%, about 60-70%, about 60-65%, or about 60-63% main species of the antibody. In some embodiments, the composition comprises about 60-63% main species.

In some embodiments, the composition comprises about 30-55% acidic species, about 1-15% basic species, and about 40-75% main species.

In some embodiments, the composition comprises about 30-40% acidic species, about 1-5% basic species, and about 55-75% main species.

In some embodiments, the composition comprises about 34-36% acidic species, about 1-5% basic species, and about 60-63% main species.

In one aspect, the present invention provides a composition comprising an anti-IL-1R1 antibody, or antigen-binding portion thereof, wherein the composition comprises an eluate fraction collected from a cation exchange chromatography resin, and wherein the eluate fraction comprises less than about 55%, e.g., about 54%, about 53%, about 52%, about 51%, about 50%, about 49%, about 48%, about 47%, about 46%, about 45%, about 44%, about 43%, about 42%, about 41%, about 40%, about 39%, about 38%, about 37%, about 36%, about 35%, about 34%, about 33%, about 32%, about 31%, about 30%, about 29%, about 28%, about 27%, about 26%, about 25%, about 24%, about 23%, about 22%, about 21%, about 20%, about 19%, about 18%, about 17%, about 16%, about 15%, about 14%, about 13%, about 12%, about 11%, or about 10% acidic species of the antibody.

In another aspect, the present invention provides a composition comprising an anti-IL-1R1 antibody, or antigen-binding portion thereof, wherein the composition comprises an eluate fraction collected from a cation exchange chromatography resin, and wherein the eluate fraction comprises about 30-55%, about 31-55%, about 32-55%, about 33-55%, about 34-55%, about 35-55%, about 30-40%, about 31-40%, about 32-40%, about 33-40%, about 34-40%, about 35-40%, about 31-39%, about 31-38%, about 31-37%, about 31-36%, about 32-39%, about 32-38%, about 32-37%, about 32-36%, about 33-39%, about 33-38%, about 33-37%, about 33-36%, about 34-39%, about 34-38%, about 34-37%, or about 34-36% acidic species of the antibody. In some embodiments, the eluate fraction comprises about 34-36% acidic species. In some embodiments, the eluate fraction comprises about 30-55% acidic species.

In one aspect, the present invention provides a composition comprising an anti-IL-1R1 antibody, or antigen-binding portion thereof, wherein the composition comprises an eluate fraction collected from a cation exchange chromatography resin, and wherein the eluate fraction comprises less than about 15%, e.g., about 14%, about 13%, about 12%, about 11%, about 10%, about 9%, about 8%, about 7%, about 6%, about 5%, about 4%, about 3%, about 2%, or about 1%, basic species of the antibody.

In another aspect, the present invention provides a composition comprising an anti-IL-1R1 antibody, or antigen-binding portion thereof, wherein the composition comprises an eluate fraction collected from a cation exchange chromatography resin, and wherein the eluate fraction comprises about 1-5%, about 2-5%, about 2-4%, or about 1-4%, or about 1-5%, or about 1-6%, or about 1-7%, or about 1-8%, or about 1-9%, or about 1-10%, or about 1-11%, or about 1-12%, or about 1-13%, or about 1-14%, or about 1-15% basic species of the antibody. In some embodiments, the eluate fraction comprises about 1-15% basic species.

In one aspect, the present invention provides a composition comprising an anti-IL-1R1 antibody, or antigen-binding portion thereof, wherein the composition comprises an eluate fraction collected from a cation exchange chromatography resin, and wherein the eluate fraction comprises more than about 40%, e.g., about 41%, about 42%, about 43%, about 44%, about 45%, about 46%, about 47%, about 48%, about 49%, about 50%, about 55%, about 60%, about 61%, about 62%, about 63%, about 64%, about 65%, about 66%, about 67%, about 68%, about 69%, about 70%, about 75%, about 80%, about 85%, about 90%, about 95% or about 99% main species of the antibody.

In another aspect, the present invention provides a composition comprising an anti-IL-1R1 antibody, or antigen-binding portion thereof, wherein the composition comprises an eluate fraction collected from a cation exchange chromatography resin, and wherein the eluate fraction comprises about 40-70%, about 40-70%, about 40-65%, about 40-60%, about 40-55%, about 40-50%, about 55-75%, about 55-70%, about 60-70%, about 60-65%, or about 60-63% main species of the antibody. In some embodiments, the eluate fraction comprises about 60-63% main species.

In some embodiments, the eluate fraction comprises about 30-40% acidic species, about 1-5% basic species, and about 55-75% main species. In some embodiments, the eluate fraction comprises about 34-36% acidic species, about 1-5% basic species, and about 60-63% main species. In some embodiments, the eluate fraction comprises about 30-55% acidic species, about 1-15% basic species, and about 40-75% main species.

In one aspect, the present invention provides a composition comprising an anti-IL-1R1 antibody, or antigen-binding portion thereof, wherein the composition comprises a flow-through fraction collected from an anion exchange chromatography resin, and wherein the flow-through fraction comprises less than about 55%, e.g., about 54%, about 53%, about 52%, about 51%, about 50%, about 49%, about 48%, about 47%, about 46%, about 45%, about 44%, about 43%, about 42%, about 41%, about 40%, about 39%, about 38%, about 37%, about 36%, about 35%, about 34%, about 33%, about 32%, about 31%, about 30%, about 29%, about 28%, about 27%, about 26%, about 25%, about 24%, about 23%, about 22%, about 21%, about 20%, about 19%, about 18%, about 17%, about 16%, about 15%, about 14%, about 13%, about 12%, about 11%, or about 10% acidic species of the antibody.

In another aspect, the present invention provides a composition comprising an anti-IL-1R1 antibody, or antigen-binding portion thereof, wherein the composition comprises a flow-through fraction collected from an anion exchange chromatography resin, and wherein the flow-through fraction comprises about 30-55%, about 31-55%, about 32-55%, about 33-55%, about 34-55%, about 35-55%, about 30-40%, about 31-40%, about 32-40%, about 33-40%, about 34-40%, about 35-40%, about 31-39%, about 31-38%, about 31-37%, about 31-36%, about 32-39%, about 32-38%, about 32-37%, about 32-36%, about 33-39%, about 33-38%, about 33-37%, about 33-36%, about 34-39%, about 34-38%, about 34-37%, or about 34-36% acidic species of the antibody. In some embodiments, the flow-through fraction comprises about 30-55% acidic species. In some embodiments, the flow-through fraction comprises about 34-36% acidic species.

In one aspect, the present invention provides a composition comprising an anti-IL-1R1 antibody, or antigen-binding portion thereof, wherein the composition comprises a flow-through fraction collected from an anion exchange chromatography resin, and wherein the flow-through fraction comprises less than about 15%, e.g., about 14%, about 13%, about 12%, about 11%, about 10%, about 9%, about 8%, about 7%, about 6%, about 5%, about 4%, about 3%, about 2%, or about 1%, basic species of the antibody.

In one aspect, the present invention provides a composition comprising an anti-IL-1R1 antibody, or antigen-binding portion thereof, wherein the composition comprises a flow-through fraction collected from an anion exchange chromatography resin, and wherein the flow-through fraction comprises about 1-5%, about 2-5%, about 2-4%, or about 1-4%, or about 1-5%, or about 1-6%, or about 1-7%, or about 1-8%, or about 1-9%, or about 1-10%, or about 1-11%, or about 1-12%, or about 1-13%, or about 1-14%, or about 1-15% basic species of the antibody. In some embodiments, the flow-through fraction comprises about 1-15% basic species.

In one aspect, the present invention provides a composition comprising an anti-IL-1R1 antibody, or antigen-binding portion thereof, wherein the composition comprises a flow-through fraction collected from an anion exchange chromatography resin, and wherein the flow-through fraction comprises more than about 40%, e.g., about 41%, about 42%, about 43%, about 44%, about 45%, about 46%, about 47%, about 48%, about 49%, about 50%, about 55%, about 60%, about 61%, about 62%, about 63%, about 64%, about 65%, about 66%, about 67%, about 68%, about 69%, about 70%, about 75%, about 80%, about 85%, about 90%, about 95% or about 99% main species of the antibody.

In one aspect, the present invention provides a composition comprising an anti-IL-1R1 antibody, or antigen-binding portion thereof, wherein the composition comprises a flow-through fraction collected from an anion exchange chromatography resin, and wherein the flow-through fraction comprises about 40-70%, about 40-70%, about 40-65%, about 40-60%, about 40-55%, about 40-50%, about 55-75%, about 55-70%, about 60-70%, about 60-65%, or about 60-63% main species of the antibody. In some embodiments, the flow-through fraction comprises about 60-63% main species.

In some embodiments, the flow-through fraction comprises about 30-40% acidic species, about 1-5% basic species, and about 55-75% main species. In some embodiments, the flow-through fraction comprises about 34-36% acidic species, about 1-5% basic species, and about 60-63% main species. In some embodiments, the flow-through fraction comprises about 30-55% acidic species, about 1-15% basic species, and about 40-75% main species.

In some embodiments, the anti-IL-1R1 antibody, or antigen-binding portion thereof, comprises a heavy chain variable region comprising a CDR1 having an amino acid sequence of SEQ ID NO:1, a CDR2 having an amino acid sequence of SEQ ID NO:2, and a CDR3 having an amino acid sequence of SEQ ID NO:3.

In some embodiments, the anti-IL-1R1 antibody, or antigen-binding portion thereof, comprises a light chain variable region comprising a CDR1 having an amino acid sequence of SEQ ID NO:4, a CDR2 having an amino acid sequence of SEQ ID NO:5, and a CDR3 having an amino acid sequence of SEQ ID NO:6.

In some embodiments, the anti-IL-1R1 antibody, or antigen-binding portion thereof, comprises a heavy chain variable region comprising an amino acid sequence of SEQ ID NO:7, and a light chain variable region comprising an amino acid sequence of SEQ ID NO:8.

In some embodiments, the anti-IL-1R1 antibody, or antigen-binding portion thereof, comprises a heavy chain comprising an amino acid sequence of SEQ ID NO:9, and a light chain comprising an amino acid sequence of SEQ ID NO:10.

In some embodiments, the anti-IL-1R1 antibody, or antigen-binding portion thereof, is KPL-387.

In some embodiments, the level of acidic species, the level of main species, or the level of basic species is determined by Imaging Capillary Isoelectric Focusing (iCIEF).

In one aspect, the present invention provides a method of producing a composition comprising an anti-IL-1R1 antibody, or antigen-binding portion thereof, having less than about 55% acidic species or between about 30-55% acidic species, the method comprising subjecting a sample comprising the anti-IL-1R1 antibody, or antigen-binding portion thereof, to a chromatography resin, wherein the chromatography resin is selected from a group consisting of a cation exchange chromatography resin and an anion exchange chromatography resin, or combinations thereof, thereby producing the composition comprising the anti-IL-1R1 antibody, or antigen-binding portion thereof, having less than about 55% acidic species or between about 30-55% acidic species.

In one aspect, the present invention provides a method of preventing the level of acidic species from exceeding about 55% in a composition comprising an anti-IL-1R1 antibody, or antigen-binding portion thereof, the method comprising subjecting a sample comprising the anti-IL-1R1 antibody, or antigen-binding portion thereof, to a chromatography resin or membrane, wherein the chromatography resin or membrane is selected from a group consisting of a cation exchange chromatography resin, an anion exchange chromatography resin, a cation exchange chromatography membrane, an anion exchange chromatography membrane, or combinations thereof, thereby preventing the level of acidic species from exceeding about 55% in the composition comprising the anti-IL-1R1 antibody, or antigen-binding portion thereof.

In some embodiments, the method prevents the level of acid species from exceeding about 55%, about 54%, about 53%, about 52%, about 51%, about 50%, about 49%, about 48%, about 47%, about 46%, about 45%, about 44%, about 43%, about 42%, about 41%, about 40%, about 39%, about 38%, about 37%, or about 36% in the composition.

In one aspect, the present invention provides a method of maintaining the level of acidic species at less than about 55% or at about 30-55% in a composition comprising an anti-IL-1R1 antibody, or antigen-binding portion thereof, the method comprising subjecting a sample comprising the anti-IL-1R1 antibody, or antigen-binding portion thereof, to a chromatography resin, wherein the chromatography resin is selected from a group consisting of a cation exchange chromatography resin and an anion exchange chromatography resin, or combinations thereof, thereby maintaining the level of acidic species at less than about 55% or at about 30-55% in the composition.

In some embodiments, the method further comprises maintaining the level of basic species at less than about 15%, or preventing the level of basic species from exceeding about 15%.

In some embodiments, the method further comprises maintaining the level of main species at about 40-75%, or preventing the level of main species from dropping below 40%.

In some embodiments, the anti-IL-1R1 antibody or antigen-binding portion thereof, comprises a heavy chain variable region comprising a CDR1 having an amino acid sequence of SEQ ID NO:1, a CDR2 having an amino acid sequence of SEQ ID NO:2, and a CDR3 having an amino acid sequence of SEQ ID NO:3.

In some embodiments, the anti-IL-1R1 antibody, or antigen-binding portion thereof, comprises a light chain variable region comprising a CDR1 having an amino acid sequence of SEQ ID NO:4, a CDR2 having an amino acid sequence of SEQ ID NO:5, and a CDR3 having an amino acid sequence of SEQ ID NO:6.

In some embodiments, the anti-IL-1R1 antibody, or antigen-binding portion thereof, comprises a heavy chain variable region comprising an amino acid sequence of SEQ ID NO:7, and a light chain variable region comprising an amino acid sequence of SEQ ID NO:8.

In some embodiments, the anti-IL-1R1 antibody, or antigen-binding portion thereof, comprises a heavy chain comprising an amino acid sequence of SEQ ID NO:9, and a light chain comprising an amino acid sequence of SEQ ID NO:10.

In some embodiments, the anti-IL-1R1 antibody, or antigen-binding portion thereof, is KPL-387.

In some embodiments, the sample is subject to a cation exchange chromatography resin.

In some embodiments, the cation exchange chromatography resin comprises a functional group selected from the group consisting of sulpfhydryl, sulfonate, sulfate, carboxymethyl, sulfoethyl, sulfopropyl, phosphate and sulfonate.

In some embodiments, the cation exchange chromatography resin is selected from the group consisting of POROS™ XS CEX, Capto™ S ImpAct, TOTOPEARL™ GigaGap CM 650M, and TOYOPEAL™ sulfate 650F.

In some embodiments, the cation exchange chromatography resin runs in bind-elute mode.

In some embodiments, an elution step of the cation exchange chromatography is carried out at a pH of greater than about 5.7, e.g., a pH of about 5.8, about 5.9, or about 6.0, or about 6.1.

In some embodiments, the elution step of the cation exchange chromatography is carried out at a pH of about 5.8-6.0. In some embodiments, the elution step of the cation exchange chromatography is carried out at a pH of about 5.8-6.1.

In one embodiment, a wash buffer and/or an elution buffer are added to achieve a pH of greater than 5.7, e.g., a pH of about 5.8, about 5.9, about 6.0, or about 6.1, during the elution step of the cation exchange chromatography.

In one embodiment, a wash buffer and/or an elution buffer are added to achieve a pH of about 5.8-6.0 during the elution step of the cation exchange chromatography. In one embodiment, a wash buffer and/or an elution buffer are added to achieve a pH of about 5.8-6.1 during the elution step of the cation exchange chromatography.

In some embodiments, the elution buffer comprises about 1-500 mM, about 10-250 mM, about 50-200 mM, about 70-150 mM, about 90-130 mM, about 110-130 mM, about 110-129 mM, about 110-125 mM, or about 110-120 mM sodium acetate. In some embodiments, the elution buffer comprises about 110-130 mM sodium acetate. In some embodiments, the elution buffer comprises about 110-129 mM. In some embodiments, the elution buffer comprises about 110-125 mM. In some embodiments, the elution buffer comprises about 110-120 mM.

In some embodiments, the elution buffer comprises a pH of about 5-7, about 5.5-6.5, about 5.8-6.2, about 5.8-6.1, or about 5.8-6.0. In some embodiments, the elution buffer comprises a pH of about 5.8-6.2. In some embodiments, the elution buffer comprises a pH of about 5.8-6.1.

In some embodiments, the elution buffer comprises about 110-130 mM sodium acetate, and has a pH of about 5.8-6.2. In some embodiments, the elution buffer comprises about 110-129 mM sodium acetate, and a pH of about 5.8-6.1. In some embodiments, the elution buffer comprises about 110-125 mM sodium acetate, and a pH of about 5.8-6.1. In some embodiments, the elution buffer comprises about 110-120 mM sodium acetate, and a pH of about 5.8-6.0. In some embodiments, the elution buffer comprises about 110-125 mM sodium acetate, and a pH of about 5.8-6.0.

In some embodiments, the elution buffer comprises about 120 mM sodium acetate, and has a pH of about 6.0. In some embodiments, the elution buffer comprises about 110 mM sodium acetate, and has a pH of about 5.8. In some embodiments, the elution buffer comprises about 130 mM sodium acetate, and has a pH of about 6.2.

In some embodiments, the wash buffer comprises about 1-500 mM, about 10-100 mM, about 10-30 mM, about 20-50 mM, or about 40-70 mM M sodium acetate.

In some embodiments, the wash buffer comprises a pH of about 4-7, about 4.5-6.5, about 4.8-6.2, about 4.8-5.8, about 5-6, or about 5.2-6.2.

In some embodiments, the wash buffer comprises about 20-50 mM sodium acetate and a pH of about 5-6. In some embodiments, the wash buffer comprises about 10-30 mM sodium acetate and a pH of about 4.8-5.8. In some embodiments, the wash buffer comprises about 40-70 mM sodium acetate and a pH of about 5.2-6.2.

In some embodiments, the sample is subject to an anion exchange chromatography resin.

In some embodiments, the anion exchange chromatography resin comprises a functional group selected from the group consisting of quaternary ammonium, quaternary polyethyleneimine, methacrylate, trimethylammoniummethyl, diethylaminoethyl, quaternary aminoethyl and quaternary amine.

In some embodiments, the anion exchange chromatography resin is selected from the group consisting of POROS™ HQ, Fractogel TMAE, and Q sepharose Fast Flow. In some embodiment, the anion exchange is a chromatograph membrane. In one embodiment the anion exchange chromatograph membrane is Sartobind Q.

In some embodiments, the anion exchange chromatography resin runs in flow-through mode.

In some embodiments, the sample is subject to a cation exchange chromatography resin followed by an anion exchange chromatography resin.

In some embodiments, prior to subjecting said sample to the cation exchange chromatography resin and the anion exchange chromatography resin, the sample is subjected to an affinity chromatography resin.

In some embodiments, the affinity chromatography resin is selected from the group consisting of MabSelect PrismA, Amsphere A3, Gore membrane, MabSelect SuRe LX, MabSelect SuRe™, MabSelect, MabSelect Xtra, Protein A Sepharose, ProSep HC, ProSep Ultra, ProSep Ultra Plus, and MapCapture.

In some embodiments, the composition comprises or the acidic species in the composition is maintained at less than about 55%, about 54%, about 53%, about 52%, about 51%, about 50%, about 49%, about 48%, about 47%, about 46%, about 45%, about 44%, about 43%, about 42%, about 41%, about 40%, about 39%, about 38%, about 37%, about 36%, about 35%, about 34%, about 33%, about 32%, about 31%, about 30%, about 29%, about 28%, about 27%, about 26%, about 25%, about 24%, about 23%, about 22%, about 21%, about 20%, about 19%, about 18%, about 17%, about 16%, about 15%, about 14%, about 13%, about 12%, about 11%, or about 10% acidic species.

In some embodiments, the composition comprises or the acidic species in the composition is maintained at less than about 55% acidic species.

In some embodiments, the composition comprises or the acidic species in the composition is maintained at about 30-55%, about 31-55%, about 32-55%, about 33-55%, about 34-55%, about 35-55%, about 31-40%, about 32-40%, about 33-40%, about 34-40%, about 35-40%, about 31-39%, about 31-38%, about 31-37%, about 31-36%, about 32-39%, about 32-38%, about 32-37%, about 32-36%, about 33-39%, about 33-38%, about 33-37%, about 33-36%, about 34-39%, about 34-38%, about 34-37%, or about 34-36% acidic species. In some embodiments, the composition comprises or the acidic species in the composition is maintained at about 34-36% acidic species. In some embodiments, the composition comprises or the acidic species in the composition is maintained at about 30-55% acidic species.

In some embodiments, the composition further comprises or the basic species in the composition is maintained at less than about 15%, e.g., about 14%, about 13%, about 12%, about 11%, about 10%, about 9%, about 8%, about 7%, about 6%, about 5%, about 4%, about 3%, about 2%, or about 1%, basic species.

In some embodiments, the composition further comprises or the basic species in the composition is maintained at about 1-5%, about 2-5%, about 2-4%, or about 1-4%, or about 1-5%, or about 1-6%, or about 1-7%, or about 1-8%, or about 1-9%, or about 1-10%, or about 1-11%, or about 1-12%, or about 1-13%, or about 1-14%, or about 1-15% basic species. In some embodiments, the composition further comprises or the basic species in the composition is maintained at about 1-15% basic species.

In some embodiments, the composition further comprises or the main species in the composition is maintained at more than about 40%, e.g., about 41%, about 42%, about 43%, about 44%, about 45%, about 46%, about 47%, about 48%, about 49%, about 50%, about 55%, about 60%, about 61%, about 62%, about 63%, about 64%, about 65%, about 66%, about 67%, about 68%, about 69%, about 70%, about 75%, about 80%, about 85%, about 90%, about 95% or about 99% main species of the antibody.

In some embodiments, the composition further comprises or the main species in the composition is maintained at about 40-70%, about 40-70%, about 40-65%, about 40-60%, about 40-55%, about 40-50%, about 55-75%, about 55-70%, about 60-70%, about 60-65%, or about 60-63% main species.

In some embodiments, the composition further comprises or the main species in the composition is maintained at about 60-63% main species.

In some embodiments, the composition comprises or the acidic, basic and main species in the composition are maintained at about 30-55% acidic species, about 1-15% basic species, and about 40-75% main species.

In some embodiments, the composition comprises or the acidic, basic and main species in the composition are maintained at about 30-40% acidic species, about 1-5% basic species, and about 55-75% main species.

In some embodiments, the composition comprises or the acidic, basic and main species in the composition are maintained at about 34-36% acidic species, about 1-5% basic species, and about 60-63% main species.

In some embodiments, the composition comprises about 40-80% isoform B, about 10-30% isoform A/B, and/or about 10-30% isoform A of the antibody.

In some embodiments, the composition comprises about 50-75% isoform B, about 15-25% isoform A/B, and/or about 10-25% isoform A of the antibody.

In some embodiments, the composition comprises about 45-60% isoform B, about 20-30% isoform A/B, and/or about 15-30% isoform A of the antibody.

In some embodiments, the method further comprises collecting an eluate fraction from the cation exchange chromatography resin using an elution buffer.

In some embodiments, the eluate fraction comprises or the acidic species in the eluate fraction is maintained at less than about 55%, about 54%, about 53%, about 52%, about 51%, about 50%, about 49%, about 48%, about 47%, about 46%, about 45%, about 44%, about 43%, about 42%, about 41%, about 40%, about 39%, about 38%, about 37%, about 36%, about 35%, about 34%, about 33%, about 32%, about 31%, about 30%, about 29%, about 28%, about 27%, about 26%, about 25%, about 24%, about 23%, about 22%, about 21%, about 20%, about 19%, about 18%, about 17%, about 16%, about 15%, about 14%, about 13%, about 12%, about 11%, or about 10% acidic species. In some embodiments, the eluate fraction comprises or the acidic species in the eluate fraction is maintained at less than about 55% acidic species.

In some embodiments, the eluate fraction comprises or the acidic species in the eluate fraction is maintained at about 30-55%, about 31-55%, about 32-55%, about 33-55%, about 34-55%, about 35-55%, about 31-40%, about 32-40%, about 33-40%, about 34-40%, about 35-40%, about 31-39%, about 31-38%, about 31-37%, about 31-36%, about 32-39%, about 32-38%, about 32-37%, about 32-36%, about 33-39%, about 33-38%, about 33-37%, about 33-36%, about 34-39%, about 34-38%, about 34-37%, or about 34-36% acidic species.

In some embodiments, the eluate fraction further comprises or the basic species in the eluate fraction is maintained at less than about 15%, e.g., about 14%, about 13%, about 12%, about 11%, about 10%, about 9%, about 8%, about 7%, about 6%, about 5%, about 4%, about 3%, about 2%, or about 1%, basic species. In some embodiments, the eluate fraction further comprises or the basic species in the eluate fraction is maintained at about 1-5%, about 2-5%, about 2-4%, or about 1-4%, or about 1-5%, or about 1-6%, or about 1-7%, or about 1-8%, or about 1-9%, or about 1-10%, or about 1-11%, or about 1-12%, or about 1-13%, or about 1-14%, or about 1-15% basic species. In some embodiments, the eluate fraction further comprises or the basic species in the eluate fraction is maintained at about 1-15% basic species.

In some embodiments, the eluate fraction further comprises or the main species in the eluate fraction is maintained at more than about 40%, e.g., about 41%, about 42%, about 43%, about 44%, about 45%, about 46%, about 47%, about 48%, about 49%, about 50%, about 55%, about 60%, about 61%, about 62%, about 63%, about 64%, about 65%, about 66%, about 67%, about 68%, about 69%, about 70%, about 75%, about 80%, about 85%, about 90%, about 95% or about 99% main species.

In some embodiments, the eluate fraction further comprises or the main species in the eluate fraction is maintained at about 40-70%, about 40-70%, about 40-65%, about 40-60%, about 40-55%, about 40-50%, about 55-75%, about 55-70%, about 60-70%, about 60-65%, or about 60-63% main species. In some embodiments, the eluate fraction further comprises or the main species in the eluate fraction is maintained at about 60-63% main species.

In some embodiments, the eluate fraction comprises or the acidic, basic and main species in the eluate fraction are maintained at about 30-55% acidic species, about 1-15% basic species, and about 40-75% main species.

In some embodiments, the eluate fraction comprises or the acidic, basic and main species in the eluate fraction are maintained at about 30-40% acidic species, about 1-5% basic species, and about 55-75% main species.

In some embodiments, the eluate fraction comprises or the acidic, basic and main species in the eluate fraction are maintained at about 34-36% acidic species, about 1-5% basic species, and about 60-63% main species.

In some embodiments, the elution buffer comprises about 1-500 mM, about 10-250 mM, about 50-200 mM, about 70-150 mM, about 90-130 mM, about 110-129 mM, about 110-125 mM, or about 110-120 mM, or about 110-130 mM sodium acetate. In some embodiments, the elution buffer comprises about 110-130 mM, about 110-129 mM, about 110-125 mM, or about 110-120 mM sodium acetate.

In some embodiments, the elution buffer comprises a pH of about 5-7 or about 5.5-6.5. In some embodiments, the elution buffer comprises a pH of about 5.5-6.5.

In some embodiments, the elution buffer comprises about 120 mM sodium acetate, and has a pH of about 6.0.

In some embodiments, the anti-IL-1R1 antibody or antigen-binding portion thereof is loaded onto the cation exchange chromatography resin at a level of about 10-120 g/L, about 20-110 g/L, about 30-1000 g/L, about 40-90 g/L, or about 70-80 g/L. In some embodiments, the anti-IL-1R1 antibody or antigen-binding portion thereof is loaded onto the cation exchange chromatography resin at a level of about 70-90 g/L.

In some embodiments, the method further comprises collecting a flow-through fraction from the anion exchange chromatography resin.

In some embodiments, the flow-through fraction comprises or the acidic species in the flow-through fraction is maintained at less than about 55%, about 54%, about 53%, about 52%, about 51%, about 50%, about 49%, about 48%, about 47%, about 46%, about 45%, about 44%, about 43%, about 42%, about 41%, about 40%, about 39%, about 38%, about 37%, about 36%, about 35%, about 34%, about 33%, about 32%, about 31%, about 30%, about 29%, about 28%, about 27%, about 26%, about 25%, about 24%, about 23%, about 22%, about 21%, about 20%, about 19%, about 18%, about 17%, about 16%, about 15%, about 14%, about 13%, about 12%, about 11%, or about 10% acidic species.

In some embodiments, the flow-through fraction comprises or the acidic species in the flow-through fraction is maintained at less than about 55% acidic species.

In some embodiments, the flow-through fraction comprises or the acidic species in the flow-through fraction is maintained at about 30-55%, about 31-55%, about 32-55%, about 33-55%, about 34-55%, about 35-55%, about 31-40%, about 32-40%, about 33-40%, about 34-40%, about 35-40%, about 31-39%, about 31-38%, about 31-37%, about 31-36%, about 32-39%, about 32-38%, about 32-37%, about 32-36%, about 33-39%, about 33-38%, about 33-37%, about 33-36%, about 34-39%, about 34-38%, about 34-37%, or about 34-36% acidic species.

In some embodiments, the flow-through fraction further comprises or the basic species in the flow-through fraction is maintained at less than about 15%, e.g., about 14%, about 13%, about 12%, about 11%, about 10%, about 9%, about 8%, about 7%, about 6%, about 5%, about 4%, about 3%, about 2%, or about 1%, basic species. In some embodiments, the flow-through fraction further comprises or the basic species in the flow-through fraction is maintained at about 1-5%, about 2-5%, about 2-4%, or about 1-4%, or about 1-5%, or about 1-6%, or about 1-7%, or about 1-8%, or about 1-9%, or about 1-10%, or about 1-11%, or about 1-12%, or about 1-13%, or about 1-14%, or about 1-15% basic species. In some embodiments, the flow-through fraction further comprises or the basic species in the flow-through fraction is maintained at about 1-15% basic species.

In some embodiments, the flow-through fraction further comprises or the main species in the flow-through fraction is maintained at more than about 40%, e.g., about 41%, about 42%, about 43%, about 44%, about 45%, about 46%, about 47%, about 48%, about 49%, about 50%, about 55%, about 60%, about 61%, about 62%, about 63%, about 64%, about 65%, about 66%, about 67%, about 68%, about 69%, about 70%, about 75%, about 80%, about 85%, about 90%, about 95% or about 99% main species.

In some embodiments, the flow-through fraction further comprises or the main species in the flow-through fraction is maintained at about 40-70%, about 40-70%, about 40-65%, about 40-60%, about 40-55%, about 40-50%, about 55-75%, about 55-70%, about 60-70%, about 60-65%, or about 60-63% main species. In some embodiments, the flow-through fraction further comprises or the main species in the flow-through fraction is maintained at about 60-63% main species.

In some embodiments, the flow-through fraction comprises or the acidic, basic and main species in the flow-through fraction are maintained at about 30-55% acidic species, about 1-15% basic species, and about 40-75% main species.

In some embodiments, the flow-through fraction comprises or the acidic, basic and main species in the flow-through fraction are maintained at about 30-40% acidic species, about 1-5% basic species, and about 55-75% main species.

In some embodiments, the flow-through fraction comprises or the acidic, basic and main species in the flow-through fraction are maintained at about 34-36% acidic species, about 1-5% basic species, and about 60-63% main species.

In some embodiments, the anti-IL-1R1 antibody or antigen-binding portion thereof is loaded onto the anion exchange chromatography resin at about 1-10 g/mL MV, about 2-9 g/mL MV, about 3-8 g/mL MV, about 3-6 g/mL MV, about 2.5-5 g/mL MV, about 3-5 g/mL MV, or about 3.5-5 g/mL MV. In some embodiments, the anti-IL-1R1 antibody or antigen-binding portion thereof is loaded onto the anion exchange chromatography resin at about 3.5-5 g/mL MV.

In some embodiments, the level of acidic species is determined by Imaging Capillary Isoelectric Focusing (iCIEF).

In one aspect, the present invention provides a composition comprising an anti-IL-1R1 antibody, or antigen-binding portion thereof, wherein the composition comprises less than about 10%, about 9%, about 8%, about 7%, about 6%, about 5%, about 4%, about 3%, about 2.5%, about 2%, or about 1% high molecular weight aggregates. In some embodiments, the composition comprises less than about 4% high molecular weight aggregates. In some embodiments, the composition comprises less than about 3% high molecular weight aggregates. In some embodiments, the comppositin comprises less than about 4% high molecular weight aggregates and less than about 100 ppm of host cell proteins (HCP). In some embodiments, the comppositin comprises less than about 4% high molecular weight aggregates, less than about 100 ppm of host cell proteins (HCP), and less than about 1.6 ppm Protein A (ProA).

In one aspect, the present invention provides a composition comprising an anti-IL-1R1 antibody, or antigen-binding portion thereof, wherein the composition comprises about 1-10%, about 1-9%, about 1-8%, about 1-7%, about 1-6%, about 1-5%, about 1-4%, about 1-3.5%, about 1-3%, about 1-2.5%, or about 1-2% high molecular weight aggregates. In some embodiments, the composition comprises about 1-3.5% high molecular weight aggregates. In some embodiments, the composition comprises about 1-3% high molecular weight aggregates. In some embodiments, the comppositin comprises about 1-3% high molecular weight aggregates and less than about 100 ppm of host cell proteins (HCP). In some embodiments, the comppositin comprises about 1-3% high molecular weight aggregates, less than about 100 ppm of host cell proteins (HCP), and less than about 1.6 ppm Protein A (ProA).

In one aspect, the present invention provides a composition comprising an anti-IL-1R1 antibody, or antigen-binding portion thereof, wherein the composition comprises more than about 90%, about 91%, about 92%, about 93%, about 94%, about 95%, about 96%, about 97%, about 98%, or about 99% antibody monomer. In some embodiments, the composition comprises more than about 97% antibody monomer. In some embodiments, the composition comprises more than about 96% antibody monomer. In some embodiments, the comppositin comprises more than about 96% antibody monomer and less than about 100 ppm of host cell proteins (HCP). In some embodiments, the comppositin comprises more than about 96% antibody monomer, less than about 100 ppm of host cell proteins (HCP), and less than about 1.6 ppm Protein A (ProA).

In one aspect, the present invention provides a composition comprising an anti-IL-1R1 antibody, or antigen-binding portion thereof, wherein the composition comprises about 90-99.9%, about 90-99%, about 95-99%, about 96.5-99%, about 96-99%, about 97-99%, or about 98-99% antibody monomer. In some embodiments, the composition comprises about 96.5-99% antibody monomer. In some embodiments, the composition comprises about 97-99% antibody monomer. In some embodiments, the comppositin comprises about 97-99% antibody monomer and less than about 100 ppm of host cell proteins (HCP). In some embodiments, the comppositin comprises about 97-99% antibody monomer, less than about 100 ppm of host cell proteins (HCP), and less than about 1.6 ppm Protein A (ProA).

In one aspect, the present invention provides a composition comprising an anti-IL-1R1 antibody, or antigen-binding portion thereof, wherein the composition comprises an eluate fraction collected from a cation exchange chromatography resin, and wherein the eluate fraction comprises less than about 10%, about 9%, about 8%, about 7%, about 6%, about 5%, about 4%, about 3%, about 2.5%, about 2%, or about 1% high molecular weight aggregates. In some embodiments, the eluate fraction comprises less than about 3% high molecular weight aggregates.

In one aspect, the present invention provides a composition comprising an anti-IL-1R1 antibody, or antigen-binding portion thereof, wherein the composition comprises an eluate fraction collected from a cation exchange chromatography resin, and wherein the eluate fraction comprises about 1-10%, about 1-9%, about 1-8%, about 1-7%, about 1-6%, about 1-5%, about 1-4%, about 1-3%, or about 1-2% high molecular weight aggregates. In some embodiments, the eluate fraction comprises about 1-3% high molecular weight aggregates.

In one aspect, the present invention provides a composition comprising an anti-IL-1R1 antibody, or antigen-binding portion thereof, wherein the composition comprises an eluate fraction collected from a cation exchange chromatography resin, and wherein the eluate fraction comprises more than about 90%, about 91%, about 92%, about 93%, about 94%, about 95%, about 96%, about 97%, about 98%, or about 99% antibody monomer. In some embodiments, the eluate fraction comprises more than about 97% antibody monomer.

In one aspect, the present invention provides a composition comprising an anti-IL-1R1 antibody, or antigen-binding portion thereof, wherein the composition an eluate fraction collected from a cation exchange chromatography resin, and wherein the eluate fraction comprises about 90-99.9%, about 90-99%, about 95-99%, about 96-99%, about 97-99%, or about 98-99% antibody monomer. In some embodiments, the eluate fraction comprises about 97-99% antibody monomer.

In one aspect, the present invention provides a composition comprising an anti-IL-1R1 antibody, or antigen-binding portion thereof, wherein the composition comprises a flow-through fraction collected from an anion exchange chromatography resin, and wherein the flow-through fraction comprises less than about 10%, about 9%, about 8%, about 7%, about 6%, about 5%, about 4%, about 3%, about 2.5%, about 2%, or about 1% high molecular weight aggregates. In some embodiments, the flow-through fraction comprises less than about 3% high molecular weight aggregates.

In one aspect, the present invention provides a composition comprising an anti-IL-1R1 antibody, or antigen-binding portion thereof, wherein the composition comprises a flow-through fraction collected from an anion exchange chromatography resin, and wherein the flow-through fraction comprises about 1-10%, about 1-9%, about 1-8%, about 1-7%, about 1-6%, about 1-5%, about 1-4%, about 1-3%, or about 1-2% high molecular weight aggregates. In some embodiments, the flow-through fraction comprises about 1-3% high molecular weight aggregates.

In one aspect, the present invention provides a composition comprising an anti-IL-1R1 antibody, or antigen-binding portion thereof, wherein the composition comprises a flow-through fraction collected from an anion exchange chromatography resin, and wherein the flow-through fraction comprises more than about 90%, about 91%, about 92%, about 93%, about 94%, about 95%, about 96%, about 97%, about 98%, or about 99% antibody monomer. In some embodiments, the flow-through fraction comprises more than about 97% antibody monomer.

In one aspect, the present invention provides a composition comprising an anti-IL-1R1 antibody, or antigen-binding portion thereof, wherein the composition comprises a flow-through fraction collected from an anion exchange chromatography resin, and wherein the flow-through fraction comprises about 90-99.9%, about 90-99%, about 95-99%, about 96-99%, about 97-99%, or about 98-99% antibody monomer. In some embodiments, the flow-through fraction comprises about 97-99% antibody monomer.

In some embodiments, the anti-IL-1R1 antibody, or antigen-binding portion thereof, comprises a heavy chain variable region comprising a CDR1 having an amino acid sequence of SEQ ID NO:1, a CDR2 having an amino acid sequence of SEQ ID NO:2, and a CDR3 having an amino acid sequence of SEQ ID NO:3.

In some embodiments, the anti-IL-1R1 antibody, or antigen-binding portion thereof, comprises a light chain variable region comprising a CDR1 having an amino acid sequence of SEQ ID NO:4, a CDR2 having an amino acid sequence of SEQ ID NO:5, and a CDR3 having an amino acid sequence of SEQ ID NO:6.

In some embodiments, the anti-IL-1R1 antibody, or antigen-binding portion thereof, comprises a heavy chain variable region comprising an amino acid sequence of SEQ ID NO:7, and a light chain variable region comprising an amino acid sequence of SEQ ID NO:8.

In some embodiments, the anti-IL-1R1 antibody, or antigen-binding portion thereof, comprises a heavy chain comprising an amino acid sequence of SEQ ID NO:9, and a light chain comprising an amino acid sequence of SEQ ID NO:10.

In some embodiments, the anti-IL-1R1 antibody, or antigen-binding portion thereof, is KPL-387.

In some embodiments, the level of high molecular weight aggregates, or the level of antibody monomer are determined by size exclusion chromatography.

In one aspect, the present invention provides a method of producing a composition comprising an anti-IL-1R1 antibody, or antigen-binding portion thereof, having about 1-10% or less than about 10%, about 9%, about 8%, about 7%, about 6%, about 5%, about 4%, about 3.5%, about 3%, about 2.5%, or about 2% high molecular weight aggregates, the method comprising subjecting a sample comprising the anti-IL-1R1 antibody, or antigen-binding portion thereof, to a chromatography resin, wherein the chromatography resin is selected from a group consisting of a cation exchange chromatography resin and an anion exchange chromatography resin, or combinations thereof, thereby producing the composition comprising the anti-IL-1R1 antibody, or antigen-binding portion thereof, having about 1-10% or less than about 10%, about 9%, about 8%, about 7%, about 6%, about 5%, about 4%, about 3.5%, about 3%, about 2.5%, or about 2% high molecular weight aggregates.

In one aspect, the present invention provides a method of preventing the level of high molecular weight aggregates from exceeding about 10%, about 9%, about 8%, about 7%, about 6%, about 5%, about 4%, about 3.5%, about 3%, about 2.5%, or about 2% in a composition comprising an anti-IL-1R1 antibody, or antigen-binding portion thereof, the method comprising subjecting a sample comprising the anti-IL-1R1 antibody, or antigen-binding portion thereof, to a chromatography resin, wherein the chromatography resin is selected from a group consisting of a cation exchange chromatography resin and an anion exchange chromatography resin, or combinations thereof, thereby preventing the level of high molecular weight aggregates from exceeding about 10%, about 9%, about 8%, about 7%, about 6%, about 5%, about 4%, about 3.5%, about 3%, about 2.5%, or about 2% in the composition comprising the anti-IL-1R1 antibody, or antigen-binding portion thereof.

In some embodiments, the method prevents the level of high molecular weight aggregates from exceeding about 9%, about 8%, about 7%, about 6%, about 5%, about 4%, about 3.5%, about 3%, about 2.5%, or about 2% in the composition.

In one aspect, the present invention provides a method of maintaining the level of high molecular weight aggregates at about 1-10% or less than about 10%, about 9%, about 8%, about 7%, about 6%, about 5%, about 4%, about 3.5%, about 3%, about 2.5%, or about 2% in a composition comprising an anti-IL-1R1 antibody, or antigen-binding portion thereof, the method comprising subjecting a sample comprising the anti-IL-1R1 antibody, or antigen-binding portion thereof, to a chromatography resin, wherein the chromatography resin is selected from a group consisting of a cation exchange chromatography resin and an anion exchange chromatography resin, or combinations thereof, thereby maintaining the level of high molecular weight aggregates at about 1-10% or less than about 10%, about 9%, about 8%, about 7%, about 6%, about 5%, about 4%, about 3.5%, about 3%, about 2.5%, or about 2% in the composition.

In some embodiments, the method further comprises maintaining the level of antibody monomer at about 90-99.9%, or preventing the level of antibody monomer from dropping below 90%.

In one aspect, the present invention provides a method of producing a composition comprising an anti-IL-1R1 antibody, or antigen-binding portion thereof, having about 90-99.9% or more than about 90%, about 91%, about 92%, about 93%, about 94%, about 95%, about 96%, about 96.5%, about 97%, about 98%, or about 99% antibody monomer, the method comprising subjecting a sample comprising the anti-IL-1R1 antibody, or antigen-binding portion thereof, to a chromatography resin, wherein the chromatography resin is selected from a group consisting of a cation exchange chromatography resin and an anion exchange chromatography resin, or combinations thereof, thereby producing the composition comprising the anti-IL-1R1 antibody, or antigen-binding portion thereof, having about 90-99.9% or more than about 90%, about 91%, about 92%, about 93%, about 94%, about 95%, about 96%, about 96.5%, about 97%, about 98%, or about 99% antibody monomer.

In one aspect, the present invention provides a method of preventing the level of antibody monomer from dropping below about 90%, about 91%, about 92%, about 93%, about 94%, about 95%, abou 96.5%, about 96%, about 97%, about 98%, or about 99% in a composition comprising an anti-IL-1R1 antibody, or antigen-binding portion thereof, the method comprising subjecting a sample comprising the anti-IL-1R1 antibody, or antigen-binding portion thereof, to a chromatography resin, wherein the chromatography resin is selected from a group consisting of a cation exchange chromatography resin and an anion exchange chromatography resin, or combinations thereof, thereby preventing the level of antibody monomer from dropping below about 90%, about 91%, about 92%, about 93%, about 94%, about 95%, about 96%, about 96.5%, about 97%, about 98%, or about 99% in the composition comprising the anti-IL-1R1 antibody, or antigen-binding portion thereof.

In some embodiments, the method prevents the level of antibody monomer from dropping below about 91%, about 92%, about 93%, about 94%, about 95%, about 96%, about 96.5%, about 97%, about 98%, or about 99% in the composition.

In one aspect, the present invention provides a method of maintaining the level of antibody monomer at about 90-99.9% or more than about 90%, about 91%, about 92%, about 93%, about 94%, about 95%, about 96%, about 96.5%, about 97%, about 98%, or about 99% in a composition comprising an anti-IL-1R1 antibody, or antigen-binding portion thereof, the method comprising subjecting a sample comprising the anti-IL-1R1 antibody, or antigen-binding portion thereof, to a chromatography resin, wherein the chromatography resin is selected from a group consisting of a cation exchange chromatography resin and an anion exchange chromatography resin, or combinations thereof, thereby maintaining the level of antibody monomer at about 90-99.9% or more than about 90%, about 91%, about 92%, about 93%, about 94%, about 95%, about 96%, about 96.5%, about 97%, about 98%, or about 99% in the composition.

In some embodiments, the method further comprises maintaining the level of high molecular weight aggregates at about 1-10%, or preventing the level of high molecular weight aggregates from exceeding about 10%.

In some embodiments, the anti-IL-1R1 antibody or antigen-binding portion thereof, comprises a heavy chain variable region comprising a CDR1 having an amino acid sequence of SEQ ID NO:1, a CDR2 having an amino acid sequence of SEQ ID NO:2, and a CDR3 having an amino acid sequence of SEQ ID NO:3.

In some embodiments, the anti-IL-1R1 antibody, or antigen-binding portion thereof, comprises a light chain variable region comprising a CDR1 having an amino acid sequence of SEQ ID NO:4, a CDR2 having an amino acid sequence of SEQ ID NO:5, and a CDR3 having an amino acid sequence of SEQ ID NO:6.

In some embodiments, the anti-IL-1R1 antibody, or antigen-binding portion thereof, comprises a heavy chain variable region comprising an amino acid sequence of SEQ ID NO:7, and a light chain variable region comprising an amino acid sequence of SEQ ID NO:8.

In some embodiments, the anti-IL-1R1 antibody, or antigen-binding portion thereof, comprises a heavy chain comprising an amino acid sequence of SEQ ID NO:9, and a light chain comprising an amino acid sequence of SEQ ID NO:10.

In some embodiments, the anti-IL-1R1 antibody, or antigen-binding portion thereof, is KPL-387.

In some embodiments, the sample is subject to a cation exchange chromatography resin.

In some embodiments, the cation exchange chromatography resin comprises a functional group selected from the group consisting of sulpfhydryl, sulfonate, sulfate, carboxymethyl, sulfoethyl, sulfopropyl, phosphate and sulfonate.

In some embodiments, the cation exchange chromatography resin is selected from the group consisting of POROS™ XS CEX, Capto™ S ImpAct, TOTOPEARL™ GigaGap CM 650M, and TOYOPEAL™ sulfate 650F.

In some embodiments, the cation exchange chromatography resin runs in bind-elute mode.

In some embodiments, an elution step of the cation exchange chromatography is carried out at a pH of greater than about 5.7, e.g., a pH of about 5.8, about 5.9, about 6.0, or about 6.1.

In some embodiments, the elution step of the cation exchange chromatography is carried out at a pH of about 5.8-6.0. In some embodiments, the elution step of the cation exchange chromatography is carried out at a pH of about 5.8-6.1.

In one embodiment, a wash buffer and/or an elution buffer are added to achieve a pH of greater than 5.7, e.g., a pH of about 5.8, about 5.9, about 6.0, or about 6.1, during the elution step of the cation exchange chromatography.

In one embodiment, a wash buffer and/or an elution buffer are added to achieve a pH of about 5.8-6.0 during the elution step of the cation exchange chromatography. In one embodiment, a wash buffer and/or an elution buffer are added to achieve a pH of about about 5.8-6.1 during the elution step of the cation exchange chromatography.

In some embodiments, the elution buffer comprises about 1-500 mM, about 10-250 mM, about 50-200 mM, about 70-150 mM, about 90-130 mM, about 110-130 mM, about 110-129 mM, about 110-125 mM, or about 110-120 mM sodium acetate. In some embodiments, the elution buffer comprises about 110-130 mM sodium acetate. In some embodiments, the elution buffer comprises about 110-129 mM. In some embodiments, the elution buffer comprises about 110-125 mM. In some embodiments, the elution buffer comprises about 110-120 mM.

In some embodiments, the elution buffer comprises a pH of about 5-7, about 5.5-6.5, about 5.8-6.2, about 5.8-6.1, or about 5.8-6.0. In some embodiments, the elution buffer comprises a pH of about 5.8-6.2. In some embodiments, the elution buffer comprises a pH of about 5.8-6.1.

In some embodiments, the elution buffer comprises about 110-130 mM sodium acetate, and has a pH of about 5.8-6.2. In some embodiments, the elution buffer comprises about 110-129 mM sodium acetate, and a pH of about 5.8-6.1. In some embodiments, the elution buffer comprises about 110-125 mM sodium acetate, and a pH of about 5.8-6.1. In some embodiments, the elution buffer comprises about 110-120 mM sodium acetate, and a pH of about 5.8-6.0. In some embodiments, the elution buffer comprises about 110-125 mM sodium acetate, and a pH of about 5.8-6.0.

In some embodiments, the elution buffer comprises about 120 mM sodium acetate, and has a pH of about 6.0. In some embodiments, the elution buffer comprises about 110 mM sodium acetate, and has a pH of about 5.8. In some embodiments, the elution buffer comprises about 130 mM sodium acetate, and has a pH of about 6.2.

In some embodiments, the wash buffer comprises about 1-500 mM, about 10-100 mM, about 10-30 mM, about 20-50 mM, or about 40-70 mM M sodium acetate.

In some embodiments, the wash buffer comprises a pH of about 4-7, about 4.5-6.5, about 4.8-6.2, about 4.8-5.8, about 5-6, about 5.0-6.1, or about 5.2-6.2.

In some embodiments, the wash buffer comprises about 20-50 mM sodium acetate and a pH of about 5-6. In some embodiments, the wash buffer comprises about 10-30 mM sodium acetate and a pH of about 4.8-5.8. In some embodiments, the wash buffer comprises about 40-70 mM sodium acetate and a pH of about 5.2-6.2.

In some embodiments, the sample is subject to an anion exchange chromatography resin.

In some embodiments, the anion exchange chromatography resin comprises a functional group selected from the group consisting of quaternary ammonium, quaternary polyethyleneimine, methacrylate, trimethylammoniumethyl, diethylaminoethyl, quaternary aminoethyl and quaternary amine.

In some embodiments, the anion exchange chromatography resin is selected from the group consisting of Sartobind Q, POROS™ HQ, Fractogel TMAE, and Q sepharose Fast Flow.

In some embodiments, the anion exchange chromatography resin runs in flow-through mode.

In some embodiments, the sample is subject to a cation exchange chromatography resin followed by an anion exchange chromatography resin.

In some embodiments, prior to subjecting said sample to the cation exchange chromatography resin and the anion exchange chromatography resin, the sample is subjected to an affinity chromatography resin.

In some embodiments, the affinity chromatography resin is selected from the group consisting of MabSelect PrismA, Amsphere A3, Gore membrane, MabSelect SuRe LX, MabSelect SuRe™, MabSelect, MabSelect Xtra, Protein A Sepharose, ProSep HC, ProSep Ultra, ProSep Ultra Plus, and MapCapture.

In some embodiments, the composition comprises or the high molecular weight aggregates in the composition is maintained at less than about 10%, about 9%, about 8%, about 7%, about 6%, about 5%, about 4%, about 3%, about 2.5%, about 2%, or about 1% high molecular weight aggregates. In some embodiments, the composition comprises or the high molecular weight aggregates in the composition is maintained at less than about 4% high molecular weight aggregates. In some embodiments, the composition comprises or the high molecular weight aggregates in the composition is maintained at less than about 3% high molecular weight aggregates. In some embodiments, the composition comprises or the high molecular weight aggregates in the composition is maintained at less than about 4% high molecular weight aggregates, and the composition comprises less than about 100 ppm of host cell proteins (HCP). In some embodiments, the composition comprises or the high molecular weight aggregates in the composition is maintained at less than about 4% high molecular weight aggregates, and the composition comprises less than about 100 ppm of host cell proteins (HCP), and less than about 1.6 ppm Protein A (ProA).

In some embodiments, the composition comprises or the high molecular weight aggregates in the composition is maintained at about 1-10%, about 1-9%, about 1-8%, about 1-7%, about 1-6%, about 1-5%, about 1-4%, about 1-3.5%, about 1-3%, about 1-2.5%, or about 1-2% high molecular weight aggregates. In some embodiments, the composition comprises or the high molecular weight aggregates in the composition is maintained at about 1-3.5% high molecular weight aggregates. In some embodiments, the composition comprises or the high molecular weight aggregates in the composition is maintained at about 1-3% high molecular weight aggregates. In some embodiments, the composition comprises or the high molecular weight aggregates in the composition is maintained at about 1-3% high molecular weight aggregates, and the composition comprises less than about 100 ppm of host cell proteins (HCP). In some embodiments, the composition comprises or the high molecular weight aggregates in the composition is maintained at about 1-3% high molecular weight aggregates, and the composition comprises less than about 100 ppm of host cell proteins (HCP), and less than about 1.6 ppm Protein A (ProA).

In some embodiments, the composition further comprises or the antibody monomer in the composition is maintained at more than about 90%, about 91%, about 92%, about 93%, about 94%, about 95%, about 96%, about 97%, about 98%, or about 99% antibody monomer. In some embodiments, the composition further comprises or the antibody monomer in the composition is maintained at more than 96% antibody monomer. In some embodiments, the composition further comprises or the antibody monomer in the composition is maintained at more than 96% antibody monomer, and the composition comprises less than about 100 ppm of host cell proteins (HCP). In some embodiments, the composition further comprises or the antibody monomer in the composition is maintained at more than 96% antibody monomer, and the composition comprises less than about 100 ppm of host cell proteins (HCP), and less than about 1.6 ppm Protein A (ProA). In some embodiments, the composition further comprises or the antibody monomer in the composition is maintained at about 90-99.9%, about 90-99%, about 95-99%, about 96-99%, about 96.5-99%, about 97-99%, or about 98-99% antibody monomer. In some embodiments, the composition further comprises or the antibody monomer in the composition is maintained at about 96.5-99% antibody monomer. In some embodiments, the composition further comprises or the antibody monomer in the composition is maintained at about 97-99% antibody monomer. In some embodiments, the composition further comprises or the antibody monomer in the composition is maintained at about 97-99% antibody monomer, and the composition comprises less than about 100 ppm of host cell proteins (HCP). In some embodiments, the composition further comprises or the antibody monomer in the composition is maintained at about 97-99% antibody monomer, and the composition comprises less than about 100 ppm of host cell proteins (HCP), and less than about 1.6 ppm Protein A (ProA).

In some embodiments, the method further comprises collecting an eluate fraction from the cation exchange chromatography resin using an elution buffer.

In some embodiments, the eluate fraction comprises or the high molecular weight aggregates in the eluate fraction is maintained at less than about 10%, about 9%, about 8%, about 7%, about 6%, about 5%, about 4%, about 3%, about 2.5%, about 2%, or about 1% high molecular weight aggregates. In some embodiments, the eluate fraction comprises or the high molecular weight aggregates in the eluate fraction is maintained at less than about 4% high molecular weight aggregates. In some embodiments, the eluate fraction comprises or the high molecular weight aggregates in the eluate fraction is maintained at less than about 3% high molecular weight aggregates. In some embodiments, the eluate fraction comprises or the high molecular weight aggregates in the eluate fraction is maintained at less than about 4% high molecular weight aggregates, and the eluate fraction comprises less than about 100 ppm of host cell proteins (HCP). In some embodiments, the eluate fraction comprises or the high molecular weight aggregates in the eluate fraction is maintained at less than about 4% high molecular weight aggregates, and the eluate fraction comprises less than about 100 ppm of host cell proteins (HCP), and less than about 1.6 ppm Protein A (ProA).

In some embodiments, the eluate fraction comprises or the high molecular weight aggregates in the eluate fraction is maintained at about 1-10%, about 1-9%, about 1-8%, about 1-7%, about 1-6%, about 1-5%, about 1-4%, about 1-3.5%, about 1-3%, about 1-2.5%, or about 1-2% high molecular weight aggregates. In some embodiments, the eluate fraction comprises or the high molecular weight aggregates in the eluate fraction is maintained at about 1-3.5% high molecular weight aggregates. In some embodiments, the eluate fraction comprises or the high molecular weight aggregates in the eluate fraction is maintained at about 1-3% high molecular weight aggregates. In some embodiments, the eluate fraction comprises or the high molecular weight aggregates in the eluate fraction is maintained at about 1-3% high molecular weight aggregates, and the eluate fraction comprises less than about 100 ppm of host cell proteins (HCP). In some embodiments, the eluate fraction comprises or the high molecular weight aggregates in the eluate fraction is maintained at about 1-3% high molecular weight aggregates, and the eluate fraction comprises less than about 100 ppm of host cell proteins (HCP), and less than about 1.6 ppm Protein A (ProA).

In some embodiments, the eluate fraction further comprises or the antibody monomer in the eluate fraction is maintained at more than about 90%, about 91%, about 92%, about 93%, about 94%, about 95%, about 96%, about 97%, about 98%, or about 99% antibody monomer. In some embodiments, the eluate fraction further comprises or the antibody monomer in the eluate fraction is maintained at more than 96% antibody monomer. In some embodiments, the eluate fraction further comprises or the antibody monomer in the eluate fraction is maintained at more than 96% antibody monomer, and the eluate fraction comprises less than about 100 ppm of host cell proteins (HCP). In some embodiments, the eluate fraction further comprises or the antibody monomer in the eluate fraction is maintained at more than 96% antibody monomer, and the eluate fraction comprises less than about 100 ppm of host cell proteins (HCP), and less than about 1.6 ppm Protein A (ProA).

In some embodiments, the eluate fraction further comprises or the antibody monomer in the eluate fraction is maintained at about 90-99.9%, about 90-99%, about 95-99%, about 96-99%, about 96.5-99%, about 97-99%, or about 98-99% antibody monomer. In some embodiments, the eluate fraction further comprises or the antibody monomer in the eluate fraction at about 96.5-99% antibody monomer. In some embodiments, the eluate fraction further comprises or the antibody monomer in the eluate fraction at about 97-99% antibody monomer. In some embodiments, the eluate fraction further comprises or the antibody monomer in the eluate fraction is maintained at about 97-99% antibody monomer, and the eluate fraction comprises less than about 100 ppm of host cell proteins (HCP). In some embodiments, the eluate fraction further comprises or the antibody monomer in the eluate fraction is maintained at about 97-99% antibody monomer, and the eluate fraction comprises less than about 100 ppm of host cell proteins (HCP), and less than about 1.6 ppm Protein A (ProA).

In some embodiments, the anti-IL-1R1 antibody or antigen-binding portion thereof is loaded onto the cation exchange chromatography resin at a level of about 10-120 g/L, about 20-110 g/L, about 30-1000 g/L, about 40-90 g/L, or about 70-80 g/L. In some embodiments, the anti-IL-1R1 antibody or antigen-binding portion thereof is loaded onto the cation exchange chromatography resin at a level of about 70-90 g/L.

In some embodiments, the method further comprises collecting a flow-through fraction from the anion exchange chromatography resin.

In some embodiments, the flow-through fraction comprises or the high molecular weight aggregates in the flow-through fraction is maintained at less than about 10%, about 9%, about 8%, about 7%, about 6%, about 5%, about 4%, about 3%, about 2.5%, about 2%, or about 1% high molecular weight aggregates. In some embodiments, the flow-through fraction comprises or the high molecular weight aggregates in the flow-through fraction is maintained at less than about 3% high molecular weight aggregates.

In some embodiments, the flow-through fraction comprises or the high molecular weight aggregates in the flow-through fraction is maintained at about 1-10%, about 1-9%, about 1-8%, about 1-7%, about 1-6%, about 1-5%, about 1-4%, about 1-3%, or about 1-2% high molecular weight aggregates. In some embodiments, the flow-through fraction comprises or the high molecular weight aggregates in the flow-through fraction is maintained at about 1-3% high molecular weight aggregates.

In some embodiments, the flow-through fraction further comprises or the antibody monomer in the flow-through fraction is maintained at more than about 90%, about 91%, about 92%, about 93%, about 94%, about 95%, about 96%, about 97%, about 98%, or about 99% antibody monomer.

In some embodiments, the flow-through fraction further comprises or the antibody monomer in the flow-through fraction is maintained at about 90-99.9%, about 90-99%, about 95-99%, about 96-99%, about 97-99%, or about 98-99% antibody monomer. In some embodiments, the flow-through fraction further comprises or the antibody monomer in the flow-through fraction at about 97-99% antibody monomer.

In some embodiments, the anti-IL-1R1 antibody or antigen-binding portion thereof is loaded onto the anion exchange chromatography resin at about 1-10 g/mL membrane volume (MV), about 2-9 g/mL MV, about 3-8 g/mL MV, about 3-6 g/mL MV, about 2.5-5 g/mL MV, about 3-5 g/mL MV, or about 3.5-5 g/mL MV. In some embodiments, the anti-IL-1R1 antibody or antigen-binding portion thereof is loaded onto the anion exchange chromatography resin at about 3.5-5 g/mL MV. In some embodiments, the level of high molecular weight aggregates, or the level of antibody monomer are determined by size exclusion chromatography.

In one aspect, the present invention provides a method of producing a composition comprising an anti-IL-1R1 antibody, or antigen-binding portion thereof, having less than about 55% acidic species or between about 30-55% acidic species from a cell culture. The method comprises inoculating the cell culture at a seeding density of about $0.4 \times 10^6$ to about $0.8 \times 10^6$ cells/mL, thereby producing the composition comprising the anti-IL-1R1 antibody, or antigen-binding portion thereof, having less than about 55% acidic species or between about 30-55% acidic species.

In one aspect, the present invention provides a method of producing a composition comprising an anti-IL-1R1 antibody, or antigen-binding portion thereof, having less than about 55% acidic species or between about 30-55% acidic species from a cell culture. The method comprises incubating the cell culture in a bioreactor for about 8 to about 24 days, or for no more than about 24 days, thereby producing the composition comprising the anti-IL-1R1 antibody, or antigen-binding portion thereof, having less than about 55% acidic species or between about 30-55% acidic species.

In one aspect, the present invention provides a method of producing a composition comprising an anti-IL-1R1 antibody, or antigen-binding portion thereof, having less than about 55% acidic species or between about 30-55% acidic species from a cell culture. The method comprises maintaining the viability of the cell culture at a level of at least about 50%, thereby producing the composition comprising the anti-IL-1R1 antibody, or antigen-binding portion thereof, having less than about 55% acidic species or between about 30-55% acidic species.

In one aspect, the present invention provides a method of producing a composition comprising an anti-IL-1R1 antibody, or antigen-binding portion thereof, having less than about 55% acidic species or between about 30-55% acidic species from a cell culture. The method comprises harvesting the cell culture when the viability decreases to no less than about 50%, thereby producing the composition comprising the anti-IL-1R1 antibody, or antigen-binding portion thereof, having less than about 55% acidic species or between about 30-55% acidic species.

In one aspect, the present invention provides a method of producing a composition comprising an anti-IL-1R1 antibody, or antigen-binding portion thereof, having less than about 55% acidic species or between about 30-55% acidic species from a cell culture. The method comprises harvesting the cell culture when the viability is at least about 50%, thereby producing the composition comprising the anti-IL-1R1 antibody, or antigen-binding portion thereof, having less than about 55% acidic species or between about 30-55% acidic species.

In one aspect, the present invention provides a method of producing a composition comprising an anti-IL-1R1 antibody, or antigen-binding portion thereof, having less than about 55% acidic species or between about 30-55% acidic species from a cell culture. The method comprises (a) inoculating the cell culture at a seeding density of about $0.4 \times 10^6$ to about $0.8 \times 10^6$ cells/mL, (b) incubating the cell culture in a bioreactor for about 8 to about 24 days, or for no more than about 24 days, (c) maintaining the viability of the cell culture at a level of at least about 50%, and/or (d) harvesting the cell culture when the viability is at least about 50% or when the viability decreases to no less than about 50%, thereby producing the composition comprising the anti-IL-1R1 antibody, or antigen-binding portion thereof, having less than about 55% acidic species or between about 30-55% acidic species.

In one aspect, the present invention provides a method of reducing the level of acidic species of an anti-IL-1R1 antibody, or antigen-binding portion thereof, in a clarified harvest from a cell culture. The method comprises inoculating the cell culture at a seeding density of about $0.4 \times 10^6$ to about $0.8 \times 10^6$ cells/mL, thereby reducing the level of acidic species of the anti-IL-1R1 antibody, or antigen-binding portion thereof, in the clarified harvest.

In one aspect, the present invention provides a method of reducing the level of acidic species of an anti-IL-1R1 antibody, or antigen-binding portion thereof, in a clarified harvest from a cell culture. The method comprises incubating the cell culture in a bioreactor for about 8 to about 24 days, or for no more than about 24 days, thereby reducing the level of acidic species of the anti-IL-1R1 antibody, or antigen-binding portion thereof, in the clarified harvest.

In one aspect, the present invention provides a method of reducing the level of acidic species of an anti-IL-1R1 antibody, or antigen-binding portion thereof, in a clarified harvest from a cell culture. The method comprises maintaining the viability of the cell culture at a level of at least about 50%, thereby reducing the level of acidic species of the anti-IL-1R1 antibody, or antigen-binding portion thereof, in the clarified harvest.

In one aspect, the present invention provides a method of reducing the level of acidic species of an anti-IL-1R1 antibody, or antigen-binding portion thereof, in a clarified harvest from a cell culture. The method comprises harvesting the cell culture when the viability decreases to no less than about 50%, thereby reducing the level of acidic species of the anti-IL-1R1 antibody, or antigen-binding portion thereof, in the clarified harvest.

In one aspect, the present invention provides a method of reducing the level of acidic species of an anti-IL-1R1 antibody, or antigen-binding portion thereof, in a clarified harvest from a cell culture. The method comprises harvesting the cell culture when the viability is at least about 50%, thereby reducing the level of acidic species of the anti-IL-1R1 antibody, or antigen-binding portion thereof, in the clarified harvest.

In one aspect, the present invention provides a method of reducing the level of acidic species of an anti-IL-1R1 antibody, or antigen-binding portion thereof, in a clarified harvest from a cell culture. The method comprises (a) inoculating the cell culture at a seeding density of about $0.4 \times 10^6$ to about $0.8 \times 10^6$ cells/mL, (b) incubating the cell culture in a bioreactor for about 8 to about 24 days, or for no more than about 24 days, (c) maintaining the viability of the cell culture at a level of at least about 50%, and/or (d) harvesting the cell culture when the viability is at least about 50% or when the viability decreases to no less than about 50%, thereby reducing the level of acidic species of the anti-IL-1R1 antibody, or antigen-binding portion thereof, in the clarified harvest.

In some embodiments, the clarified harvest comprises less than about 55%, or about 30-55% acid species.

In some embodiments, the seeding density of the cell culture is about $0.4 \times 10^6$ to about $0.8 \times 10^6$ cells/mL, about $0.4 \times 10^6$ to about $0.7 \times 10^6$ cells/mL, or about $0.4 \times 10^6$ to about $0.6 \times 10^6$ cells/mL. In some embodiments, the seeding density of the cell culture is about $0.4 \times 10^6$ to about $0.6 \times 10^6$ cells/mL.

In some embodiments, the seeding density of the cell culture is about $0.4 \times 10^6$ cells/mL, about $0.5 \times 10^6$ cells/mL, about $0.6 \times 10^6$ cells/mL, about $0.7 \times 10^6$ cells/mL, or about $0.8 \times 10^6$ cells/mL. In some embodiments, the seeding density of the cell culture is about about $0.4 \times 10^6$ cells/mL. In some embodiments, the seeding density of the cell culture is about about $0.5 \times 10^6$ cells/mL. In some embodiments, the seeding density of the cell culture is about about $0.6 \times 10^6$ cells/mL.

In some embodiments, the cell culture is incubated in the bioreactor for about 8 to about 24 days, about 8 to about 22 days, about 8 to about 20 days, about 8 to about 18 days, or about 8 to about 16 days. In some embodiments, the cell culture is incubated in the bioreactor for about 8 to about 16 days.

In some embodiments, the cell culture is incubated in the bioreactor for no more than about 24 days, no more than about 23 days, no more than about 22 days, no more than about 21 days, no more than about 20 days, no more than about 19 days, no more than about 18 days, no more than about 17 days, or no more than about 16 days. In some embodiments, the cell culture is incubated in the bioreactor for no more than about 16 days.

In some embodiments, the cell culture is incubated in the bioreactor for about 24 days, about 23 days, about 22 days, about 21 days, about 20 days, about 19 days, about 18 days, about 17 days, about 16 days, about 15 days, about 14 days, about 13 days, about 12 days, about 11 days, about 10 days, about 9 days, or about 8 days. In some embodiments, the cell culture is incubated in the bioreactor for about 16 days.

In some embodiments, the viability of the cell culture is maintained at a level of about 50%-100%, about 55%-100%, about 60%-100% about 65%-100%, about 70%-100%, about 75%-100%, about 80%-100%, about 85%-100%, about 90%-100%, about 50%-70%, or about 55%-65%. In some embodiments, the viability of the cell culture is maintained at a level of about 60%-100%.

In some embodiments, the viability of the cell culture is maintained at a level of at least about 50%, about 55%, about 60%, about 65%, about 70%, about 75%, about 80%, about 85%, about 90%, about 95%, or about 99%. In some embodiments, the viability of the cell culture is maintained at a level of at least about 50%, about 55%, about 60%, about 65%, or about 70%.

In some embodiments, the cell culture is harvested when the viability of the cell culture decreases to about 50%-100%, about 55%-100%, about 60%-100%, about 65%-100%, about 70%-100%, about 75%-100%, about 80%-100%, about 85%-100%, about 90%-100%, about 50%-70%, or about 55%-65%. In some embodiments, the cell culture is harvested when the viability of the cell culture decreases to about 60%-100%. In some embodiments, the cell culture is harvested when the viability of the cell culture decreases to about 50%-70%. In some embodiments, the cell culture is harvested when the viability of the cell culture decreases to about 55%-65%.

In some embodiments, the cell culture is harvested when the viability of the cell culture decreases to no less than about 50%, about 55%, about 60%, about 65%, about 70%, about 75%, about 80%, about 85%, about 90%, about 95%, or about 99%. In some embodiments, the cell culture is harvested when the viability of the cell culture decreases to about 50%, about 55%, about 60%, about 65%, or about 70%.

In some embodiments, the cell culture is harvested when the viability of the cell culture is about 50%-100%, about 55%-100%, about 60%-100%, about 65%-100%, about 70%-100%, about 75%-100%, about 80%-100%, about 85%-100%, about 90%-100%, about 50%-70%, or about 55%-65%. In some embodiments, the cell culture is harvested when the viability of the cell culture is about 60%-100%. In some embodiments, the cell culture is harvested when the viability of the cell culture is about 50%-70%. In some embodiments, the cell culture is harvested when the viability of the cell culture is about 55%-75%.

In some embodiments, the cell culture is harvested when the viability of the cell culture is at least about 50%, about 55%, about 60%, about 65%, about 70%, about 75%, about 80%, about 85%, about 90%, about 95%, or about 99%.

In some embodiments, the cell culture is harvested when the viability of the cell culture is about 50%, about 55%, about 60%, about 65%, or about 70%.

In some embodiments, the composition or the clarified harvest comprises about about 30-55%, about 31-55%, about 32-55%, about 33-55%, about 34-55%, about 35-55%, 30-45%, about 30-40%, about 31-40%, about 32-40%, about 33-40%, about 34-40%, about 35-40%, about 31-39%, about 31-38%, about 31-37%, about 31-36%, about 32-39%, about 32-38%, about 32-37%, about 32-36%, about 33-39%, about 33-38%, about 33-37%, about 33-36%, about 34-39%, about 34-38%, about 34-37%, or about 34-36% acidic species of the antibody.

In some embodiments, the composition or the clarified harvest comprises less than about 55%, about 54%, about 53%, about 52%, about 51%, about 50%, about 49%, about 48%, about 47%, about 46%, about 45%, about 44,%, about 43%, about 42%, about 41%, about 40%, about 39%, about 38%, about 37%, about 36%, about 35%, about 34%, about 33%, about 32%, about 31%, about 30%, about 29%, about 28%, about 27%, about 26%, about 25%, about 24%, about 23%, about 22%, about 21%, about 20%, about 19%, about 18%, about 17%, about 16%, about 15%, about 14%, about 13%, about 12%, about 11%, or about 10% acidic species of the antibody.

In some embodiments, the composition or the clarified harvest comprises about 1-5%, about 2-5%, about 2-4%, about 1-4%, or about 1-5%, or about 1-6%, or about 1-7%, or about 1-8%, or about 1-9%, or about 1-10%, or about 1-11%, or about 1-12%, or about 1-13%, or about 1-14%, or about 1-15% basic species of the antibody.

In some embodiments, the composition or the clarified harvest comprises less than about 15%, e.g., about 14%, about 13%, about 12%, about 11%, about 10%, about 9%, about 8%, about 7%, about 6%, about 5%, about 4%, about 3%, about 2%, or about 1%, basic species of the antibody.

In some embodiments, the composition or the clarified harvest comprises about 40-70%, about 40-70%, about 40-65%, about 40-60%, about 40-55%, about 40-50%, about 55-75%, about 55-70%, about 60-70%, about 60-65%, or about 60-63% main species of the antibody.

In some embodiments, the composition or the clarified harvest comprises about 30-55% acidic species, about 1-15% basic species, and about 40-75% main species.

In some embodiments, the composition or the clarified harvest comprises about 40-80% isoform B, about 10-30% isoform A/B, and/or about 10-30% isoform A of the antibody.

In some embodiments, the composition or the clarified harvest comprises about 50-75% isoform B, about 15-25% isoform A/B, and/or about 10-25% isoform A of the antibody.

In some embodiments, the composition or the clarified harvest comprises about 45-60% isoform B, about 20-30% isoform A/B, and/or about 15-30% isoform A of the antibody.

In some embodiments, the anti-IL-1R1 antibody or antigen-binding portion thereof, comprises a heavy chain variable region comprising a CDR1 having an amino acid sequence of SEQ ID NO:1, a CDR2 having an amino acid sequence of SEQ ID NO:2, and a CDR3 having an amino acid sequence of SEQ ID NO:3.

In some embodiments, the anti-IL-1R1 antibody, or antigen-binding portion thereof, comprises a light chain variable region comprising a CDR1 having an amino acid sequence of SEQ ID NO:4, a CDR2 having an amino acid sequence of SEQ ID NO:5, and a CDR3 having an amino acid sequence of SEQ ID NO:6.

In some embodiments, the anti-IL-1R1 antibody, or antigen-binding portion thereof, comprises a heavy chain variable region comprising an amino acid sequence of SEQ ID NO:7, and a light chain variable region comprising an amino acid sequence of SEQ ID NO:8.

In some embodiments, the anti-IL-1R1 antibody, or antigen-binding portion thereof, comprises a heavy chain comprising an amino acid sequence of SEQ ID NO:9, and a light chain comprising an amino acid sequence of SEQ ID NO:10.

In some embodiments, the anti-IL-1R1 antibody, or antigen-binding portion thereof, is KPL-387.

In some embodiments, the cell culture is a fed-batch culture.

DETAILED DESCRIPTION OF THE INVENTION

Figure 1:
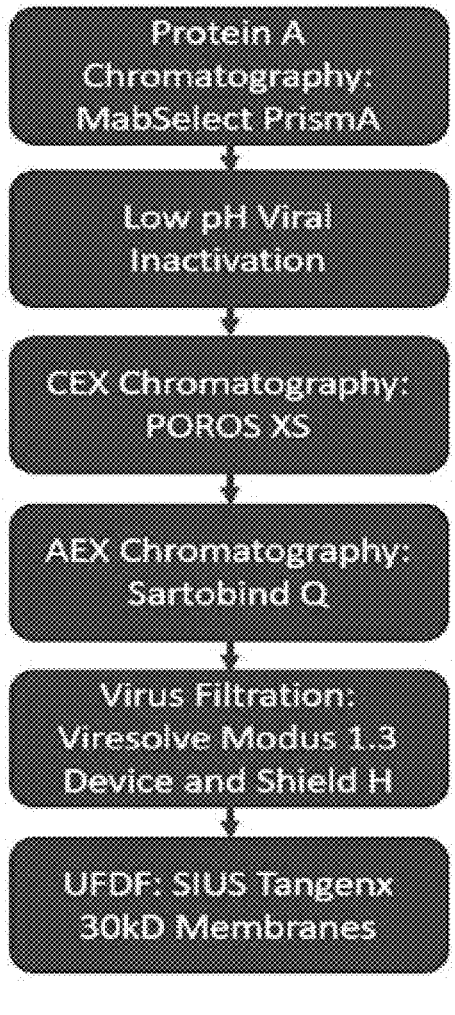
FIG. 1 depicts an overview of an exemplary purification process.

The present disclosure is based on the identification and optimization of the upstream and downstream process technologies for production of antibodies or antigen-binding portions thereof, for example, an anti-IL-1R1 antibody, such as KPL-387, or antigen-binding portions thereof, resulting in compositions having a consistently low level of variants and/or impurities, e.g., a consistently low level of product-related substances, e.g., product aggregates, or charged species, e.g., acidic species, and/or a low level of process-related impurities. Compositions with such a consistently low level of variants, e.g., acidic species and/or aggregates, are highly desirable since the resulting protein product would provide therapeutic benefits with higher potency, higher efficacy, or better stability without undesired effect. Indeed, the present inventors have identified that samples of KPL-387 with a higher level of acidic species unpredictably exhibit a lower potency as determined by the ELISA binding assay. Moreover, a higher level of acidic species in a sample of KPL-387 drug product at baseline was found to correlate with an increase in the amount of higher molecular weight aggregates of KPL-387 formed over time.

The following description is presented to enable a person of ordinary skill in the art to make and use the various embodiments. Descriptions of specific methods, compositions, techniques, and applications are provided only as examples. Various modifications to the examples described herein will be readily apparent to those of ordinary skill in the art, and the general principles described herein may be applied to other examples and applications without departing from the spirit and scope of the various embodiments. Thus, the various embodiments are not intended to be limited to the examples described herein and shown, but are to be accorded the scope consistent with the claims.

Unless defined otherwise, all technical and scientific terms used herein have the same meaning as is commonly understood by one of ordinary skill in the art to which this application belongs. If a definition set forth in this section is contrary to or otherwise inconsistent with a definition set forth in the patents, applications, published applications and other publications that are herein incorporated by reference, the definition set forth in this section prevails over the definition that is incorporated herein by reference. The headings provided herein are for convenience only and do not limit the application in any way. All patents, applications, published applications and other publications referred to herein are incorporated by reference in their entirety.

A. Definitions

In order that the present invention may be more readily understood, certain terms are first defined. In addition, it should be noted that whenever a value or range of values of a parameter are recited, it is intended that values and ranges intermediate to the recited values are also intended to be part of this invention.

The articles "a" and "an" are used herein to refer to one or to more than one (i.e., to at least one) of the grammatical object of the article. By way of example, "an element" means one element or more than one element, e.g., a plurality of elements.

The term "including" is used herein to mean, and is used interchangeably with, the phrase "including but not limited to".

The term "or" is used herein to mean, and is used interchangeably with, the term "and/or," unless context clearly indicates otherwise. For example, "acidic species or basic species" is understood as "acidic species, or basic species, or acidic species and basic species."

The term "about" is used herein to mean within the typical ranges of tolerances in the art. For example, "about" can be understood as about 2 standard deviations from the mean. In certain embodiments, about means ±10%. In certain embodiments, about means ±5%. When about is present before a series of numbers or a range, it is understood that "about" can modify each of the numbers in the series or range.

The terms "polypeptide" and "protein" are used interchangeably to refer to a polymer of amino acid residues, and are not limited to a minimum length. Such polymers of amino acid residues may contain natural or non-natural amino acid residues, and include, but are not limited to, peptides, oligopeptides, dimers, trimers, and multimers of amino acid residues. Both full-length proteins and fragments thereof are encompassed by the definition. The terms also include post-expression modifications of the polypeptide, for example, glycosylation, sialylation, acetylation, phosphorylation, and the like. Furthermore, for purposes of the present invention, a "polypeptide" refers to a protein that includes modifications, such as deletions, additions, and substitutions (generally conservative in nature), to a native sequence, as long as the protein maintains the desired activity. These modifications may be deliberate, as through site-directed mutagenesis, or may be accidental, such as through mutations of hosts that produce the proteins or errors due to PCR amplification.

The term "antibody" includes an immunoglobulin molecule comprised of four polypeptide chains, two heavy (H) chains and two light (L) chains inter-connected by disulfide bonds. Each heavy chain is comprised of a heavy chain variable region (abbreviated herein as HCVR or VH) and a heavy chain constant region (CH). The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDRs), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4.

The term antibody also includes chimeric antibodies, humanized antibodies, and antibodies of various species such as mouse, human, cynomolgus monkey, llama, camel, etc. The term also includes multivalent antibodies such as bivalent or tetravalent antibodies. A multivalent antibody includes, e.g., a single polypeptide chain comprising multiple antigen binding (CDR-containing) domains, as well as two or more polypeptide chains, each containing one or more antigen binding domains, such two or more polypeptide chains being associated with one another, e.g., through a hinge region capable of forming disulfide bond(s) or any other covalent or noncovalent interaction.

The term "antigen-binding portion" of an antibody (or "antibody portion") includes fragments of an antibody, e.g., one or more antigen-binding domains, that retain the ability to specifically bind to an antigen (e.g., in the case of KPL-387, Interleukin 1, Receptor Type 1 (IL-1R1)). It has been shown that the antigen-binding function of an antibody can be performed by fragments of a full-length antibody. Examples of binding fragments encompassed within the term "antigen-binding portion" of an antibody include molecules comprising at least CDR1, CDR2, and CDR3 of a single domain antibody (sdAb), wherein the molecule is capable of binding to an antigen. The term antibody-binding portion also refers to molecules comprising at least CDR1, CDR2, and CDR3 of a heavy chain and CDR1, CDR2, and CDR3 of a light chain, wherein the molecule is capable of binding to an antigen. The term antibody-binding portion also includes fragments that are capable of binding an antigen, such as (i) a Fab fragment, a monovalent fragment comprising the VL, VH, CL and CH1 domains; (ii) a F(ab')2 fragment, a bivalent fragment comprising two Fab fragments linked by a disulfide bridge at the hinge region; (iii) a Fab' fragment, which can be formed by the reduction of F(ab')2 fragment; (iv) a Fc fragment comprising the CH2 and CH3 region and part of the hinge region held together by one or more disulfides and noncovalent interactions; (v) a Fd fragment comprising the VH and CH1 domains; (vi) a Fv fragment comprising the VL and VH domains of a single arm of an antibody, (vii) a reduced IgG or half IgG; and (viii) a dAb fragment (Ward et al., (1989) Nature 341:544-546, the entire teaching of which is incorporated herein by reference), which comprises a VH domain. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see, e.g., Bird et al. (1988) Science 242:423-426; and Huston et al. (1988) Proc. Natl. Acad. Sci. USA 85:5879-5883, the entire teachings of which are incorporated herein by reference). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see, e.g., Holliger, P., et al. (1993) Proc. Natl. Acad. Sci. USA 90:6444-6448; Poljak, R. J., et al. (1994) Structure 2:1121-1123, the entire teachings of which are incorporated herein by reference). Still further, an antibody or antigen-binding portion thereof may be part of a larger immunoadhesion molecule, formed by covalent or non-covalent association of the antibody or antibody portion with one or more other proteins or peptides. Examples of such immunoadhesion molecules include use of the streptavidin core region to make a tetrameric scFv molecule (Kipriyanov, S. M., et al. (1995) Human Antibodies and Hybridomas 6:93-101, the entire teaching of which is incorporated herein by reference) and use of a cysteine residue, a marker peptide and a C-terminal polyhistidine tag to make bivalent and biotinylated scFv molecules (Kipriyanov, S. M., et al. (1994) Mol. Immunol. 31:1047-1058, the entire teaching of which is incorporated herein by reference). Antibody portions, such as Fab and F(ab')2 fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein. In one aspect, the antigen binding portions are complete domains or pairs of complete domains.

The term "human antibody" includes antibodies having variable and constant regions corresponding to human germline immunoglobulin sequences as described by Kabat et al. (See Kabat, et al. (1991) Sequences of proteins of Immunological Interest, Fifth Edition, U.S. Department of Health and Human Services, NIH Publication No. 91-3242). The human antibodies of the invention may include amino acid residues not encoded by human germline immunoglobulin sequences (e.g., mutations introduced by random or site-specific mutagenesis in vitro or by somatic mutation in vivo), e.g., in the CDRs and in particular CDR3. The mutations can be introduced using the "selective mutagenesis approach." The human antibody can have at least one position replaced with an amino acid residue, e.g., an activity enhancing amino acid residue which is not encoded by the human germline immunoglobulin sequence. The human antibody can have up to twenty positions replaced with amino acid residues which are not part of the human germline immunoglobulin sequence. In other embodiments, up to ten, up to five, up to three or up to two positions are replaced. In one embodiment, these replacements are within the CDR regions. However, the term "human antibody", as used herein, is not intended to include antibodies in which CDR sequences derived from the germline of another mammalian species, such as a mouse, have been grafted onto human framework sequences.

The phrase "recombinant human antibody" includes human antibodies that are prepared, expressed, created or isolated by recombinant means, such as antibodies expressed using a recombinant expression vector transfected into a host cell, antibodies isolated from a recombinant, combinatorial human antibody library, antibodies isolated from an animal (e.g., a mouse) that is transgenic for human immunoglobulin genes (see, e.g., Taylor, L. D., et al. (1992) Nucl. Acids Res. 20:6287-6295, the entire teaching of which is incorporated herein by reference) or antibodies prepared, expressed, created or isolated by any other means that involves splicing of human immunoglobulin gene sequences to other DNA sequences. Such recombinant human antibodies have variable and constant regions derived from human germline immunoglobulin sequences (see, Kabat, E. A., et al. (1991) Sequences of Proteins of Immunological Interest, Fifth Edition, U.S. Department of Health and Human Services, NIH Publication No. 91-3242). In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo. In certain embodiments, however, such recombinant antibodies are the result of selective mutagenesis approach or back-mutation or both.

An "isolated antibody", as used herein, refers to an antibody that is substantially free of other antibodies having different antigenic specificities (e.g., an isolated antibody that specifically binds IL-1R1 is substantially free of antibodies that specifically bind antigens other than IL-1R1). An isolated antibody that specifically binds IL-1R1 may, however, have cross-reactivity to other antigens, such as IL-1R1 molecules from other species. Moreover, an isolated antibody may be substantially free of other cellular material and/or chemicals. A suitable anti-IL-1R1 antibody is KPL-387.

The terms "Kabat numbering" "Kabat definitions" and "Kabat labeling" are used interchangeably herein. These terms, which are recognized in the art, refer to a system of numbering amino acid residues which are more variable (i.e., hypervariable) than other amino acid residues in the heavy and light chain variable regions of an antibody, or an antigen binding portion thereof (Kabat et al. (1971) Ann. NY Acad, Sci. 190:382-391 and, Kabat, E. A., et al. (1991) Sequences of Proteins of Immunological Interest, Fifth Edition, U.S. Department of Health and Human Services, NIH Publication No. 91-3242, the entire teachings of which are incorporated herein by reference). For the heavy chain variable region, the hypervariable region ranges from amino acid positions 31 to 35 for CDR1, amino acid positions 50 to 65 for CDR2, and amino acid positions 95 to 102 for CDR3. For the light chain variable region, the hypervariable region ranges from amino acid positions 24 to 34 for CDR1, amino acid positions 50 to 56 for CDR2, and amino acid positions 89 to 97 for CDR3.

The term "product", as used herein refers to a protein of interest, which may be present in the context of a sample comprising one or more variants and/or impurities, e.g., product-related substances, e.g., product aggregates, fragments or charged species, e.g., acidic or basic species, and/or process-related impurities, e.g., host cell proteins. In certain embodiments, the product, i.e., the protein of interest, is an antibody or antigen binding fragment thereof.

The terms "product-related substances" or "product-related variants" refer to any variants of the product, for example, charged species, aggregates, fragments or any other protein product species derived from alternative post-translational modifications. Removal of product-related substances, e.g. protein aggregates, fragments or charged species, e.g., acidic species or basic species, from the resulting protein product, e.g., an antibody or antigen-binding portion thereof, are desirable such that the resulting protein product would provide therapeutic benefits with higher potency, higher efficacy, or better stability without undesired effect.

The term "fragments" as used herein refers to any truncated protein species from the protein of interest due to disruption of one or more bonds along the peptide backbone of a protein of interest, or dissociation of enzymatic and/or chemical modifications. For instance, antibody fragments include, but not limited to, Fab, F(ab')2, Fab', Fc, Fv, scFv, Fd, dAb, half antibody, or other compositions that contain a portion of the antibody molecule.

The terms "aggregates" or "high molecular weight aggregates" or "high molecular weight impurities", as used herein, refer to the oligomerization of two or more individual molecules of protein of interest, including but not limiting to, protein dimers, trimers, tetramers, oligomers and other high molecular weight species.

The terms "charge variants" or "charged species", as used herein, refer to the full complement of product with different charges. In certain embodiments, such variants can include product aggregates and/or product fragments, to the extent that such aggregation and/or fragmentation results in a product with charge variations as seen in an analytical technique used for that purpose. In certain embodiments, such variants refer to products with different modifications that give rise to charge heterogeneity. In monoclonal antibody preparations, charged variants, e.g., acidic species, or basic species, can be detected by charged based separation techniques such as isoelectric focusing (IEF) gel electrophoresis, capillary isoelectric focusing (cIEF) gel electrophoresis, cation exchange chromatography (CEX) and anion exchange chromatography (AEX).

As used herein, the term "acidic species" refers to the variants of a protein, e.g., an antibody or antigen-binding portion thereof, which are characterized by an overall acidic charge relative to the main species. Acidic species are variants with lower apparent pI relative to the main species when antibodies are analyzed using IEF based methods. When analyzed by chromatography-based methods, acidic species and basic species are defined based on their retention times relative to the main peak. Acidic species are the variants that elute earlier than the main peak from CEX or later then than the main peak from AEX.

Acidic species of an antibody may include charge variants, structure variants, and/or fragmentation variants. Exemplary charge variants include, but are not limited to, deamidation variants, afucosylation variants, methylglyoxal variants, glycation variants, and citric acid variants. Exemplary structure variants include, but are not limited to, glycosylation variants and acetonation variants. Exemplary fragmentation variants include any truncated protein species from the protein of interest due to dissociation of peptide chain, enzymatic and/or chemical modifications, including, but not limited to, Fc and Fab fragments, fragments missing a Fab, fragments missing a heavy chain variable domain, C-terminal truncation variants, variants with excision of N-terminal Asp in the light chain, and variants having N-terminal truncation of the light chain. Other acidic species variants also include variants containing unpaired disulfides, host cell proteins, and host nucleic acids, chromatographic materials, and media components.

The acidic species may be the result of product preparation (referred to herein as "preparation-derived acidic species"), or the result of storage (referred to herein as "storage-derived acidic species"). Preparation-derived acidic species are acidic species that are formed during the preparation (upstream and/or downstream processing) of the protein, e.g., the antibody or antigen-binding portion thereof. For example, preparation-derived acidic species can be formed during cell culture ("cell culture-derived acidic species") or during purification of the protein ("purification-derived acidic species"). Storage-derived acidic species and purification-derived acidic species are acidic species that may or may not be present in the population of proteins directly after preparation, but are formed or generated while the sample is being stored or purified, respectively. The type and amount of storage-derived acidic species and purification-derived acidic species can vary based on the conditions to which the sample is subjected. Formation of storage-derived acidic species can be partially or completely inhibited when the preparation is stored under particular conditions. For example, an aqueous formulation can be stored at a particular temperature to partially or completely inhibit acidic species formation. For example, formation or storage-derived acidic species can be partially inhibited in an aqueous formulation stored at between about 2° C. and 8° C., and completely inhibited when stored at −80° C. Moreover, process parameters such as operating conditions and procedures can affect the quality and quantity of charge variants (e.g., purification-dervied acidic species), and impurities (e.g., high molecular weight aggregates) in both product intermediates and purified product. In addition, a low acidic species composition can be lyophilized or freeze-dried to partially or completely inhibit the formation of storage-derived acidic species.

The term "basic species", as used herein, refers to the variants of a protein, e.g., an antibody or antigen-binding portion thereof, which are characterized by an overall basic charge relative to the main species. Basic species are variants with higher apparent pI relative to the main species when antibodies are analyzed using IEF based methods. When analyzed by chromatography-based methods, basic species are the variants that elute later than the main peak from CEX or earlier than the main peak from AEX.

Basic species of an antibody may include charge variants, structure variants, and/or fragmentation variants. Exemplary modifications that result in generation of basic species include, but are not limited to, C-terminal lysine, N-terminal glutamine, isomerization of aspartate, succinimide, methionine oxidation, amidation, incomplete disulfide bonds, incomplete removal of leader sequence, mutation from serine to arginine, aglycosylation, fragments or aggregates. In some embodiments, the basic species refers to an antibody or antigen binding portion thereof comprising a heavy chain having one or two C-terminal lysines.

The term "main species" as used herein, refers to the form of a protein, e.g., an antibody or antigen binding portion thereof, that elutes as the major peak on chromatograms, i.e., the majority species detected during fractionation of charged variants of a protein.

The term "process-related impurity," as used herein, refers to impurities that are present in a composition comprising a protein but are not derived from the protein itself. Process-related impurities include, but are not limited to, host cell proteins (HCPs), host cell nucleic acids, e.g., DNA or RNA, chromatographic materials, and media components. Removal of process-related impurities, such host cell proteins, from the resulting protein product, e.g., an antibody or antigen-binding portion thereof, are desirable such that the resulting protein product would provide therapeutic benefits with higher potency, higher efficacy, or better stability without undesired effect.

The term "host cell proteins" (HCPs), as used herein, is intended to refer to non-target protein-related, proteinaceous impurities derived from host cells.

As used herein, the terms "Interleukin 1, Receptor Type 1" or "IL-1R1" refer to a cytokine receptor that belongs to the interleukin-1 receptor family. IL-1R1 is also known as CD121 Antigen-Like Family Member A, CD121A, CD121a Antigen, IL1RA, D2S1473, P80, EC 3.2.2.6, or CRMO3. IL-1R1 is a receptor for interleukin-1 alpha (IL1α), interleukin-1 beta (IL1β), and interleukin-1 receptor antagonist (IL1Ra). It is an important mediator involved in many cytokine-induced immune and inflammatory responses. Upon binding of a cytokine, e.g., IL1α and IL-1β, to IL-1R1, a shared co-receptor, IL-1RAcP, is recruited by binding to the composite surface of the cytokine and primary receptor complex, resulting in the creation of a trimeric signaling complex. In the resting state, IL-1R1 and the co-acceptor, IL-1RAcP, are present on the cell membrane. Once IL-1 (either IL-1α or IL-1β) binds to IL-1R1, a structural change occurs that allows IL-1RAcP to bind to IL-1R1. The trimeric complex allows for the approximation of the TIR domains of each receptor chain. MyD88 then binds to the TIR domains. The binding of MyD88 triggers a cascade of kinases that produce a strong pro-inflammatory signal leading to activation of NFκB (see PCT Publication No. WO2004022718, the entire contents of which, including the sequences described therein, are incorporated herein by reference).

The term "IL-1R1" includes human IL-1R1, the amino acid sequence of which may be found in for example, GenBank Accession No. NP_000868.1 (SEQ ID NO:11). The term "IL-1R1" also includes cynomolgus IL-1R1, mouse IL-1R1, and rat IL-1R1. The term "IL-1R1" includes a wild type, a variant or an isoform of IL-1R1 protein or a fragment or domain thereof. In certain embodiments, The IL-1R1 protein may be coupled to a signal peptide sequence, and/or a protein tag.

As used herein, the term "KPL-387" refers to a human IgG2 monoclonal antibody that binds to human IL-1R1. KPL-387 has a molecular weight of 144 kDa. In some embodiments KPL-387 has a pI of about 7.4 to about 7.8 In some embodiments, KPL-387 has a pI of 7.6. KPL-387 inhibits the activity of IL-1α and IL-1β. The antibody is comprised of two light chains and two heavy chains with a single N-linked glycosylation on each heavy chain. KPL-387 comprises a heavy chain comprising the sequence set forth as SEQ ID NO:9, and a light chain comprising the sequence set forth as SEQ ID NO: 10. The heavy chain variable region of KPL-387 comprises the sequence set forth as SEQ ID NO:7, and the light chain variable region of KPL-387 comprises the sequence set forth as SEQ ID NO:8. The heavy chain variable region of KPL-387 comprises a CDR1 having the sequence set forth as SEQ ID NO:1, a CDR2 having the sequence set forth as SEQ ID NO:2, and a CDR3 having the sequence set forth as SEQ ID NO:3. The light chain variable region of KPL-387 comprises a CDR1 having the sequence set forth as SEQ ID NO:4, a CDR2 having the sequence set forth as SEQ ID NO:5 and a CDR3 having the sequence set forth as SEQ ID NO:6.

As used herein, the term "upstream process technology," in the context of protein, e.g., antibody, preparation, refers to activities involving the production and collection of proteins (e.g. antibodies) from cells (e.g., during production of protein of interest from cell cultivation).

As used herein, the term "cell culture" refers to methods for generating and maintaining a population of host cells capable of producing a recombinant protein of interest, as well as the methods and techniques for optimizing the production and collection of the protein of interest. For example, once an expression vector has been incorporated into an appropriate host, the host can be maintained under conditions suitable for expression of the relevant nucleotide coding sequences, and the collection and purification of the desired recombinant protein.

When using the cell culture techniques, the protein of interest can be produced intracellularly, in the periplasmic space, or directly secreted into the medium. In embodiments where the protein of interest is produced intracellularly, the particulate debris, either host cells or lysed cells (e.g., resulting from homogenization) can be removed by a variety of means, including but not limited to, centrifugation or ultrafiltration. Where the protein of interest is secreted into the medium, supernatants from such expression systems can be first concentrated using a commercially available protein concentration filter.

As used herein, the term "downstream process technology" refers to one or more techniques used after the upstream process technologies to purify the protein of interest, e.g., antibody. For example, downstream process technology includes purification of the protein product using, for example, affinity chromatography, including Protein A affinity chromatography, ion exchange chromatography, such as anion or cation exchange chromatography, hydrophobic interaction chromatography, mixed-mode or multi-modal chromatography or displacement chromatography.

The phrase "recombinant host cell" (or simply "host cell") includes a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

As used herein, the term "recombinant protein" refers to a protein produced as the result of the transcription and translation of a gene carried on a recombinant expression vector that has been introduced into a host cell. In certain embodiments, the recombinant protein is an antibody, e.g., a chimeric, humanized, or fully human antibody. In certain embodiments the recombinant protein is an antibody of an isotype selected from group consisting of: IgG (e.g., IgG1, IgG2, IgG3, IgG4), IgM, IgA1, IgA2, IgD, or IgE. In certain embodiments the antibody molecule is a full-length antibody (e.g., an IgG1 or IgG4 immunoglobulin) or alternatively the antibody can be a fragment (e.g., an Fc fragment or a Fab fragment).

As used herein, the term "antibody isoform" refers to the different disulfide isoforms of an antibody, e.g., a human IgG2 antibody. IgG2 antibodies can exist in three isoforms (A, B and the intermediate species A/B), each with a different pattern of disulfide bonds. The nature of the disulfide bonding in the IgG2 subclass has been shown to influence antigen binding activity in vitro (Dillon, T M et al., *J Biol Chem.* 2008 Jun. 6; 283(23):16206-16215).

B. Composition of the Invention

Figure 8:
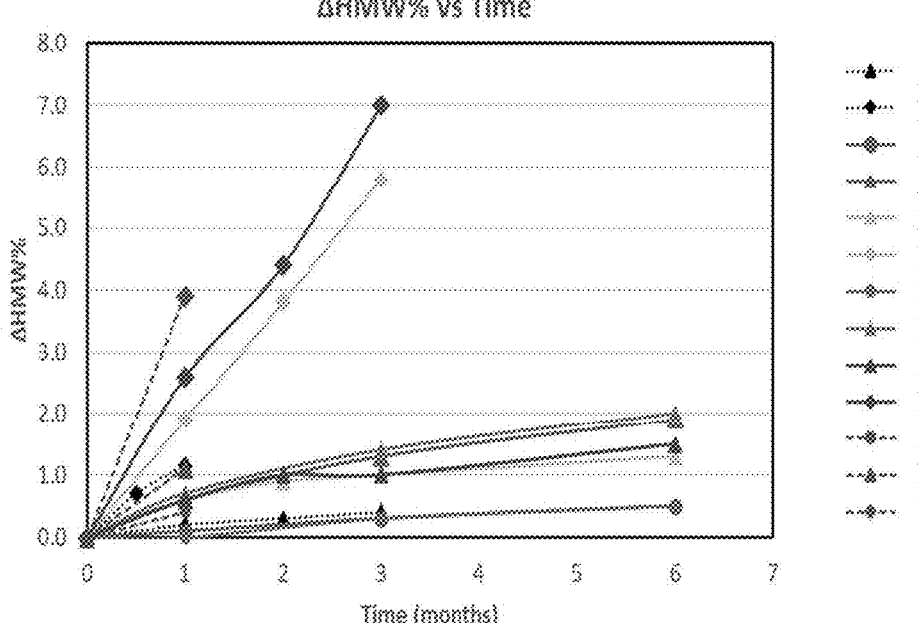
FIG. 8 is a graph depicting the change in the % HMW species of KPL-387 overtime in samples with varying levels of acid species at baseline.
Figure 9:
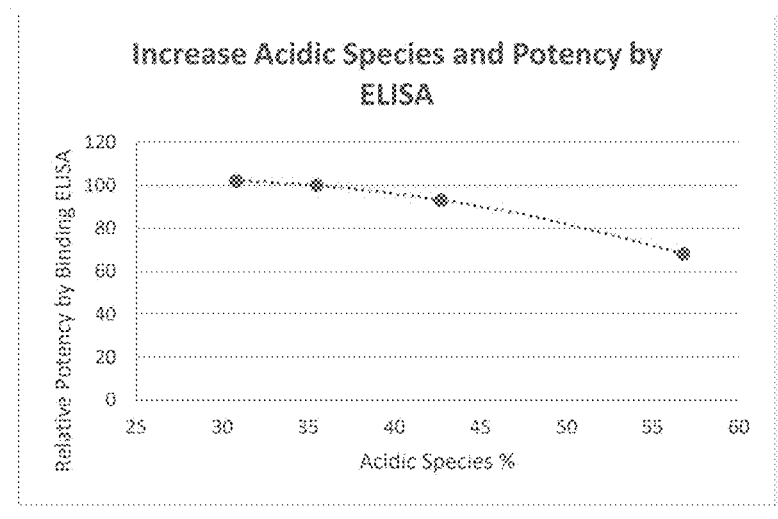
FIG. 9 is a graph depicting the correlation between the acidic species levels and the antibody binding potency as determined by ELISA.

The present invention provides compositions comprising an antibody or antigen-binding portion thereof, for example, an anti-IL-1R1 antibody such as KPL-387. The composition comprises an antibody or antigen-binding portion thereof having a consistently low level of variants and/or impurities, e.g., a consistently low level of product-related substances, e.g., product aggregates, or charged species, e.g., acidic species, and/or a low level of process-related impurities. Such variant/impurity-reduced compositions address the need for improved product characteristics, including, but not limited to, product stability, product safety and product efficacy. It has been found that samples with a higher level of acidic species unpredictably exhibit a lower potency as determined by the ELISA binding assay (FIG. 9). Moreover, a higher level of acidic species in a sample at baseline was found to correlate with an increase in the amount of higher molecular weight aggregates of KPL-387 drug product formed over time (FIG. 8).

In some embodiments, the composition comprises an antibody or antigen-binding portion thereof, for example, an anti-IL-1R1 antibody such as KPL-387, wherein the composition comprises less than about 55%, about 54%, about 53%, about 52%, about 51%, about 50%, about 49%, about 48%, about 47%, about 46%, about 45%, about 44%, about 43%, about 42%, about 41%, about 40%, about 39%, about 38%, about 37%, about 36%, about 35%, about 34%, about 33%, about 32%, about 31%, about 30%, about 29%, about 28%, about 27%, about 26%, about 25%, about 24%, about 23%, about 22%, about 21%, about 20%, about 19%, about 18%, about 17%, about 16%, about 15%, about 14%, about 13%, about 12%, about 11%, or about 10% acidic species of the antibody, and ranges within one or more of the preceding. In some embodiments, the composition comprises less than about 55% acidic species. In some embodiments, the composition comprises less than about 40% acidic species. In another embodiment, the composition comprises less than 39% acidic species. In another embodiment, the composition comprises less than 38% acidic species. In another embodiment, the composition comprises less than 37% acidic species. In another embodiment, the composition comprises less than 36% acidic species. In another embodiment, the composition comprises less than 35% acidic species.

In some embodiments, the composition comprises an antibody or antigen-binding portion thereof, for example, an anti-IL-1R1 antibody such as KPL-387, wherein the composition comprises about 30-55%, about 31-55%, about 32-55%, about 33-55%, about 34-55%, about 35-55%, about 30-40%, about 31-40%, about 32-40%, about 33-40%, about 34-40%, about 35-40%, about 31-39%, about 31-38%, about 31-37%, about 31-36%, about 32-39%, about 32-38%, about 32-37%, about 32-36%, about 33-39%, about 33-38%, about 33-37%, about 33-36%, about 34-39%, about 34-38%, about 34-37%, or about 34-36% of the acidic species, and ranges within one or more of the preceding. In some embodiments, the composition comprises about 30-55% acidic species. In some embodiments, the composition comprises about 30-45% acidic species. In some embodiments, the composition comprises about 30-40% acidic species. In some embodiments, the composition comprises about 34-36% acidic species.

In some embodiments, the composition comprises an antibody or antigen-binding portion thereof, for example, an anti-IL-1R1 antibody such as KPL-387, wherein the composition comprises less than about 15%, about 14%, about 13%, about 12%, about 11%, about 10%, about 9%, about 8%, about 7%, about 6%, about 5%, about 4%, about 3%, about 2%, or about 1% of the basic species, and ranges within one or more of the preceding. In some embodiments, the composition comprises less than about 15% basic species. In some embodiments, the composition comprises less than about 10% basic species. In some embodiments, the composition comprises less than about 5% basic species. In some embodiments, the composition comprises less than about 4% basic species. In some embodiments, the composition comprises less than about 3% basic species. In some embodiments, the composition comprises less than about 2% basic species.

In some embodiments, the composition comprises an antibody or antigen-binding portion thereof, for example, an anti-IL-1R1 antibody such as KPL-387, wherein the composition comprises about 0.1-10%, about 0.1-9%, about 0.1-8%, about 0.1-7%, about 0.1-6%, about 0.1-5%, about 0.1-4%, about 0.1-3%, about 0.1-2%, about 1-15%, about 1-14%, about 1-13%, about 1-12%, about 1-11%, about 1-10%, about 1-9%, about 1-8%, about 1-7%, about 1-6%, about 1-5%, about 2-5%, about 2-4%, about 1-4%, about 1-3%, or about 1-2% of the basic species, and ranges within one or more of the preceding. In some embodiments, the composition comprises about 0.1-10% basic species. In some embodiments, the composition comprises about 1-5% basic species. In some embodiments, the composition comprises about 1-15% basic species. In some embodiments, the composition comprises about 1-10% basic species. In some embodiments, the composition comprises about 2-4% basic species. In some embodiments, the composition comprises about 1-4% basic species.

In some embodiments, the composition comprises an antibody or antigen-binding portion thereof, for example, an anti-IL-1R1 antibody such as KPL-387, wherein the composition comprises more than about 40%, e.g., about 41%, about 42%, about 43%, about 44%, about 45%, about 46%, about 47%, about 48%, about 49%, about 50%, about 55%, about 60%, about 61%, about 62%, about 63%, about 64%, about 65%, about 66%, about 67%, about 68%, about 69%, about 70%, about 75%, about 80%, about 85%, about 90%, about 95% or about 99% main species of the antibody, and ranges within one or more of the preceding. In a particular embodiment, the composition comprises more than 40% main species. In a particular embodiment, the composition comprises more than 45% main species. In a particular embodiment, the composition comprises more than 55% main species. In a particular embodiment, the composition comprises more than 56% main species. In a particular embodiment, the composition comprises more than 57% main species. In a particular embodiment, the composition comprises more than 58% main species. In a particular embodiment, the composition comprises more than 59% main species. In another embodiment, the composition comprises more than 60% main species. In another embodiment, the composition comprises more than 61% main species. In another embodiment, the composition comprises more than 62% main species.

In some embodiments, the composition comprises an antibody or antigen-binding portion thereof, for example, an anti-IL-1R1 antibody such as KPL-387, wherein the composition comprises about 40-70%, about 40-70%, about 40-65%, about 40-60%, about 40-55%, about 40-50%, about 55-95%, about 55-85%, about 55-75%, about 55-70%, about 60-70%, about 60-65%, or about 60-63% main species of the antibody, and ranges within one or more of the preceding. In some embodiments, the composition comprises about 40-75% main species. In some embodiments, the composition comprises about 55-75% main species. In some embodiments, the composition comprises about 60-63% main species.

In some embodiments, the composition comprises about 30-55% acidic species, about 1-15% basic species, and about 40-75% main species.

In some embodiments, the composition comprises about 30-40% acidic species, about 1-5% basic species, and/or about 55-75% main species.

In some embodiments, the composition comprises about 34-36% acidic species, about 1-5% basic species, and/or about 60-63% main species.

In some embodiments, the level of acidic species, the level of main species, or the level of basic species is determined by Imaging Capillary Isoelectric Focusing (iCIEF).

In some embodiments, the composition comprising an antibody or antigen-binding portion thereof, for example, an anti-IL-1R1 antibody such as KPL-387, wherein the composition comprises less than about 10%, about 9%, about 8%, about 7%, about 6%, about 5%, about 4%, about 3%, about 2.5%, about 2%, or about 1% high molecular weight aggregates, and ranges within one or more of the preceding. In some embodiments, the composition comprises less than about 4% high molecular weight aggregates. In some embodiments, the composition comprises less than about 3% high molecular weight aggregates. In some embodiments, the composition comprises less than about 2% high molecular weight aggregates. In some embodiments, the composition comprises less than about 4% high molecular weight aggregates, and less than about 100 ppm of host cell proteins (HCP). In some embodiments, the composition comprises less than about 4% high molecular weight aggregates, less than about 100 ppm of host cell proteins (HCP), and less than about 1.6 ppm Protein A (ProA). In some embodiments, the composition comprising an antibody or antigen-binding portion thereof, for example, an anti-IL-1R1 antibody such as KPL-387, wherein the composition comprises about 1-10%, about 1-9%, about 1-8%, about 1-7%, about 1-6%, about 1-5%, about 1-4%, about 1-13.5%, about 1-3%, about 1-2.5%, or about 1-2% high molecular weight aggregates, and ranges within one or more of the preceding. In some embodiments, the composition comprises about 1-10% high molecular weight aggregates. In some embodiments, the composition comprises about 1-3.5% high molecular weight aggregates. In some embodiments, the composition comprises about 1-3% high molecular weight aggregates. In some embodiments, the composition comprises about 1-2% high molecular weight aggregates. In some embodiments, the composition comprises about 1-3% high molecular weight aggregates, and less than about 100 ppm of host cell proteins (HCP). In some embodiments, the composition comprises about 1-3% high molecular weight aggregates, less than about 100 ppm of host cell proteins (HCP), and less than about 1.6 ppm Protein A (ProA).

In some embodiments, the composition comprising an antibody or antigen-binding portion thereof, for example, an anti-IL-1R1 antibody such as KPL-387, wherein the composition comprises more than about 90%, about 91%, about 92%, about 93%, about 94%, about 95%, about 96%, about 97%, about 98%, or about 99% antibody monomer. In some embodiments, the composition comprises more than about 96% antibody monomer. In some embodiments, the composition comprises more than about 97% antibody monomer. In some embodiments, the composition comprises more than about 98% antibody monomer. In some embodiments, the composition comprises more than about 99% antibody monomer. In some embodiments, the composition comprises more than about 96% antibody monomer, and less than about 100 ppm of host cell proteins (HCP). In some embodiments, the composition comprises more than about 96% antibody monomer, less than about 100 ppm of host cell proteins (HCP), and less than about 1.6 ppm Protein A (ProA). In some embodiments, the composition comprising an antibody or antigen-binding portion thereof, for example, an anti-IL-1R1 antibody such as KPL-387, wherein the composition comprises about 90-99.9%, about 90-99%, about 95-99%, about 96-99%, about 96.5-99%, about 97-99%, or about 98-99% antibody monomer, and ranges within one or more of the preceding. In some embodiments, the composition comprises about 90-99% antibody monomer. In some embodiments, the composition comprises about 96.5-99% antibody monomer. In some embodiments, the composition comprises about 97-99% antibody monomer. In some embodiments, the composition comprises about 97-99% antibody monomer, and less than about 100 ppm of host cell proteins (HCP). In some embodiments, the composition comprises about 97-99% antibody monomer, less than about 100 ppm of host cell proteins (HCP), and less than about 1.6 ppm Protein A (ProA).

In some embodiments, the level of high molecular weight aggregates, or the level of antibody monomer are determined by size exclusion chromatography.

In some embodiments, the composition comprises an antibody or antigen-binding portion thereof, for example, an anti-IL-1R1 antibody such as KPL-387, wherein the composition comprises more than about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, or about 80% isoform B of the antibody, and ranges within one or more of the preceding. In some embodiments, the composition comprises more than about 40% isoform B of the antibody. In another embodiment, the composition comprises more than about 45% isoform B of the antibody. In another embodiment, the composition comprises more than about 50% isoform B of the antibody. In another embodiment, the composition comprises more than about 55% isoform B of the antibody. In another embodiment, the composition comprises more than about 60% isoform B of the antibody. In another embodiment, the composition comprises more than about 65% isoform B of the antibody. In another embodiment, the composition comprises more than about 70% isoform B of the antibody.

In some embodiments, the composition comprises less than about 40% isoform B of the antibody. In another embodiment, the composition comprises less than about 45% isoform B of the antibody. In another embodiment, the composition comprises less than about 50% isoform B of the antibody. In another embodiment, the composition comprises less than about 55% isoform B of the antibody. In another embodiment, the composition comprises less than about 60% isoform B of the antibody. In another embodiment, the composition comprises less than about 65% isoform B of the antibody. In another embodiment, the composition comprises less than about 70% isoform B of the antibody.

In some embodiments, the composition comprises an antibody or antigen-binding portion thereof, for example, an anti-IL-1R1 antibody such as KPL-387, wherein the composition comprises about 40-80%, about 45-80%, about 45-75%, about 45-70%, about 45-65%, about 45-60%, about 50-80%, about 50-75%, about 50-70%, about 50-65%, or about 55-70% isoform B of the antibody, and ranges within one or more of the preceding. In some embodiments, the composition comprises about 40-80% isoform B. In some embodiments, the composition comprises about 45-60% isoform B. In some embodiments, the composition comprises about 50-70% isoform B. In some embodiments, the composition comprises about 50-75% isoform B.

In some embodiments, the composition comprises an antibody or antigen-binding portion thereof, for example, an anti-IL-1R1 antibody such as KPL-387, wherein the composition comprises less than about 30%, about 29%, about 28%, about 27%, about 26%, about 25%, about 24%, about 23%, about 22%, about 21%, about 20%, about 19%, about 18%, about 17%, about 16%, about 15%, about 14%, about 13%, about 12%, about 11%, or about 10% isoform A/B of the antibody, and ranges within one or more of the preceding. In some embodiments, the composition comprises less than about 30% isoform A/B of the antibody. In another embodiment, the composition comprises less than about 25% isoform A/B of the antibody. In another embodiment, the composition comprises less than about 20% isoform A/B of the antibody. In another embodiment, the composition comprises less than about 15% isoform A/B of the antibody.

In some embodiments, the composition comprises an antibody or antigen-binding portion thereof, for example, an anti-IL-1R1 antibody such as KPL-387, wherein the composition comprises about 10-30%, about 15-30%, about 20-30%, about 10-25%, or about 15-25% isoform A/B of the antibody, and ranges within one or more of the preceding. In some embodiments, the composition comprises about 10-30% isoform A/B. In some embodiments, the composition comprises about 20-30% isoform A/B. In some embodiments, the composition comprises about 15-25% isoform A/B.

In some embodiments, the composition comprises an antibody or antigen-binding portion thereof, for example, an anti-IL-1R1 antibody such as KPL-387, wherein the composition comprises less than about 30%, about 29%, about 28%, about 27%, about 26%, about 25%, about 24%, about 23%, about 22%, about 21%, about 20%, about 19%, about 18%, about 17%, about 16%, about 15%, about 14%, about 13%, about 12%, about 11%, or about 10% isoform A of the antibody, and ranges within one or more of the preceding. In some embodiments, the composition comprises less than about 30% isoform A of the antibody. In another embodiment, the composition comprises less than about 25% isoform A of the antibody. In another embodiment, the composition comprises less than about 20% isoform A of the antibody. In another embodiment, the composition comprises less than about 15% isoform A of the antibody.

In some embodiments, the composition comprises more than about 30% isoform A of the antibody. In another embodiment, the composition comprises more than about 25% isoform A of the antibody. In another embodiment, the composition comprises more than about 20% isoform A of the antibody. In another embodiment, the composition comprises more than about 15% isoform A of the antibody.

In some embodiments, the composition comprises an antibody or antigen-binding portion thereof, for example, an anti-IL-1R1 antibody such as KPL-387, wherein the composition comprises about 10-30%, about 15-30%, about 20-30%, about 10-25%, or about 15-25% isoform A of the antibody, and ranges within one or more of the preceding. In some embodiments, the composition comprises about 10-30% isoform A/B. In some embodiments, the composition comprises about 15-30% isoform A. In some embodiments, the composition comprises about 10-25% isoform A.

In some embodiments, the composition comprises about 40-80% isoform B, about 10-30% isoform A/B, and/or about 10-30% isoform A of the antibody.

In some embodiments, the composition comprises about 50-75% isoform B, about 15-25% isoform A/B, and/or about 10-25% isoform A of the antibody.

In some embodiments, the composition comprises about 45-60% isoform B, about 20-30% isoform A/B, and/or about 15-30% isoform A of the antibody.

In some embodiments, the level of antibody isoforms are determined by reverse phase chromatography.

The compositions of the invention comprises an antibody or antigen binding portion thereof. For example, the antibody, or antigen binding portion thereof, may be an anti-IL-1R1 antibody, or antigen binding portion thereof, such as KPL-387, or an antigen binding portion thereof. In one aspect of this embodiment, the antibody, or antigen binding portion thereof, comprises a heavy chain variable region comprising a CDR1 having the sequence set forth as SEQ ID NO:1, a CDR2 having the sequence set forth as SEQ ID NO:2, and a CDR3 having the sequence set forth as SEQ ID NO:3. In another aspect of this embodiment, the antibody, or antigen binding portion thereof, comprises a light chain variable region comprising a CDR1 having the sequence set forth as SEQ ID NO:4, a CDR2 having the sequence set forth as SEQ ID NO:5 and a CDR3 having the sequence set forth as SEQ ID NO:6. In one aspect of this embodiment, the antibody, or antigen binding portion thereof, comprises a heavy chain variable region comprising the sequence set forth as SEQ ID NO:7, and a light chain variable region comprising the sequence set forth as SEQ ID NO:8. In one aspect of this embodiment, the antibody, or antigen binding portion thereof, comprises a heavy chain comprising the sequence set forth as SEQ ID NO:9, and a light chain comprising the sequence set forth as SEQ ID NO:10.

Eluate Fraction

In some embodiments, the compositions of the invention comprise an eluate fraction comprising an anti-IL-1R1 antibody, or antigen-binding portion thereof, wherein the eluate fraction is collected from a cation exchange chromatography resin.

In some embodiments, the eluate fraction comprising an antibody or antigen-binding portion thereof, for example, an anti-IL-1R1 antibody, such as KPL-387, collected following a cation exchange chromatography step, comprises less than about 55%, about 54%, about 53%, about 52%, about 51%, about 50%, about 49%, about 48%, about 47%, about 46%, about 45%, about 44%, about 43%, about 42%, about 41%, about 40%, about 39%, about 38%, about 37%, about 36%, about 35%, about 34.5%, about 34%, about 33%, about 32%, about 31%, about 30%, about 29%, about 28%, about 27%, about 26%, about 25%, about 24%, about 23%, about 22%, about 21%, about 20%, about 19%, about 18%, about 17%, about 16%, about 15%, about 14%, about 13%, about 12%, about 11%, or about 10% of the acidic species, and ranges within one or more of the preceding. In one embodiment, the eluate fraction comprises less than 55% acidic species. In a particular embodiment, the eluate fraction comprises less than 40% acidic species. In a particular embodiment, the eluate fraction comprises less than 39% acidic species. In a particular embodiment, the eluate fraction comprises less than 38% acidic species. In a particular embodiment, the eluate fraction comprises less than 37% acidic species. In another embodiment, the eluate fraction comprises less than 36% acidic species. In another embodiment, the eluate fraction comprises less than 35% acidic species. In another embodiment, the eluate fraction comprises less than 34.5% acidic species. In another embodiment, the eluate fraction comprises less than 34% acidic species.

In some embodiments, the eluate fraction comprising an antibody or antigen-binding portion thereof, for example, an anti-IL-1R1 antibody, such as KPL-387, collected following a cation exchange chromatography step, comprises about 30-55%, about 31-55%, about 32-55%, about 33-55%, about 34-55%, about 35-55%, about 30-40%, about 31-40%, about 32-40%, about 33-40%, about 34-40%, about 35-40%, about 31-39%, about 31-38%, about 31-37%, about 31-36%, about 32-39%, about 32-38%, about 32-37%, about 32-36%, about 33-39%, about 33-38%, about 33-37%, about 33-36%, about 34-39%, about 34-38%, about 34-37%, or about 34-36% of the acidic species, and ranges within one or more of the preceding. In some embodiments, the eluate fraction comprises about 30-55% acidic species. In some embodiments, the eluate fraction comprises about 30-45% acidic species. In some embodiments, the eluate fraction comprises about 30-40% acidic species. In some embodiments, the eluate fraction comprises about 34-36% acidic species.

In some embodiments, the eluate fraction comprising an antibody or antigen-binding portion thereof, for example, an anti-IL-1R1 antibody, such as KPL-387, collected following a cation exchange chromatography step, comprises less than about 15%, about 14%, about 13%, about 12%, about 11%, about 10%, about 9%, about 8%, about 7%, about 6%, about 5%, about 4.5%, about 4%, about 3%, about 2%, or about 1% of the basic species, and ranges within one or more of the preceding. In some embodiments, the eluate fraction comprises less than about 15% basic species. In some embodiments, the eluate fraction comprises less than about 10% basic species. In some embodiments, the eluate fraction comprises less than about 5% basic species. In some embodiments, the eluate fraction comprises less than about 4% basic species. In some embodiments, the eluate fraction comprises less than about 3% basic species. In some embodiments, the eluate fraction comprises less than about 2% basic species.

In some embodiments, the eluate fraction comprising an antibody or antigen-binding portion thereof, for example, an anti-IL-1R1 antibody, such as KPL-387, collected following a cation exchange chromatography step, comprises about 0.1-10%, about 0.1-9%, about 0.1-8%, about 0.1-7%, about 0.1-6%, about 0.1-5%, about 0.1-4%, about 0.1-3%, about 0.1-2%, about 1-15%, about 1-14%, about 1-13%, about 1-12%, about 1-11%, about 1-10%, about 1-9%, about 1-8%, about 1-7%, about 1-6%, about 1-5%, about 2-5%, about 2-4%, about 4.5-5.5%, about 1-4%, about 1-3%, or about 1-2% of the basic species, and ranges within one or more of the preceding. In some embodiments, the eluate fraction comprises about 0.1-10% basic species. In some embodiments, the eluate fraction comprises about 1-15% basic species. In some embodiments, the eluate fraction comprises about 1-10% basic species. In some embodiments, the eluate fraction comprises about 1-5% basic species. In some embodiments, the eluate fraction comprises about 2-4% basic species. In some embodiments, the eluate fraction comprises about 1-4% basic species.

In some embodiments, the eluate fraction comprising an antibody or antigen-binding portion thereof, for example, an anti-IL-1R1 antibody, such as KPL-387, collected following a cation exchange chromatography step, comprises more than about 40%, e.g., about 41%, about 42%, about 43%, about 44%, about 45%, about 46%, about 47%, about 48%, about 49%, about 50%, about 55%, about 60%, about 61%, about 62%, about 63%, about 64%, about 65%, about 66%, about 67%, about 68%, about 69%, about 70%, about 75%, about 80%, about 85%, about 90%, about 95% or about 99% main species of the antibody, and ranges within one or more of the preceding. In a particular embodiment, the eluate fraction comprises more than 40% main species. In a particular embodiment, the eluate fraction comprises more than 45% main species. In a particular embodiment, the eluate fraction comprises more than 55% main species. In another embodiment, the eluate fraction comprises more than 56% main species. In another embodiment, the eluate fraction comprises more than 57% main species. In another embodiment, the eluate fraction comprises more than 58% main species. In another embodiment, the eluate fraction comprises more than 59% main species. In another embodiment, the eluate fraction comprises more than 60% main species. In another embodiment, the eluate fraction comprises more than 61% main species. In another embodiment, the eluate fraction comprises more than 62% main species.

In some embodiments, the eluate fraction comprising an antibody or antigen-binding portion thereof, for example, an anti-IL-1R1 antibody, such as KPL-387, collected following a cation exchange chromatography step, comprises about 40-70%, about 40-70%, about 40-65%, about 40-60%, about 40-55%, about 40-50%, about 55-95%, about 55-85%, about 55-75%, about 55-70%, about 60-70%, about 60-65%, or about 60-63% main species of the antibody, and ranges within one or more of the preceding. In some embodiments, the eluate fraction comprises about 40-75% main species. In some embodiments, the eluate fraction comprises about 55-75% main species. In some embodiments, the eluate fraction comprises about 60-63% main species.

In some embodiments, the eluate fraction comprising an antibody or antigen-binding portion thereof, for example, an anti-IL-1R1 antibody, such as KPL-387, collected following a cation exchange chromatography step, comprises about 30-55% acidic species, about 1-15% basic species, and/or about 40-75% main species.

In some embodiments, the eluate fraction comprising an antibody or antigen-binding portion thereof, for example, an anti-IL-1R1 antibody, such as KPL-387, collected following a cation exchange chromatography step, comprises about 30-40% acidic species, about 1-5% basic species, and/or about 55-75% main species.

In some embodiments, the eluate fraction comprising an antibody or antigen-binding portion thereof, for example, an anti-IL-1R1 antibody, such as KPL-387, collected following a cation exchange chromatography step, comprises about 34-36% acidic species, about 1-5% basic species, and/or about 60-63% main species.

In some embodiments, the level of acidic species, the level of main species, or the level of basic species is determined by Imaging Capillary Isoelectric Focusing (iCIEF).

In some embodiments, the eluate fraction comprising an antibody or antigen-binding portion thereof, for example, an anti-IL-1R1 antibody, such as KPL-387, collected following a cation exchange chromatography step, comprises less than about 10%, about 9%, about 8%, about 7%, about 6%, about 5%, about 4%, about 3%, about 2.5%, about 2%, or about 1% high molecular weight aggregates, and ranges within one or more of the preceding. In some embodiments, the eluate fraction comprises less than about 4% high molecular weight aggregates. In some embodiments, the eluate fraction comprises less than about 3% high molecular weight aggregates. In some embodiments, the eluate fraction comprises less than about 2% high molecular weight aggregates. In some embodiments, the eluate fraction comprises less than about 4% high molecular weight aggregates and less than about 100 ppm of host cell proteins (HCP), and, optionally, less than about 1.6 ppm Protein A (ProA).

In some embodiments, the eluate fraction comprising an antibody or antigen-binding portion thereof, for example, an anti-IL-1R1 antibody, such as KPL-387, collected following a cation exchange chromatography step, comprises about 1-10%, about 1-9%, about 1-8%, about 1-7%, about 1-6%, about 1-5%, about 1-4%, about 1-3.5%, about 1-3%, about 1-2.5%, or about 1-2% high molecular weight aggregates, and ranges within one or more of the preceding. In some embodiments, the eluate fraction comprises about 1-10% high molecular weight aggregates. In some embodiments, the eluate fraction comprises about 1-3.5% high molecular weight aggregates. In some embodiments, the eluate fraction comprises about 1-3% high molecular weight aggregates. In some embodiments, the eluate fraction comprises about 1-2% high molecular weight aggregates. In some embodiments, the eluate fraction comprises about 1-3% high molecular weight aggregates and less than about 100 ppm of host cell proteins (HCP), and, optionally, less than about 1.6 ppm Protein A (ProA).

In some embodiments, the eluate fraction comprising an antibody or antigen-binding portion thereof, for example, an anti-IL-1R1 antibody, such as KPL-387, collected following a cation exchange chromatography step, comprises more than about 90%, about 91%, about 92%, about 93%, about 94%, about 95%, about 96%, about 97%, about 98%, or about 99% antibody monomer. In some embodiments, the eluate fraction comprises more than about 96% antibody monomer. In some embodiments, the eluate fraction comprises more than about 97% antibody monomer. In some embodiments, the eluate fraction comprises more than about 98% antibody monomer. In some embodiments, the elute fraction comprises more than about 99% antibody monomer. In some embodiments, the eluate fraction comprises more than about 96% antibody monomer and less than about 100 ppm of host cell proteins (HCP), and, optionally, less than about 1.6 ppm Protein A (ProA).

In some embodiments, the eluate fraction comprising an antibody or antigen-binding portion thereof, for example, an anti-IL-1R1 antibody, such as KPL-387, collected following a cation exchange chromatography step, comprises about 90-99.9%, about 90-99%, about 95-99%, about 96-99%, about 96.5-99%, about 97-99%, or about 98-99% antibody monomer, and ranges within one or more of the preceding. In some embodiments, the eluate fraction comprises about 96.5-99% antibody monomer. In some embodiments, the eluate fraction comprises about 90-99% antibody monomer. In some embodiments, the eluate fraction comprises about 97-99% antibody monomer. In some embodiments, the eluate fraction comprises about 97-99% antibody monomer and less than about 100 ppm of host cell proteins (HCP), and, optionally, less than about 1.6 ppm Protein A (ProA).

In some embodiments, the level of high molecular weight aggregates, or the level of antibody monomer are determined by size exclusion chromatography.

In some embodiments, the eluate fraction comprising an antibody or antigen-binding portion thereof, for example, an anti-IL-1R1 antibody, such as KPL-387, collected following a cation exchange chromatography step, comprises more than about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, or about 80% isoform B of the antibody, and ranges within one or more of the preceding.

In some embodiments, the eluate fraction comprises more than about 40% isoform B of the antibody. In another embodiment, the eluate fraction comprises more than about 45% isoform B of the antibody. In another embodiment, the eluate fraction comprises more than about 50% isoform B of the antibody. In another embodiment, the eluate fraction comprises more than about 55% isoform B of the antibody. In another embodiment, the eluate fraction comprises more than about 60% isoform B of the antibody. In another embodiment, the eluate fraction comprises more than about 65% isoform B of the antibody. In another embodiment, the eluate fraction comprises more than about 70% isoform B of the antibody.

In another embodiment, the eluate fraction comprises less than about 50% isoform B of the antibody. In another embodiment, the eluate fraction comprises less than about 55% isoform B of the antibody. In another embodiment, the eluate fraction comprises less than about 60% isoform B of the antibody. In another embodiment, the eluate fraction comprises less than about 65% isoform B of the antibody. In another embodiment, the eluate fraction comprises less than about 70% isoform B of the antibody.

In some embodiments, the eluate fraction comprising an antibody or antigen-binding portion thereof, for example, an anti-IL-1R1 antibody, such as KPL-387, collected following a cation exchange chromatography step, comprises about 40-80%, about 45-80%, about 45-75%, about 45-70%, about 45-65%, about 45-60%, about 50-80%, about 50-75%, about 50-70%, about 50-65%, or about 55-70% isoform B of the antibody, and ranges within one or more of the preceding. In some embodiments, the eluate fraction comprises about 40-80% isoform B. In some embodiments, the eluate fraction comprises about 45-60% isoform B. In some embodiments, the eluate fraction comprises about 50-70% isoform B. In some embodiments, the eluate fraction comprises about 50-75% isoform B.

In some embodiments, the eluate fraction comprising an antibody or antigen-binding portion thereof, for example, an anti-IL-1R1 antibody, such as KPL-387, collected following a cation exchange chromatography step, comprises less than about 30%, about 29%, about 28%, about 27%, about 26%, about 25%, about 24%, about 23%, about 22%, about 21%, about 20%, about 19%, about 18%, about 17%, about 16%, about 15%, about 14%, about 13%, about 12%, about 11%, or about 10% isoform A/B of the antibody, and ranges within one or more of the preceding. In some embodiments, the eluate fraction comprises less than about 30% isoform A/B of the antibody. In another embodiment, the eluate fraction comprises less than about 25% isoform A/B of the antibody. In another embodiment, the eluate fraction comprises less than about 20% isoform A/B of the antibody. In another embodiment, the eluate fraction comprises less than about 15% isoform A/B of the antibody.

In some embodiments, the eluate fraction comprising an antibody or antigen-binding portion thereof, for example, an anti-IL-1R1 antibody, such as KPL-387, collected following a cation exchange chromatography step, comprises about 10-30%, about 15-30%, about 20-30%, about 10-25%, or about 15-25% isoform A/B of the antibody, and ranges within one or more of the preceding. In some embodiments, the eluate fraction comprises about 10-30% isoform A/B. In some embodiments, the eluate fraction comprises about 20-30% isoform A/B. In some embodiments, the eluate fraction comprises about 15-25% isoform A/B.

In some embodiments, the eluate fraction comprising an antibody or antigen-binding portion thereof, for example, an anti-IL-1R1 antibody, such as KPL-387, collected following a cation exchange chromatography step, comprises less than about 30%, about 29%, about 28%, about 27%, about 26%, about 25%, about 24%, about 23%, about 22%, about 21%, about 20%, about 19%, about 18%, about 17%, about 16%, about 15%, about 14%, about 13%, about 12%, about 11%, or about 10% isoform A of the antibody, and ranges within one or more of the preceding. In some embodiments, the eluate fraction comprises less than about 30% isoform A of the antibody. In another embodiment, the eluate fraction comprises less than about 25% isoform A of the antibody. In another embodiment, the eluate fraction comprises less than about 20% isoform A of the antibody. In another embodiment, the eluate fraction comprises less than about 15% isoform A of the antibody.

In some embodiments, the eluate fraction comprising an antibody or antigen-binding portion thereof, for example, an anti-IL-1R1 antibody, such as KPL-387, collected following a cation exchange chromatography step, comprises more than about 30%, about 29%, about 28%, about 27%, about 26%, about 25%, about 24%, about 23%, about 22%, about 21%, about 20%, about 19%, about 18%, about 17%, about 16%, about 15%, about 14%, about 13%, about 12%, about 11%, or about 10% isoform A of the antibody, and ranges within one or more of the preceding.

In some embodiments, the eluate fraction comprising an antibody or antigen-binding portion thereof, for example, an anti-IL-1R1 antibody, such as KPL-387, collected following a cation exchange chromatography step, comprises about 10-30%, about 15-30%, about 20-30%, about 10-25%, or about 15-25% isoform A of the antibody, and ranges within one or more of the preceding. In some embodiments, the eluate fraction comprises about 10-30% isoform A/B. In some embodiments, the eluate fraction comprises about 20-30% isoform A/B. In some embodiments, the eluate fraction comprises about 15-30% isoform A. In some embodiments, the eluate fraction comprises about 10-25% isoform A.

In some embodiments, the eluate fraction comprising an antibody or antigen-binding portion thereof, for example, an anti-IL-1R1 antibody, such as KPL-387, collected following a cation exchange chromatography step, comprises about 40-80% isoform B, about 10-30% isoform A/B, and/or about 10-30% isoform A of the antibody.

In some embodiments, the eluate fraction comprising an antibody or antigen-binding portion thereof, for example, an anti-IL-1R1 antibody, such as KPL-387, collected following a cation exchange chromatography step, comprises about 50-75% isoform B, about 15-25% isoform A/B, and/or about 10-25% isoform A of the antibody.

In some embodiments, the eluate fraction comprising an antibody or antigen-binding portion thereof, for example, an anti-IL-1R1 antibody, such as KPL-387, collected following a cation exchange chromatography step, comprises about 45-60% isoform B, about 20-30% isoform A/B, and/or about 15-30% isoform A of the antibody.

In some embodiments, the level of antibody isoforms are determined by reverse phase chromatography.

Flow-Through Fraction

In some embodiments, the compositions of the invention comprise a flow-through fraction comprising an anti-IL-1R1 antibody, or antigen-binding portion thereof, wherein the flow-through fraction is collected from an anion exchange chromatography resin.

In some embodiments, the flow-through fraction comprising an antibody or antigen-binding portion thereof, for example, an anti-IL-1R1 antibody, such as KPL-387, collected following an anion exchange chromatography step, comprises less than about 55%, about 54%, about 53%, about 52%, about 51%, about 50%, about 49%, about 48%, about 47%, about 46%, about 45%, about 44%, about 43%, about 42%, about 41%, about 40%, about 39%, about 38%, about 37%, about 36%, about 35%, about 34.5%, about 34%, about 33%, about 32%, about 31%, about 30%, about 29%, about 28%, about 27%, about 26%, about 25%, about 24%, about 23%, about 22%, about 21%, about 20%, about 19%, about 18%, about 17%, about 16%, about 15%, about 14%, about 13%, about 12%, about 11%, or about 10% of the acidic species, and ranges within one or more of the preceding. In a particular embodiment, the flow-through fraction comprises less than 55% acidic species. In a particular embodiment, the flow-through fraction comprises less than 50% acidic species. In a particular embodiment, the flow-through fraction comprises less than 40% acidic species. In another embodiment, the flow-through fraction comprises less than 39% acidic species. In another embodiment, the flow-through fraction comprises less than 38% acidic species. In another embodiment, the flow-through fraction comprises less than 37% acidic species. In another embodiment, the flow-through fraction comprises less than 36% acidic species. In another embodiment, the flow-through fraction comprises less than 35% acidic species. In another embodiment, the eluate fraction comprises less than 34.5% acidic species. In another embodiment, the eluate fraction comprises less than 34% acidic species.

In some embodiments, the flow-through fraction comprising an antibody or antigen-binding portion thereof, for example, an anti-IL-1R1 antibody, such as KPL-387, collected following an anion exchange chromatography step, comprises about 30-55%, about 31-55%, about 32-55%, about 33-55%, about 34-55%, about 35-55%, about 30-40%, about 31-40%, about 32-40%, about 33-40%, about 34-40%, about 35-40%, about 31-39%, about 31-38%, about 31-37%, about 31-36%, about 32-39%, about 32-38%, about 32-37%, about 32-36%, about 33-39%, about 33-38%, about 33-37%, about 33-36%, about 34-39%, about 34-38%, about 34-37%, or about 34-36% of the acidic species, and ranges within one or more of the preceding. In some embodiments, the flow-through fraction comprises about 30-55% acidic species. In some embodiments, the flow-through fraction comprises about 30-45% acidic species. In some embodiments, the flow-through fraction comprises about 30-40% acidic species. In some embodiments, the flow-through fraction comprises about 34-36% acidic species.

In some embodiments, the flow-through fraction comprising an antibody or antigen-binding portion thereof, for example, an anti-IL-1R1 antibody, such as KPL-387, collected following an anion exchange chromatography step, comprises less than about 15%, about 14%, about 13%, about 12%, about 11%, about 10%, about 9%, about 8%, about 7%, about 6%, about 5%, about 4%, about 3%, about 2%, or about 1% of the basic species, and ranges within one or more of the preceding. In some embodiments, the flow-through fraction comprises less than about 15% basic species. In some embodiments, the flow-through fraction comprises less than about 10% basic species. In some embodiments, the flow-through fraction comprises less than about 5% basic species. In some embodiments, the flow-through fraction comprises less than about 4% basic species. In some embodiments, the flow-through fraction comprises less than about 3% basic species. In some embodiments, the flow-through fraction comprises less than about 2% basic species.

In some embodiments, the flow-through fraction comprising an antibody or antigen-binding portion thereof, for example, an anti-IL-1R1 antibody, such as KPL-387, collected following an anion exchange chromatography step, comprises about 0.1-10%, about 0.1-9%, about 0.1-8%, about 0.1-7%, about 0.1-6%, about 0.1-5%, about 0.1-4%, about 0.1-3%, about 0.1-2%, about 1-15%, about 1-14%, about 1-13%, about 1-12%, about 1-11%, about 1-10%, about 1-9%, about 1-8%, about 1-7%, about 1-6%, about 1-5%, about 2-5%, about 2-4%, about 1-4%, about 1-3%, or about 1-2% of the basic species, and ranges within one or more of the preceding. In some embodiments, the flow-through fraction comprises about 0.1-10% basic species. In some embodiments, the flow-through fraction comprises about 1-15% basic species. In some embodiments, the flow-through fraction comprises about 1-10% basic species. In some embodiments, the flow-through fraction comprises about 1-5% basic species. In some embodiments, the flow-through fraction comprises about 2-4% basic species. In some embodiments, the flow-through fraction comprises about 1-4% basic species.

In some embodiments, the flow-through fraction comprising an antibody or antigen-binding portion thereof, for example, an anti-IL-1R1 antibody, such as KPL-387, collected following an anion exchange chromatography step, comprises more than about 40%, e.g., about 41%, about 42%, about 43%, about 44%, about 45%, about 46%, about 47%, about 48%, about 49%, about 50%, about 55%, about 60%, about 61%, about 62%, about 63%, about 64%, about 65%, about 66%, about 67%, about 68%, about 69%, about 70%, about 75%, about 80%, about 85%, about 90%, about 95% or about 99% main species of the antibody, and ranges within one or more of the preceding. In a particular embodiment, the flow-through fraction comprises more than 40% main species. In a particular embodiment, the flow-through fraction comprises more than 45% main species. In a particular embodiment, the flow-through fraction comprises more than 55% main species. In another embodiment, the flow-through fraction comprises more than 56% main species. In another embodiment, the flow-through fraction comprises more than 57% main species. In another embodiment, the flow-through fraction comprises more than 58% main species. In another embodiment, the flow-through fraction comprises more than 59% main species. In another embodiment, the flow-through fraction comprises more than 60% main species. In another embodiment, the flow-through fraction comprises more than 61% main species. In another embodiment, the flow-through fraction comprises more than 62% main species.

In some embodiments, the flow-through fraction comprising an antibody or antigen-binding portion thereof, for example, an anti-IL-1R1 antibody, such as KPL-387, collected following an anion exchange chromatography step, comprises about 40-70%, about 40-65%, about 40-60%, about 40-55%, about 40-50%, about 55-95%, about 55-85%, about 55-75%, about 55-70%, about 60-70%, about 60-65%, or about 60-63% main species of the antibody, and ranges within one or more of the preceding. In some embodiments, the flow-through fraction comprises about 40-75% main species. In some embodiments, the flow-through fraction comprises about 55-75% main species. In some embodiments, the flow-through fraction comprises about 60-63% main species.

In some embodiments, the flow-through fraction comprising an antibody or antigen-binding portion thereof, for example, an anti-IL-1R1 antibody, such as KPL-387, collected following an anion exchange chromatography step, comprises about 30-55% acidic species, about 1-15% basic species, and/or about 40-75% main species.

In some embodiments, the flow-through fraction comprising an antibody or antigen-binding portion thereof, for example, an anti-IL-1R1 antibody, such as KPL-387, collected following an anion exchange chromatography step, comprises about 30-40% acidic species, about 1-5% basic species, and/or about 55-75% main species.

In some embodiments, the flow-through fraction comprising an antibody or antigen-binding portion thereof, for example, an anti-IL-1R1 antibody, such as KPL-387, collected following an anion exchange chromatography step, comprises about 34-36% acidic species, about 1-5% basic species, and/or about 60-63% main species.

In some embodiments, the level of acidic species, the level of main species, or the level of basic species is determined by Imaging Capillary Isoelectric Focusing (iCIEF).

In some embodiments, the flow-through fraction comprising an antibody or antigen-binding portion thereof, for example, an anti-IL-1R1 antibody, such as KPL-387, collected following an anion exchange chromatography step, comprises less than about 10%, about 9%, about 8%, about 7%, about 6%, about 5%, about 4%, about 3%, about 2.5%, about 2%, or about 1% high molecular weight aggregates, and ranges within one or more of the preceding. In some embodiments, the flow-through fraction comprises less than about 3% high molecular weight aggregates. In some embodiments, the flow-through fraction comprises less than about 2% high molecular weight aggregates.

In some embodiments, the flow-through fraction comprising an antibody or antigen-binding portion thereof, for example, an anti-IL-1R1 antibody, such as KPL-387, collected following an anion exchange chromatography step, comprises about 1-10%, about 1-9%, about 1-8%, about 1-7%, about 1-6%, about 1-5%, about 1-4%, about 1-3% or about 1-2% high molecular weight aggregates, and ranges within one or more of the preceding. In some embodiments, the flow-through fraction comprises about 1-10% high molecular weight aggregates. In some embodiments, the flow-through fraction comprises about 1-3% high molecular weight aggregates. In some embodiments, the flow-through composition comprises about 1-2% high molecular weight aggregates.

In some embodiments, the flow-through fraction comprising an antibody or antigen-binding portion thereof, for example, an anti-IL-1R1 antibody, such as KPL-387, collected following an anion exchange chromatography step, comprises more than about 90%, about 91%, about 92%, about 93%, about 94%, about 95%, about 96%, about 97%, about 98%, or about 99% antibody monomer. In some embodiments, the flow-through fraction comprises more than about 97% antibody monomer. In some embodiments, the flow-through fraction comprises more than about 98% antibody monomer. In some embodiments, the flow-through fraction comprises more than about 99% antibody monomer.

In some embodiments, the flow-through fraction comprising an antibody or antigen-binding portion thereof, for example, an anti-IL-1R1 antibody, such as KPL-387, collected following an anion exchange chromatography step, comprises about 90-99.9%, about 90-99%, about 95-99%, about 96-99%, about 97-99%, or about 98-99% antibody monomer, and ranges within one or more of the preceding. In some embodiments, the flow-through fraction comprises about 90-99% antibody monomer. In some embodiments, the flow-through fraction comprises about 97-99% antibody monomer.

In some embodiments, the level of high molecular weight aggregates, or the level of antibody monomer are determined by size exclusion chromatography.

In some embodiments, the flow-through fraction comprising an antibody or antigen-binding portion thereof, for example, an anti-IL-1R1 antibody, such as KPL-387, collected following an anion exchange chromatography step, comprises more than about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, or about 80% isoform B of the antibody, and ranges within one or more of the preceding. In some embodiments, the flow-through fraction comprises more than about 40% isoform B of the antibody. In another embodiment, the flow-through fraction comprises more than about 45% isoform B of the antibody. In another embodiment, the flow-through fraction comprises more than about 50% isoform B of the antibody. In another embodiment, the flow-through fraction comprises more than about 55% isoform B of the antibody. In another embodiment, the flow-through fraction comprises more than about 60% isoform B of the antibody. In another embodiment, the flow-through fraction comprises more than about 65% isoform B of the antibody. In another embodiment, the flow-through fraction comprises more than about 70% isoform B of the antibody.

In some embodiments, the flow-through fraction comprising an antibody or antigen-binding portion thereof, for example, an anti-IL-1R1 antibody, such as KPL-387, collected following an anion exchange chromatography step, comprises about 40-80%, about 45-80%, about 45-75%, about 45-70%, about 45-65%, about 45-60%, about 50-80%, about 50-75%, about 50-70%, about 50-65%, or about 55-70% isoform B of the antibody, and ranges within one or more of the preceding. In some embodiments, the flow-through fraction comprises about 40-80% isoform B. In some embodiments, the flow-through fraction comprises about 45-60% isoform B. In some embodiments, the flow-through fraction comprises about 50-70% isoform B. In some embodiments, the flow-through fraction comprises about 50-75% isoform B.

In some embodiments, the flow-through fraction comprising an antibody or antigen-binding portion thereof, for example, an anti-IL-1R1 antibody, such as KPL-387, collected following an anion exchange chromatography step, comprises less than about 30%, about 29%, about 28%, about 27%, about 26%, about 25%, about 24%, about 23%, about 22%, about 21%, about 20%, about 19%, about 18%, about 17%, about 16%, about 15%, about 14%, about 13%, about 12%, about 11%, or about 10% isoform A/B of the antibody, and ranges within one or more of the preceding. In some embodiments, the flow-through fraction comprises less than about 30% isoform A/B of the antibody. In another embodiment, the flow-through fraction comprises less than about 25% isoform A/B of the antibody. In another embodiment, the flow-through fraction comprises less than about 20% isoform A/B of the antibody. In another embodiment, the flow-through fraction comprises less than about 15% isoform A/B of the antibody.

In some embodiments, the flow-through fraction comprising an antibody or antigen-binding portion thereof, for example, an anti-IL-1R1 antibody, such as KPL-387, collected following an anion exchange chromatography step, comprises about 10-30%, about 15-30%, about 20-30%, about 10-25%, or about 15-25% isoform A/B of the antibody, and ranges within one or more of the preceding. In some embodiments, the flow-through fraction comprises about 10-30% isoform A/B. In some embodiments, the flow-through fraction comprises about 20-30% isoform A/B. In some embodiments, the flow-through fraction comprises about 15-25% isoform A/B.

In some embodiments, the flow-through fraction comprising an antibody or antigen-binding portion thereof, for example, an anti-IL-1R1 antibody, such as KPL-387, collected following an anion exchange chromatography step, comprises less than about 30%, about 29%, about 28%, about 27%, about 26%, about 25%, about 24%, about 23%, about 22%, about 21%, about 20%, about 19%, about 18%, about 17%, about 16%, about 15%, about 14%, about 13%, about 12%, about 11%, or about 10% isoform A of the antibody, and ranges within one or more of the preceding. In some embodiments, the flow-through fraction comprises less than about 30% isoform A of the antibody. In another embodiment, the flow-through fraction comprises less than about 25% isoform A of the antibody. In another embodiment, the flow-through fraction comprises less than about 20% isoform A of the antibody. In another embodiment, the flow-through fraction comprises less than about 15% isoform A of the antibody.

In some embodiments, the flow-through fraction comprising an antibody or antigen-binding portion thereof, for example, an anti-IL-1R1 antibody, such as KPL-387, collected following an anion exchange chromatography step, comprises about 10-30%, about 15-30%, about 20-30%, about 10-25%, or about 15-25% isoform A of the antibody, and ranges within one or more of the preceding. In some embodiments, the flow-through fraction comprises about 10-30% isoform A. In some embodiments, the flow-through fraction comprises about 15-30% isoform A. In some embodiments, the flow-through fraction comprises about 10-25% isoform A.

In some embodiments, the flow-through fraction comprising an antibody or antigen-binding portion thereof, for example, an anti-IL-1R1 antibody, such as KPL-387, collected following an anion exchange chromatography step, comprises about 40-80% isoform B, about 10-30% isoform A/B, and/or about 10-30% isoform A of the antibody.

In some embodiments, the flow-through fraction comprising an antibody or antigen-binding portion thereof, for example, an anti-IL-1R1 antibody, such as KPL-387, collected following an anion exchange chromatography step, comprises about 50-75% isoform B, about 15-25% isoform A/B, and/or about 10-25% isoform A of the antibody.

In some embodiments, the flow-through fraction comprising an antibody or antigen-binding portion thereof, for example, an anti-IL-1R1 antibody, such as KPL-387, collected following an anion exchange chromatography step, comprises about 45-60% isoform B, about 20-30% isoform A/B, and/or about 15-30% isoform A of the antibody.

In some embodiments, the level of antibody isoforms are determined by reverse phase chromatography.

Antibodies and Generation Thereof

In certain aspects of the invention, the antibody, or antigen binding portion thereof, that can be used in the compositions of the present disclosure can be generated by a variety of techniques, including immunization of an animal with the antigen of interest followed by conventional monoclonal antibody methodologies e.g., the standard somatic cell hybridization technique of Kohler and Milstein (1975) Nature 256: 495. Somatic cell hybridization procedures can be used. In principle, other techniques for producing monoclonal antibody can be employed as well, including viral or oncogenic transformation of B lymphocytes.

One exemplary animal system for preparing hybridomas is the murine system. Hybridoma production is a very well-established procedure. Immunization protocols and techniques for isolation of immunized splenocytes for fusion are known in the art. Fusion partners (e.g., murine myeloma cells) and fusion procedures are also known.

An antibody used in the compositions of the invention can be a human, a chimeric, or a humanized antibody. Chimeric or humanized antibodies used in the compositions of the invention can be prepared based on the sequence of a non-human monoclonal antibody prepared as described above. DNA encoding the heavy and light chain immunoglobulins can be obtained from the non-human hybridoma of interest and engineered to contain non-murine (e.g., human) immunoglobulin sequences using standard molecular biology techniques. For example, to create a chimeric antibody, murine variable regions can be linked to human constant regions using methods known in the art (see e.g., U.S. Pat. No. 4,816,567 to Cabilly et al.). To create a humanized antibody, murine CDR regions can be inserted into a human framework using methods known in the art (see e.g., U.S. Pat. No. 5,225,539 to Winter, and U.S. Pat. Nos. 5,530,101; 5,585,089; 5,693,762 and 6,180,370 to Queen et al.).

In one non-limiting embodiment, the antibodies to be used in the compositions of the invention are human monoclonal antibodies. Such human monoclonal antibodies can be generated using transgenic or transchromosomic mice carrying parts of the human immune system rather than the mouse system. These transgenic and transchromosomic mice include mice referred to herein as the HuMAb Mouse® (Medarex, Inc.), KM Mouse® (Medarex, Inc.), and Xeno-Mouse® (Amgen). The antibodies, or antigen-binding portions thereof, used in the compositions of the invention can also be produced using the methods described in U.S. Pat. No. 6,090,382, the entire contents of which is expressly incorporated herein by reference.

Moreover, alternative transchromosomic animal systems expressing human immunoglobulin genes are available in the art and can be used to raise antibodies of the disclosure. For example, mice carrying both a human heavy chain transchromosome and a human light chain transchromosome, referred to as "TC mice" can be used; such mice are described in Tomizuka et al. (2000) Proc. Natl. Acad. Sci. USA 97:722-727. Furthermore, cows carrying human heavy and light chain transchromosomes have been described in the art (e.g., Kuroiwa et al. (2002) Nature Biotechnology 20:889-894 and PCT application No. WO 2002/092812) and can be used to raise antibodies of this disclosure.

Recombinant human antibodies to be used in the compositions of the invention can be isolated by screening of a recombinant combinatorial antibody library, e.g., a scFv phage display library, prepared using human VL and VH cDNAs prepared from mRNA derived from human lymphocytes. Methodologies for preparing and screening such libraries are known in the art. In addition to commercially available kits for generating phage display libraries (e.g., the Pharmacia Recombinant Phage Antibody System, catalog no. 27-9400-01; and the Stratagene SurfZAP™ phage display kit, catalog no. 240612, the entire teachings of which are incorporated herein), examples of methods and reagents particularly amenable for use in generating and screening antibody display libraries can be found in, e.g., Ladner et al. U.S. Pat. No. 5,223,409; Kang et al. PCT Publication No. WO 92/18619; Dower et al. PCT Publication No. WO 91/17271; Winter et al. PCT Publication No. WO 92/20791; Markland et al. PCT Publication No. WO 92/15679; Breitling et al. PCT Publication No. WO 93/01288; McCafferty et al. PCT Publication No. WO 92/01047; Garrard et al. PCT Publication No. WO 92/09690; Fuchs et al. (1991) Bio/Technology 9:1370-1372; Hay et al. (1992) Hum Antibody Hybridomas 3:81-85; Huse et al. (1989) Science 246:1275-1281; McCafferty et al., Nature (1990) 348:552-554; Griffiths et al. (1993) EMBO J 12:725-734; Hawkins et al. (1992) J Mol Biol 226:889-896; Clackson et al. (1991) Nature 352:624-628; Gram et al. (1992) PNAS 89:3576-3580; Garrard et al. (1991) Bio/Technology 9:1373-1377; Hoogenboom et al. (1991) Nuc Acid Res 19:4133-4137; and Barbas et al. (1991) PNAS 88:7978-7982; the entire teachings of which are incorporated herein.

Human monoclonal antibodies to be used in the compositions of the invention can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

In certain embodiments, the human antibodies to be used in the compositions of the invention are anti-IL-1R1 antibodies and antibody portions thereof, anti-IL-1R1-related antibodies and antibody portions, and human antibodies and antibody portions with equivalent properties to anti-IL-1R1 antibodies, such as high affinity binding to IL-1R1 with low dissociation kinetics and high neutralizing capacity. In one embodiment, an anti-IL-1R1 antibody to be used in the compositions of the invention binds to the same epitope on IL-1R1 as KPL-387. In another embodiment, an anti-IL-1R1 antibody to be used in the compositions of the invention competitively inhibits binding of KPL-387 to IL-1R1 under physiological conditions. In one embodiment, the compositions of the invention comprise KPL-387, or an antigen binding portion thereof.

C. Preparation of Compositions Using Upstream Process Technologies

The invention provides methods for producing a composition comprising an antibody or antigen-binding portion thereof, for example, an anti-IL-1R1 antibody such as KPL-387, having a low level of variants and/or impurities, e.g., a consistently low level of product-related substances, e.g., protein aggregates, or charged species, e.g., acidic species, and/or a low level of process-related impurities. Such variant/impurity-reduced compositions address the need for improved product characteristics, including, but not limited to, product stability, product safety and product efficacy. The present inventors have discovered that samples with a higher level of acidic species unexpectedly exhibit a lower potency as determined by the ELISA binding assay (FIG. 9). Moreover, a higher level of acidic species in a sample at baseline was found to correlate with an increase in the amount of higher molecular weight aggregates of KPL-387 drug product formed over time (FIG. 8).

The composition of the present invention comprising an antibody or antigen-binding portion thereof, for example, an anti-IL-1R1 antibody such as KPL-387, having a consistently low level of variants and/or impurities, e.g., a low level of product-related substances, e.g., protein aggregates, or charged species, e.g., acidic species, and/or a low level of process-related impurities, can be produced by modulating conditions during the upstream process, such as cell culture.

The present invention provides methods for producing a preparation comprising an antibody, or antigen binding portion thereof, for example, an anti-IL-1R1 antibody such as KPL-387, having a low level of variants and/or impurities, e.g., a low level of product-related substances, e.g., protein aggregates, or charged species, e.g., acidic species, from a cell culture by modulating conditions for cell culture, e.g., by modulating the seeding density and/or the culture duration. In some embodiments, the level of cell viability in the culture determines the culture duration.

The present invention also provides methods for reducing the level of variants and/or impurities, e.g., the level of product-related substance, e.g., protein aggregates, or charged species, e.g., acidic species, of an antibody or antigen-binding portion thereof, for example, an anti-IL-1R1 antibody such as KPL-387, in a cell culture, by modulating conditions for cell culture, e.g., by modulating the seeding density and/or the culture duration. In some embodiments, the level of cell viability in the culture determines the culture duration.

In some embodiments, the present invention provides a method for producing a preparation comprising an antibody, or antigen binding portion thereof, for example, an anti-IL-1R1 antibody such as KPL-387, having a low level of acidic species from a cell culture by inoculating the cell culture at a seeding density of about $0.4\times10^6$ to about $0.8\times10^6$ cells/mL, e.g., about $0.4\times10^6$ to about $0.7\times10^6$ cells/mL, or about $0.4\times10^6$ to about $0.6\times10^6$ cells/mL, or about $0.5\times10^6$ cells/mL, and incubating the cell culture in a bioreactor, thereby producing the preparation comprising the antibody, or antigen binding portion thereof, having a low level of acidic species.

In some embodiments, the present invention provides a method for producing a preparation comprising an antibody, or antigen binding portion thereof, for example, an anti-IL-1R1 antibody such as KPL-387, having a low level of acidic species from a cell culture by inoculating the cell culture at a seeding density of about $0.4\times10^6$ cells/mL, or about $0.5\times10^6$ cells/mL, or about $0.6\times10^6$ cells/mL, or about $0.7\times10^6$ cells/mL, and incubating the cell culture in a bioreactor, thereby producing the preparation comprising the antibody, or antigen binding portion thereof, having a low level of acidic species.

In some embodiments, the present invention provides a method for producing a preparation comprising an antibody, or antigen binding portion thereof, for example, an anti-IL-1R1 antibody such as KPL-387, having a low level of acidic species from a cell culture by incubating the cell culture in a bioreactor for about 8 to about 24 days, e.g., about 8 to about 22 days, about 8 to about 20 days, about 8 to about 18 days, or about 8 to about 16 days, thereby producing the preparation comprising the antibody, or antigen binding portion thereof, having a low level of acidic species.

In some embodiments, the present invention provides a method for producing a preparation comprising an antibody, or antigen binding portion thereof, for example, an anti-IL-1R1 antibody such as KPL-387, having a low level of acidic species from a cell culture by incubating the cell culture in a bioreactor for no more than about 24 days, e.g., no more than about 23 days, about 22 days, about 21 days, about 20 days, about 19 days, about 18 days, about 17 days, or about 16 days, about 15 days, about 14 days, about 13 days, or about 12 days, thereby producing the preparation comprising the antibody, or antigen binding portion thereof, having a low level of acidic species.

In some embodiments, the present invention provides a method for producing a preparation comprising an antibody, or antigen binding portion thereof, for example, an anti-IL-1R1 antibody such as KPL-387, having a low level of acidic species from a cell culture by incubating the cell culture in a bioreactor, and maintaining the viability of the cell culture at a level of at least about 50%, e.g., at least about 55%, about 60%, about 65%, or about 70%, thereby producing the preparation comprising the antibody, or antigen binding portion thereof, having a low level of acidic species.

In some embodiments, the present invention provides a method for producing a preparation comprising an antibody, or antigen binding portion thereof, for example, an anti-IL-1R1 antibody such as KPL-387, having a low level of acidic species from a cell culture by incubating the cell culture in a bioreactor, and harvesting the cell culture when the viability is at least about 50%, e.g., about 55%, about 60%, about 65%, or about 70%, thereby producing the preparation comprising the antibody, or antigen binding portion thereof, having a low level of acidic species.

In some embodiments, the present invention provides a method for producing a preparation comprising an antibody, or antigen binding portion thereof, for example, an anti-IL-1R1 antibody such as KPL-387, having a low level of acidic species from a cell culture by incubating the cell culture in a bioreactor, and harvesting the cell culture when the viability decreases to no less than about 50%, e.g., about 55%, about 60%, about 65%, or about 70%, thereby producing the preparation comprising the antibody, or antigen binding portion thereof, having a low level of acidic species. In one embodiments, the present invention provides a method for producing a preparation comprising an antibody, or antigen binding portion thereof, for example, an anti-IL-1R1 antibody such as KPL-387, having a low level of acidic species from a cell culture by incubating the cell culture in a bioreactor, and harvesting the cell culture when the viability decreases to about 50%, about 55%, about 60%, about 65% or about 70%.

In some embodiments, the present invention provides a method for producing a preparation comprising an antibody, or antigen binding portion thereof, for example, an anti-IL-1R1 antibody such as KPL-387, having a low level of acidic species from a cell culture by (a) inoculating the cell culture at a seeding density of about $0.4\times10^6$ to about $0.8\times10^6$ cells/mL, (b) incubating the cell culture in a bioreactor for about 8 to about 24 days, or for no more than about 24 days, (c) maintaining the viability of the cell culture at a level of at least about 50%, and/or (d) harvesting the cell culture when the viability is at least about 50%, thereby producing the preparation comprising the antibody, or antigen binding portion thereof, having a low level of acidic species. In some embodiments, step (d) of the method comprises harvesting the cell culture when the viability is about 50%, about 55%, about 60%, about 65% or about 70%.

In some embodiments, the present invention provides a method for producing a preparation comprising an antibody, or antigen binding portion thereof, for example, an anti-IL-1R1 antibody such as KPL-387, having a low level of acidic species from a cell culture by (a) inoculating the cell culture at a seeding density of about $0.4\times10^6$ to about $0.8\times10^6$ cells/mL, (b) incubating the cell culture in a bioreactor for about 8 to about 24 days, or for no more than about 24 days, (c) maintaining the viability of the cell culture at a level of at least about 50%, and/or (d) harvesting the cell culture when the viability decreases to no less than about 50%, thereby producing the preparation comprising the antibody, or antigen binding portion thereof, having a low level of acidic species. In some embodiments, step (d) of the method comprises harvesting the cell culture when the viability decreases to about 50%, about 55%, about 60%, about 65% or about 70%.

In some embodiments, the present invention provides a method for reducing the level of acidic species of an antibody, or antigen binding portion thereof, for example, an anti-IL-1R1 antibody such as KPL-387, in a cell culture or a clarified harvest from a cell culture, by inoculating the cell culture at a seeding density of about $0.4\times10^6$ to about $0.8\times10^6$ cells/mL, e.g., about $0.4\times10^6$ to about $0.7\times10^6$ cells/mL, or about $0.4\times10^6$ to about $0.6\times10^6$ cells/mL, or about $0.5\times10^6$ cells/mL, and incubating the cell culture in a bioreactor, thereby reducing the level of acidic species of the antibody, or antigen binding portion thereof.

In some embodiments, the present invention provides a method for reducing the level of acidic species of an antibody, or antigen binding portion thereof, for example, an anti-IL-1R1 antibody such as KPL-387, in a cell culture or a clarified harvest from a cell culture, by incubating the cell culture in a bioreactor for about 8 to about 24 days, e.g., about 8 to about 22 days, about 8 to about 20 days, about 8 to about 18 days, or about 8 to about 16 days, thereby reducing the level of acidic species of the antibody, or antigen binding portion thereof.

In some embodiments, the present invention provides a method for reducing the level of acidic species of an antibody, or antigen binding portion thereof, for example, an anti-IL-1R1 antibody such as KPL-387, in a cell culture or a clarified harvest from a cell culture, by incubating the cell culture in a bioreactor for no more than about 24 days, e.g., no more than about 22 days, about 20 days, about 18 days, or about 16 days, thereby reducing the acidic species of the antibody, or antigen binding portion thereof.

In some embodiments, the present invention provides a method for reducing the level of acidic species of an antibody, or antigen binding portion thereof, for example, an anti-IL-1R1 antibody such as KPL-387, in a cell culture or a clarified harvest from a cell culture, by incubating the cell culture in a bioreactor, and maintaining the viability of the cell culture at a level of at least about 50%, e.g., at least about 55%, about 60%, about 65%, or about 70%, thereby reducing the acidic species of the antibody, or antigen binding portion thereof.

In some embodiments, the present invention provides a method for reducing the level of acidic species of an antibody, or antigen binding portion thereof, for example, an anti-IL-1R1 antibody such as KPL-387, in a cell culture or a clarified harvest from a cell culture, by incubating the cell culture in a bioreactor, and harvesting the cell culture when the viability is at least about 50%, e.g., about 55%, about 60%, about 65%, or about 70%, thereby reducing the acidic species of the antibody, or antigen binding portion thereof.

In some embodiments, the present invention provides a method for reducing the level of acidic species of an antibody, or antigen binding portion thereof, for example, an anti-IL-1R1 antibody such as KPL-387, in a cell culture or a clarified harvest from a cell culture, by incubating the cell culture in a bioreactor, and harvesting the cell culture when the viability decreases to no less than about 50%, e.g., about 55%, about 60%, about 65%, or about 70%, thereby reducing the acidic species of the antibody, or antigen binding portion thereof.

In some embodiments, the present invention provides a method for reducing the level of acidic species of an antibody, or antigen binding portion thereof, for example, an anti-IL-1R1 antibody such as KPL-387, in a cell culture or a clarified harvest from a cell culture, by incubating the cell culture in a bioreactor, and harvesting the cell culture when the viability decreases to about 50%, about 55%, about 60%, about 65%, or about 70%, thereby reducing the acidic species of the antibody, or antigen binding portion thereof.

In some embodiments, the present invention provides a method for reducing the level of acidic species of an antibody, or antigen binding portion thereof, for example, an anti-IL-1R1 antibody such as KPL-387, in a cell culture or a clarified harvest from a cell culture, by (a) inoculating the cell culture at a seeding density of about $0.4\times10^6$ to about $0.8\times10^6$ cells/mL, (b) incubating the cell culture in a bioreactor for about 8 to about 24 days, or for no more than about 24 days, (c) maintaining the viability of the cell culture at a level of at least about 50%, and/or (d) harvesting the cell culture when the viability is at least about 50%, thereby reducing the acidic species of the antibody, or antigen binding portion thereof. In some embodiments, step (d) of the method comprises harvesting the cell culture when the viability is about 50%, about 55%, about 60%, about 65% or about 70%.

In some embodiments, the present invention provides a method for reducing the level of acidic species of an antibody, or antigen binding portion thereof, for example, an anti-IL-1R1 antibody such as KPL-387, in a cell culture or a clarified harvest from a cell culture, by (a) inoculating the cell culture at a seeding density of about $0.4\times10^6$ to about $0.8\times10^6$ cells/mL, (b) incubating the cell culture in a bioreactor for about 8 to about 24 days, or for no more than about 24 days, (c) maintaining the viability of the cell culture at a level of at least about 50%, and/or (d) harvesting the cell culture when the viability decreases to no less than about 50%, thereby reducing the acidic species of the antibody, or antigen binding portion thereof. In some embodiments, step (d) of the method comprises harvesting the cell culture when the viability decreases to 50%, about 55%, about 60%, about 65% or about 70%.

The upstream process technologies may be used alone or in combination with the downstream process technologies described in Section D, below, and as described in Example 1.

In one embodiment, one or more of the upstream process technologies described herein produce a composition of the present invention comprising an antibody, or antigen binding portion thereof, for example, an anti-IL-1R1 antibody such as KPL-387, having a reduced level of variants and/or impurities, e.g., a reduced level of charged species, e.g., acidic species, as described herein.

Some embodiments of the invention comprise culturing host cells to express an antibody or antigen binding portion thereof under conditions that limit the amount of product-related substances e.g., acidic species, that are expressed by the cells. Some embodiments of the invention comprise culturing host cells under conditions that limit the conversion of the product to acidic species variants.

In certain embodiments, the composition comprising an antibody, or antigen binding portion thereof, for example, an anti-IL-1R1 antibody such as KPL-387, having a reduced level of acidic species is produced by culturing host cells in a culture wherein the process parameters, such as the seeding density, or the duration of the cell culture, are modulated to decrease the amount of acidic species produced by the host cells and/or reduce the conversion of the product to the acidic species variants. In certain embodiments, the duration of the cell culture is modulated by incubating the cell culture in a bioreactor for about 8 to about 24 days (e.g., about 16 days), or by harvesting the cell culture when the viability is at least about 50% (e.g., about 60%). In other embodiments, the composition comprising an antibody, or antigen binding portion thereof, for example, an anti-IL-1R1 antibody such as KPL-387, having a reduced level of acidic species is produced by culturing host cells in a culture wherein the viability of cell culture is monitored and the cell culture is harvested when the viability is at least about 50%, e.g., about 55%, about 60%, about 65%, or about 70%, to decrease the amount of acidic species produced by the host cells and/or reduce the conversion of the product to the acidic species variants.

In other embodiments, the composition comprising an antibody, or antigen binding portion thereof, for example, an anti-IL-1R1 antibody such as KPL-387, having a reduced level of acidic species is produced by culturing host cells in a culture wherein the viability of cell culture is monitored and the cell culture is harvested when the viability decreases to no less than about 50%, e.g., about 55%, about 60%, about 65%, or about 70%, to decrease the amount of acidic species produced by the host cells and/or reduce the conversion of the product to the acidic species variants.

In another embodiment, the composition comprising an antibody, or antigen binding portion thereof, for example, an anti-IL-1R1 antibody such as KPL-387, having a reduced level of acidic species is produced by culturing host cells in a culture wherein the viability of cell culture is monitored and the cell culture is harvested when the viability decreases to about 50%, about 55%, about 60%, about 65%, or about 70%, to decrease the amount of acidic species produced by the host cells and/or reduce the conversion of the product to the acidic species variants.

In one embodiment, the composition comprising an antibody, or antigen binding portion thereof, for example, an anti-IL-1R1 antibody such as KPL-387, having a reduced level of acidic species is produced by modulating the seeding density for the culture of cells expressing the antibody, or antigen binding portion thereof, e.g., by inoculating the cell culture at a density of about $0.4 \times 10^6$ to about $0.8 \times 10^6$ cells/mL, and incubating the cells in a bioreactor.

In another embodiment, the composition comprising an antibody, or antigen binding portion thereof, for example, an anti-IL-1R1 antibody such as KPL-387, having a reduced level of acidic species is produced by incubating cells expressing the antibody, or antigen binding portion thereof, in a bioreactor, for a certain period of time, e.g., incubating the cell culture in a bioreactor for about 8 to about 24 days, or for no more than about 24 days.

In still another embodiment, the composition comprising an antibody, or antigen binding portion thereof, for example, an anti-IL-1R1 antibody such as KPL-387, having a reduced level of acidic species having a reduced level of acidic species is produced by incubating cells expressing the antibody, or antigen binding portion thereof, in a bioreactor, and maintaining the viability of the cell culture, for example, maintaining the viability of the cell culture at a level of at least about 50%, or harvesting the cell culture at a certain viability level, e.g., harvesting the cell culture when the viability is greater than about 50%, or harvesting the cell culture when the viability decreases to no less than about 50% (e.g., decreases to about 50%, about 55%, about 60%, about 65%, or about 70%,).

In another embodiment, one or more of the above parameters and modifications can be combined and used during cell culture of the antibody composition.

To express an antibody of interest to be used in the compositions of the invention, DNAs encoding the antibody, such as DNAs encoding partial or full-length light and heavy chains of an antibody, are inserted into one or more expression vector such that the genes are operatively linked to transcriptional and translational control sequences. (See, e.g., U.S. Pat. No. 6,090,382, the entire teaching of which is incorporated herein by reference.) In this context, the term "operatively linked" is intended to mean that a gene encoding the antibody of interest is ligated into a vector such that transcriptional and translational control sequences within the vector serve their intended function of regulating the transcription and translation of the gene. The expression vector and expression control sequences are chosen to be compatible with the expression host cell used. In certain embodiments, the antibody of interest will comprise multiple polypeptides, such as the heavy and light chains of an antibody. Thus, in certain embodiments, genes encoding multiple polypeptides, such as antibody light chain genes and antibody heavy chain genes, can be inserted into a separate vector or, more typically, the genes are inserted into the same expression vector. Genes are inserted into expression vectors by standard methods (e.g., ligation of complementary restriction sites on the gene fragment and vector, or blunt end ligation if no restriction sites are present). Prior to insertion of the gene or genes, the expression vector may already carry additional polypeptide sequences, such as, but not limited to, antibody constant region sequences. For example, one approach to converting the anti-IL-1R1 antibody, or anti-IL-1R1-related VH and VL sequences to full-length antibody genes is to insert them into expression vectors already encoding heavy chain constant and light chain constant regions, respectively, such that the VH segment is operatively linked to the CH segment(s) within the vector and the VL segment is operatively linked to the CL segment within the vector. Additionally or alternatively, the recombinant expression vector can encode a signal peptide that facilitates secretion of the protein from a host cell. The gene can be cloned into the vector such that the signal peptide is linked in-frame to the amino terminus of the gene. The signal peptide can be an immunoglobulin signal peptide or a heterologous signal peptide (i.e., a signal peptide from a non-immunoglobulin protein).

In addition to protein coding genes, a recombinant expression vector can carry one or more regulatory sequence that controls the expression of the protein coding genes in a host cell. The term "regulatory sequence" is intended to include promoters, enhancers and other expression control elements (e.g., polyadenylation signals) that control the transcription or translation of the protein coding genes. Such regulatory sequences are described, e.g., in Goeddel; Gene Expression Technology: Methods in Enzymology 185, Academic Press, San Diego, CA (1990), the entire teaching of which is incorporated herein by reference. It will be appreciated by those skilled in the art that the design of the expression vector, including the selection of regulatory sequences may depend on such factors as the choice of the host cell to be transformed, the level of expression of protein desired, etc. Suitable regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. For further description of viral regulatory elements, and sequences thereof, see, e.g., U.S. Pat. No. 5,168,062 by Stinski, U.S. Pat. No. 4,510,245 by Bell et al. and U.S. Pat. No. 4,968,615 by Schaffner et al., the entire teachings of which are incorporated herein by reference.

A recombinant expression vector may also carry one or more additional sequences, such as a sequence that regulates replication of the vector in host cells (e.g., origins of replication) and/or a selectable marker gene. The selectable marker gene facilitates selection of host cells into which the vector has been introduced (see e.g., U.S. Pat. Nos. 4,399, 216, 4,634,665 and 5,179,017, all by Axel et al., the entire teachings of which are incorporated herein by reference). For example, typically the selectable marker gene confers resistance to drugs, such as G418, hygromycin or methotrexate, on a host cell into which the vector has been introduced. Suitable selectable marker genes include the dihydrofolate reductase (DHFR) gene (for use in dhfr– host cells with methotrexate selection/amplification) and the neo gene (for G418 selection).

An antibody, or antibody portion, e.g., an anti-IL-1R1 antibody such as KPL-387, to be used in the compositions of the invention can be prepared by recombinant expression of immunoglobulin light and heavy chain genes in a host cell. To express an antibody recombinantly, a host cell is transfected with one or more recombinant expression vectors carrying DNA fragments encoding the immunoglobulin light and heavy chains of the antibody such that the light and heavy chains are expressed in the host cell and secreted into the medium in which the host cells are cultured, from which medium the antibodies can be recovered. Standard recombinant DNA methodologies are used to obtain antibody heavy and light chain genes, incorporate these genes into recombinant expression vectors and introduce the vectors into host cells, such as those described in Sambrook, Fritsch and Maniatis (eds), Molecular Cloning; A Laboratory Manual, Second Edition, Cold Spring Harbor, N.Y., (1989), Ausubel et al. (eds.) Current Protocols in Molecular Biology, Greene Publishing Associates, (1989) and in U.S. Pat. Nos. 4,816,397 & 6,914,128, the entire teachings of which are incorporated herein.

For expression of protein, for example, the light and heavy chains of an antibody, the expression vector(s) encoding the protein is (are) transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the proteins of the invention in either prokaryotic or eukaryotic host cells, expression of antibodies in eukaryotic cells, such as mammalian host cells, is suitable because such eukaryotic cells, and in particular mammalian cells, are more likely than prokaryotic cells to assemble and secrete a properly folded and immunologically active protein. Prokaryotic expression of protein genes has been reported to be ineffective for production of high yields of active protein (Boss and Wood (1985) Immunology Today 6:12-13, the entire teaching of which is incorporated herein by reference).

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, e.g., Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41P disclosed in DD 266,710 published Apr. 12, 1989), *Pseudomonas* such as *P. aeruginosa*, and *Streptomyces*. One suitable *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for polypeptide encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris* (EP 183,070); *Candida; Trichoderma* reesia (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

Suitable host cells for the expression of glycosylated proteins, for example, glycosylated antibodies, are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells. Plant cell cultures of cotton, corn, potato, soybean, petunia, tomato, and tobacco can also be utilized as hosts.

Mammalian cells can be used for expression and production of the recombinant protein used in the compositions of the invention, however other eukaryotic cell types can also be employed in the context of the instant invention. See, e.g., Winnacker, From Genes to Clones, VCH Publishers, N.Y., N.Y. (1987). Suitable mammalian host cells for expressing recombinant proteins according to the invention include Chinese Hamster Ovary (CHO cells) (including dhfr– CHO cells, described in Urlaub and Chasin, (1980) PNAS USA 77:4216-4220, used with a DHFR selectable marker, e.g., as described in Kaufman and Sharp (1982) Mol. Biol. 159: 601-621, the entire teachings of which are incorporated herein by reference), NS0 myeloma cells, COS cells and SP2 cells. When recombinant expression vectors encoding protein genes are introduced into mammalian host cells, the antibodies are produced by culturing the host cells for a period of time sufficient to allow for expression of the antibody in the host cells or secretion of the antibody into the culture medium in which the host cells are grown. Other examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/-DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2), the entire teachings of which are incorporated herein by reference.

Host cells are transformed with the above-described expression or cloning vectors for protein production and cultured in conventional nutrient media modified as appropriate for inducing promoters, selecting transformants, or amplifying the genes encoding the desired sequences.

The host cells used to produce a protein may be cultured in a variety of media. Commercially available media such as Ham's F10™ (Sigma), Minimal Essential Medium™ (MEM), (Sigma), RPMI-1640 (Sigma), and Dulbecco's Modified Eagle's Medium™ (DMEM), (Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or 5,122,469; WO 90/03430; WO 87/00195; or U.S. Pat. No. Re. 30,985 may be used as culture media for the host cells, the entire teachings of which are incorporated herein by reference. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as gentamycin drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Host cells can also be used to produce portions of intact proteins, for example, antibodies, including Fab fragments or scFv molecules. It is understood that variations on the above procedure are within the scope of the present invention. For example, in certain embodiments it may be desirable to transfect a host cell with DNA encoding either the light chain or the heavy chain (but not both) of an antibody. Recombinant DNA technology may also be used to remove some or all of the DNA encoding either or both of the light and heavy chains that is not necessary for binding to an antigen. The molecules expressed from such truncated DNA molecules are also encompassed by the antibodies of the invention. In addition, bifunctional antibodies may be produced in which one heavy and one light chain are an antibody of the invention and the other heavy and light chain are specific for an antigen other than the target antibody, depending on the specificity of the antibody of the invention, by crosslinking an antibody of the invention to a second antibody by standard chemical crosslinking methods.

In a suitable system for recombinant expression of a protein, for example, an antibody, or antigen-binding portion thereof, a recombinant expression vector encoding the protein, for example, both an antibody heavy chain and an antibody light chain, is introduced into dhfr-CHO cells by calcium phosphate-mediated transfection. Within the recombinant expression vector, the protein gene(s) are each operatively linked to CMV enhancer/AdMLP promoter regulatory elements to drive high levels of transcription of the gene(s). The recombinant expression vector also carries a DHFR gene, which allows for selection of CHO cells that have been transfected with the vector using methotrexate selection/amplification. The selected transformant host cells are cultured to allow for expression of the protein, for example, the antibody heavy and light chains, and intact protein, for example, an antibody, is recovered from the culture medium. Standard molecular biology techniques are used to prepare the recombinant expression vector, transfect the host cells, select for transformants, culture the host cells and recover the protein from the culture medium.

When using recombinant techniques, the antibodies or antigen binding fragments thereof, can be produced intracellularly, in the periplasmic space, or directly secreted into the medium. For antibodies made intracellularly, the first step of a purification process typically involves: lysis of the cell, which can be done by a variety of methods, including mechanical shear, osmotic shock, or enzymatic treatments. Such disruption releases the entire contents of the cell into the homogenate, and in addition produces subcellular fragments that are difficult to remove due to their small size. These are generally removed by differential centrifugation or by filtration. Where the antibody is secreted, supernatants from such expression systems are generally first concentrated using a commercially available protein concentration filter. Where the antibody is secreted into the medium, the recombinant host cells can also be separated from the cell culture medium, e.g., by tangential flow filtration. Antibodies can be further recovered from the culture medium using the antibody purification methods of the invention.

Controlling Seeding Density to Modulate Acidic Species

In certain embodiments, the seeding density of the cell culture is controlled (e.g., increased or decreased) in order to produce a composition of the invention comprising an antibody or antigen-binding portion thereof, for example, an anti-IL-1R1 antibody such as KPL-387, having a desired level of variants and/or impurities, e.g., a reduced level of acidic species. For example, the seeding density of the cell culture may be modulated in order to achieve a desired acidic species level.

In certain embodiments, the seeding density of the cell culture is about $0.4 \times 10^6$ to about $0.8 \times 10^6$ cells/mL, about $0.4 \times 10^6$ to about $0.7 \times 10^6$ cells/mL, or about $0.4 \times 10^6$ to about $0.6 \times 10^6$ cells/mL. In certain embodiments, the seeding density of the cell culture is about $0.4 \times 10^6$ to about $0.5 \times 10^6$ cells/mL.

In certain embodiments, the seeding density of the cell culture is about $0.4 \times 10^6$ cells/mL, about $0.5 \times 10^6$ cells/mL, about $0.6 \times 10^6$ cells/mL, about $0.7 \times 10^6$ cells/mL, or about $0.8 \times 10^6$ cells/mL. In certain embodiments, the seeding density of the cell culture is about $0.4 \times 10^6$ cells/mL. In certain embodiments, the seeding density of the cell culture is about $0.5 \times 10^6$ cells/mL. In certain embodiments, the seeding density of the cell culture is about $0.6 \times 10^6$ cells/mL.

The seeding density is selected in such a manner as to produce a composition comprising an antibody or antigen-binding portion thereof, for example, an anti-IL-1R1 antibody such as KPL-387, having a reduced level of acidic species, wherein the composition comprises less than about 55%, about 54%, about 53%, about 52%, about 51%, about 50%, about 49%, about 48%, about 47%, about 46%, about 45%, about 44%, about 43%, about 42%, about 41%, about 40%, about 39%, about 38%, about 37%, about 36%, about 35%, about 34%, about 33%, about 32%, about 31%, about 30%, about 29%, about 28%, about 27%, about 26%, about 25%, about 24%, about 23%, about 22%, about 21%, about 20%, about 19%, about 18%, about 17%, about 16%, about 15%, about 14%, about 13%, about 12%, about 11%, or about 10% acidic species, and ranges within one or more of the preceding. In some embodiments, the composition comprises about 30-55%, about 31-55%, about 32-55%, about 33-55%, about 34-55%, about 35-55%, about 30-40%, about 31-40%, about 32-40%, about 33-40%, about 34-40%, about 35-40%, about 31-39%, about 31-38%, about 31-37%, about 31-36%, about 32-39%, about 32-38%, about 32-37%, about 32-36%, about 33-39%, about 33-38%, about 33-37%, about 33-36%, about 34-39%, about 34-38%, about 34-37%, or about 34-36% acidic species, and ranges within one or more of the preceding acidic species, and ranges within one or more of the preceding.

In some embodiments, the composition comprises a clarified harvest from cell culture, wherein the clarified harvest comprises less than about 55%, about 54%, about 53%, about 52%, about 51%, about 50%, about 49%, about 48%, about 47%, about 46%, about 45%, about 44%, about 43%, about 42%, about 41%, about 40%, about 39%, about 38%, about 37%, about 36%, about 35%, about 34%, about 33%, about 32%, about 31%, about 30%, about 29%, about 28%, about 27%, about 26%, about 25%, about 24%, about 23%, about 22%, about 21%, about 20%, about 19%, about 18%, about 17%, about 16%, about 15%, about 14%, about 13%, about 12%, about 11%, or about 10% acidic species, and ranges within one or more of the preceding. In some embodiments, the clarified harvest comprises about 30-55%, about 31-55%, about 32-55%, about 33-55%, about 34-55%, about 35-55%, about 30-40%, about 31-40%, about 32-40%, about 33-40%, about 34-40%, about 35-40%, about 31-39%, about 31-38%, about 31-37%, about 31-36%, about 32-39%, about 32-38%, about 32-37%, about 32-36%, about 33-39%, about 33-38%, about 33-37%, about 33-36%, about 34-39%, about 34-38%, about 34-37%, or about 34-36% acidic species, and ranges within one or more of the preceding acidic species, and ranges within one or more of the preceding.

In certain embodiments, the seeding density is selected in such a manner as to reduce the amount of acidic species in an antibody composition by about 1%, 2%, 3%, 4%, 5%, 6%, 7%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, 100%, and ranges within one or more of the preceding.

In certain embodiments, the seeding density is selected to decrease the amount of acidic species and/or the rate at which such acidic species form.

In certain embodiments, a composition of the invention having a reduced level of variants and/or impurities, e.g., a reduced level of acidic species, can be produced from cell culture expressing the antibody of interest as described herein by modulating the seeding density of the cell culture, as described herein, along with the choice of suitable culture duration and/or suitable cell viability, as described herein. The culture conditions can be used in various cultivation methods including, but not limited to, batch, fed-batch, chemostat and perfusion, and with various cell culture equipment including, but not limited to, shake flasks with or without suitable agitation, spinner flasks, stirred bioreactors, airlift bioreactors, membrane bioreactors, reactors with cells retained on a solid support or immobilized/entrapped as in microporous beads, and any other configuration appropriate for optimal growth and productivity of the desired cell line. In some embodiments, the cell culture is a fed-batch culture.

Adjusting Culture Duration to Modulate Acidic Species

In certain embodiments, the duration of the cell culture is controlled (e.g., increased or decreased) in order to produce a composition of the invention comprising an antibody or antigen-binding portion thereof, for example, an anti-IL-1R1 antibody such as KPL-387, having a desired level of variants and/or impurities, e.g., a reduced level of acidic species. For example, the duration of the cell culture may be modulated in order to achieve a desired antibody expression, cell viability, and acidic species level.

In certain embodiments, the culture duration is about 8 to about 24 days, e.g., about 8 to about 22 days, about 8 to about 20 days, about 8 to about 18 days, or about 8 to about 16 days. In certain embodiments, the culture duration is about 8 to about 16 days.

In certain embodiments, the culture duration is no more than about 24 days, e.g., no more than about 22 days, about 20 days, about 18 days, or about 16 days. In certain embodiments, the culture duration is no more than about 16 days.

In some embodiments, the culture duration is about 24 days, about 23 days, about 22 days, about 21 days, about 20 days, about 19 days, about 18 days, about 17 days, about 16 days, about 15 days, about 14 days, about 13 days, about 12 days, about 11 days, about 10 days, about 9 days, or about 8 days. In some embodiments, the culture duration is about 16 days.

The culture duration is selected in such a manner as to produce a composition comprising an antibody or antigen-binding portion thereof, for example, an anti-IL-1R1 antibody such as KPL-387, having a reduced level of acidic species, wherein the composition comprises less than about 55%, about 54%, about 53%, about 52%, about 51%, about 50%, about 49%, about 48%, about 47%, about 46%, about 45%, about 44%, about 43%, about 42%, about 41%, about 40%, about 39%, about 38%, about 37%, about 36%, about 35%, about 34%, about 33%, about 32%, about 31%, about 30%, about 29%, about 28%, about 27%, about 26%, about 25%, about 24%, about 23%, about 22%, about 21%, about 20%, about 19%, about 18%, about 17%, about 16%, about 15%, about 14%, about 13%, about 12%, about 11%, or about 10% acidic species, and ranges within one or more of the preceding. In some embodiments, the composition comprises about 30-55%, about 31-55%, about 32-55%, about 33-55%, about 34-55%, about 35-55%, about 30-40%, about 31-40%, about 32-40%, about 33-40%, about 34-40%, about 35-40%, about 31-39%, about 31-38%, about 31-37%, about 31-36%, about 32-39%, about 32-38%, about 32-37%, about 32-36%, about 33-39%, about 33-38%, about 33-37%, about 33-36%, about 34-39%, about 34-38%, about 34-37%, or about 34-36% acidic species, and ranges within one or more of the preceding acidic species, and ranges within one or more of the preceding.

In some embodiments, the composition comprises a clarified harvest from cell culture, wherein the clarified harvest comprises less than about 55%, about 54%, about 53%, about 52%, about 51%, about 50%, about 49%, about 48%, about 47%, about 46%, about 45%, about 44%, about 43%, about 42%, about 41%, about 40%, about 39%, about 38%, about 37%, about 36%, about 35%, about 34%, about 33%, about 32%, about 31%, about 30%, about 29%, about 28%, about 27%, about 26%, about 25%, about 24%, about 23%, about 22%, about 21%, about 20%, about 19%, about 18%, about 17%, about 16%, about 15%, about 14%, about 13%, about 12%, about 11%, or about 10% acidic species, and ranges within one or more of the preceding. In some embodiments, the clarified harvest comprises about about 30-55%, about 31-55%, about 32-55%, about 33-55%, about 34-55%, about 35-55%, 30-40%, about 31-40%, about 32-40%, about 33-40%, about 34-40%, about 35-40%, about 31-39%, about 31-38%, about 31-37%, about 31-36%, about 32-39%, about 32-38%, about 32-37%, about 32-36%, about 33-39%, about 33-38%, about 33-37%, about 33-36%, about 34-39%, about 34-38%, about 34-37%, or about 34-36% acidic species, and ranges within one or more of the preceding acidic species, and ranges within one or more of the preceding.

In certain embodiments, the culture duration is selected in such a manner as to reduce the amount of acidic species in an antibody composition by about 1%, 2%, 3%, 4%, 5%, 6%, 7%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, 100%, and ranges within one or more of the preceding.

In certain embodiments, the culture duration is selected to decrease the amount of acidic species and/or the rate at which such acidic species form.

In certain embodiments, a composition of the invention having a reduced level of variants and/or impurities, e.g., a reduced level of acidic species, can be produced from cell culture expressing the antibody of interest by modulating the duration of the cell culture, as described herein, along with the choice of suitable seeding density and/or suitable cell viability, as described herein. The culture conditions can be used in various cultivation methods including, but not limited to, batch, fed-batch, chemostat and perfusion, and with various cell culture equipment including, but not limited to, shake flasks with or without suitable agitation, spinner flasks, stirred bioreactors, airlift bioreactors, membrane bioreactors, reactors with cells retained on a solid support or immobilized/entrapped as in microporous beads, and any other configuration appropriate for optimal growth and productivity of the desired cell line. In some embodiments, the cell culture is a fed-batch culture.

Monitoring Cell Viability to Modulate Acidic Species

In certain embodiments, the cell culture viability is monitored in order to produce a composition of the invention comprising an antibody or antigen-binding portion thereof, for example, an anti-IL-1R1 antibody such as KPL-387, having a desired level of variants and/or impurities, e.g., a reduced level of acidic species.

In certain embodiments, the viability of the cell culture is maintained at a level of about 50%-100%, about 55%-100%, about 60%-100%, about 65%-100%, about 70%-100%, about 75%-100%, about 80%-100%, about 85%-100%, about 90%-100%, about 50%-70%, or about 55%-65%. In certain embodiments, the viability of the cell culture is maintained at a level of about 60%-100%.

In some embodiments, the viability of the cell culture is maintained at a level of at least about 50%, e.g., at least about 55%, about 60%, about 65%, about 70%, about 75%, about 80%, about 85%, about 90%, about 95%, or about 99%. In some embodiments, the viability of the cell culture is maintained at a level of at least about 60%.

In certain embodiments, the cell culture is harvested when the viability of the cell culture is at least about 50%, e.g., at least about 55%, about 60%, about 65%, about 70%, about 75%, about 80%, about 85%, about 90%, about 95%, or about 99%. In certain embodiments, the cell culture is harvested when the viability of the cell culture is at least about 60%.

In certain embodiments, the cell culture is harvested when the viability of the cell culture decreases to no less than about 50%, e.g., no less than about 55%, about 60%, about 65%, about 70%, about 75%, about 80%, about 85%, about 90%, about 95%, or about 99%. In certain embodiments, the cell culture is harvested when the viability of the cell culture decreases to no less than about 60%.

In certain embodiments, the cell culture is harvested when the viability of the cell culture decreases to about 50%, about 55%, about 60%, about 65%, about 70%, about 75%, about 80%, about 85%, about 90%, about 95%, or about 99%. In certain embodiments, the cell culture is harvested when the viability of the cell culture decreases to about 50%, about 55%, about 60%, about 65%, about 70%. In certain embodiments, the cell culture is harvested when the viability of the cell culture decreases to about 60%.

In certain embodiments, the cell culture is harvested when the viability of the cell culture decreases to about 55%-65%. In certain embodiments, the cell culture is harvested when the viability of the cell culture decreases to about 50%-70%.

The cell culture viability is monitored in such a manner as to produce a composition comprising an antibody or antigen-binding portion thereof, for example, an anti-IL-1R1 antibody such as KPL-387, having a reduced level of acidic species, wherein the composition comprises less than about 55%, about 54%, about 53%, about 52%, about 51%, about 50%, about 49%, about 48%, about 47%, about 46%, about 45%, about 44%, about 43%, about 42%, about 41%, about 40%, about 39%, about 38%, about 37%, about 36%, about 35%, about 34%, about 33%, about 32%, about 31%, about 30%, about 29%, about 28%, about 27%, about 26%, about 25%, about 24%, about 23%, about 22%, about 21%, about 20%, about 19%, about 18%, about 17%, about 16%, about 15%, about 14%, about 13%, about 12%, about 11%, or about 10% acidic species, and ranges within one or more of the preceding. In some embodiments, the composition comprises about 30-55%, about 31-55%, about 32-55%, about 33-55%, about 34-55%, about 35-55%, about 30-40%, about 31-40%, about 32-40%, about 33-40%, about 34-40%, about 35-40%, about 31-39%, about 31-38%, about 31-37%, about 31-36%, about 32-39%, about 32-38%, about 32-37%, about 32-36%, about 33-39%, about 33-38%, about 33-37%, about 33-36%, about 34-39%, about 34-38%, about 34-37%, or about 34-36% acidic species, and ranges within one or more of the preceding acidic species, and ranges within one or more of the preceding.

In some embodiments, the composition comprises a clarified harvest from cell culture, wherein the clarified harvest comprises less than about 55%, about 54%, about 53%, about 52%, about 51%, about 50%, about 49%, about 48%, about 47%, about 46%, about 45%, about 44%, about 43%, about 42%, about 41%, about 40%, about 39%, about 38%, about 37%, about 36%, about 35%, about 34%, about 33%, about 32%, about 31%, about 30%, about 29%, about 28%, about 27%, about 26%, about 25%, about 24%, about 23%, about 22%, about 21%, about 20%, about 19%, about 18%, about 17%, about 16%, about 15%, about 14%, about 13%, about 12%, about 11%, or about 10% acidic species, and ranges within one or more of the preceding. In some embodiments, the clarified harvest comprises about 30-55%, about 31-55%, about 32-55%, about 33-55%, about 34-55%, about 35-55%, about 30-40%, about 31-40%, about 32-40%, about 33-40%, about 34-40%, about 35-40%, about 31-39%, about 31-38%, about 31-37%, about 31-36%, about 32-39%, about 32-38%, about 32-37%, about 32-36%, about 33-39%, about 33-38%, about 33-37%, about 33-36%, about 34-39%, about 34-38%, about 34-37%, or about 34-36% acidic species, and ranges within one or more of the preceding acidic species, and ranges within one or more of the preceding.

In certain embodiments, the cell culture viability is monitored in such a manner as to reduce the amount of acidic species in an antibody composition by about 1%, 2%, 3%, 4%, 5%, 6%, 7%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, 100%, and ranges within one or more of the preceding.

In certain embodiments, the cell culture viability is monitored to decrease the amount of acidic species and/or the rate at which such acidic species form.

In certain embodiments, a composition of the invention having a reduced level of variants and/or impurities, e.g., a reduced level of acidic species, can be produced from cell culture expressing the antibody of interest by monitoring the cell culture viability, as described herein, along with the choice of suitable seeding density and/or suitable culture duration, as described herein. The culture conditions can be used in various cultivation methods including, but not limited to, batch, fed-batch, chemostat and perfusion, and with various cell culture equipment including, but not limited to, shake flasks with or without suitable agitation, spinner flasks, stirred bioreactors, airlift bioreactors, membrane bioreactors, reactors with cells retained on a solid support or immobilized/entrapped as in microporous beads, and any other configuration appropriate for optimal growth and productivity of the desired cell line. In some embodiments, the cell culture is a fed-batch culture.

D. Preparation of Compositions Using Downstream Process Technologies

The invention provides methods for producing a composition comprising an antibody or antigen-binding portion thereof, for example, an anti-IL-1R1 antibody such as KPL-387, having a consistently low level of variants and/or impurities, e.g., a consistently low level of product-related substances, e.g., protein aggregates, or charged species, e.g., acidic species, and/or a low level of process-related impurities. Such variants/impurities-reduced compositions address the need for improved product characteristics, including, but not limited to, product stability, product safety and product efficacy. Surprisingly, the present inventors have discovered that samples with a higher level of acidic species exhibited a lower potency as determined by the ELISA binding assay (FIG. 9). Moreover, a higher level of acidic species in a sample at baseline was found to correlate with an increase in the amount of higher molecular weight aggregates of KPL-387 drug product formed over time (FIG. 8).

In certain embodiments, the present invention is directed to a method for producing a composition comprising an anti-IL-1R1 antibody, or antigen-binding portion thereof, having less than about 55% acidic species, the method comprising subjecting a sample comprising the anti-IL-1R1 antibody, or antigen-binding portion thereof, to a chromatography resin, wherein the chromatography resin is selected from a group consisting of a cation exchange chromatography resin and an anion exchange chromatography resin, or a combination thereof.

In some embodiments, the composition comprises less than about 55%, about 54%, about 53%, about 52%, about 51%, about 50%, about 49%, about 48%, about 47%, about 46%, about 45%, about 44%, about 43%, about 42%, about 41%, about 40%, about 39%, about 38%, about 37%, about 36%, about 35%, about 34%, about 33%, about 32%, about 31%, about 30%, about 29%, about 28%, about 27%, about 26%, about 25%, about 24%, about 23%, about 22%, about 21%, about 20%, about 19%, about 18%, about 17%, about 16%, about 15%, about 14%, about 13%, about 12%, about 11%, or about 10% acidic species.

In certain embodiments, the present invention is directed to a method for producing a composition comprising an anti-IL-1R1 antibody, or antigen-binding portion thereof, having about 30-55% acidic species, the method comprising subjecting a sample comprising the anti-IL-1R1 antibody, or antigen-binding portion thereof, to a chromatography resin, wherein the chromatography resin is selected from a group consisting of a cation exchange chromatography resin and an anion exchange chromatography resin, or a combination thereof.

In some embodiments, the composition comprises about 30-55%, about 31-55%, about 32-55%, about 33-55%, about 34-55%, about 35-55%, about 30-40%, about 31-40%, about 32-40%, about 33-40%, about 34-40%, about 35-40%, about 31-39%, about 31-38%, about 31-37%, about 31-36%, about 32-39%, about 32-38%, about 32-37%, about 32-36%, about 33-39%, about 33-38%, about 33-37%, about 33-36%, about 34-39%, about 34-38%, about 34-37%, or about 34-36% acidic species, and ranges within one or more of the preceding. In some embodiments, the composition comprises about 30-55% acidic species. In some embodiments, the composition comprises about 30-40% acidic species. In some embodiments, the composition comprises about 34-36% acidic species.

In some embodiments, the present invention provides a method of maintaining the level of acidic species at less than about 40% in a composition comprising an anti-IL-1R1 antibody, or antigen-binding portion thereof, the method comprising subjecting a sample comprising the anti-IL-1R1 antibody, or antigen-binding portion thereof, to a chromatography resin, wherein the chromatography resin is selected from a group consisting of a cation exchange chromatography resin and an anion exchange chromatography resin, or a combination thereof.

In some embodiments, the method maintains the level of acidic species in the composition at less than about 55%, about 54%, about 53%, about 52%, about 51%, about 50%, about 49%, about 48%, about 47%, about 46%, about 45%, about 44%, about 43%, about 42%, about 41%, about 40%, about 39%, about 38%, about 37%, about 36%, about 35%, about 34%, about 33%, about 32%, about 31%, about 30%, about 29%, about 28%, about 27%, about 26%, about 25%, about 24%, about 23%, about 22%, about 21%, about 20%, about 19%, about 18%, about 17%, about 16%, about 15%, about 14%, about 13%, about 12%, about 11%, or about 10% acidic species.

In some embodiments, the present invention provides a method of maintaining the level of acidic species at about 30-55% in a composition comprising an anti-IL-1R1 antibody, or antigen-binding portion thereof, the method comprising subjecting a sample comprising the anti-IL-1R1 antibody, or antigen-binding portion thereof, to a chromatography resin, wherein the chromatography resin is selected from a group consisting of a cation exchange chromatography resin and an anion exchange chromatography resin, or a combination thereof.

In some embodiments, the method maintains the level of acidic species in the composition at about 30-55%, about 31-55%, about 32-55%, about 33-55%, about 34-55%, about 35-55%, about 30-40%, about 31-40%, about 32-40%, about 33-40%, about 34-40%, about 35-40%, about 31-39%, about 31-38%, about 31-37%, about 31-36%, about 32-39%, about 32-38%, about 32-37%, about 32-36%, about 33-39%, about 33-38%, about 33-37%, about 33-36%, about 34-39%, about 34-38%, about 34-37%, or about 34-36%, and ranges within one or more of the preceding. In some embodiments, the method maintains the level of acidic species in the composition at about 30-55% acidic species. In some embodiments, the method maintains the level of acidic species in the composition at about 30-40% acidic species. In some embodiments, the method maintains the level of acidic species in the composition at about 34-36% acidic species.

In some embodiments, the present invention provides a method of preventing the level of acidic species from exceeding about 55% in a composition comprising an anti-IL-1R1 antibody, or antigen-binding portion thereof, the method comprising subjecting a sample comprising the anti-IL-1R1 antibody, or antigen-binding portion thereof, to a chromatography resin, wherein the chromatography resin is selected from a group consisting of a cation exchange chromatography resin and an anion exchange chromatography resin.

In some embodiments, the method comprises preventing the level of acid species from exceeding about 54% in the composition. In some embodiments, the method comprises preventing the level of acid species from exceeding about 53% in the composition. In some embodiments, the method comprises preventing the level of acid species from exceeding about 52% in the composition. In some embodiments, the method comprises preventing the level of acid species from exceeding about 51% in the composition. In some embodiments, the method comprises preventing the level of acid species from exceeding about 50% in the composition. In some embodiments, the method comprises preventing the level of acid species from exceeding about 45% in the composition. In some embodiments, the method comprises preventing the level of acid species from exceeding about 40% in the composition. In some embodiments, the method comprises preventing the level of acid species from exceeding about 39% in the composition. In some embodiments, the method comprises preventing the level of acid species from exceeding about 38% in the composition. In some embodiments, the method comprises preventing the level of acid species from exceeding about 37% in the composition. In some embodiments, the method comprises preventing the level of acid species from exceeding about 36% in the composition.

In some embodiments, the method further comprises maintaining the level of basic species at about less than 15%, or preventing the level of basic species from exceeding 15%. In some embodiments, the method further comprises maintaining the level of basic species at about less than 14%, or preventing the level of basic species from exceeding 14%. In some embodiments, the method further comprises maintaining the level of basic species at about less than 15%, or preventing the level of basic species from exceeding 13%. In some embodiments, the method further comprises maintaining the level of basic species at about less than 12%, or preventing the level of basic species from exceeding 12%. In some embodiments, the method further comprises maintaining the level of basic species at about less than 11%, or preventing the level of basic species from exceeding 11%. In some embodiments, the method further comprises maintaining the level of basic species at about less than 10%, or preventing the level of basic species from exceeding 10%. In some embodiments, the method further comprises maintaining the level of basic species at about less than 5%, or preventing the level of basic species from exceeding 5%. In some embodiments, the method further comprises maintaining the level of basic species at about less than 4%, or preventing the level of basic species from exceeding 4%. In some embodiments, the method further comprises maintaining the level of basic species at about less than 3%, or preventing the level of basic species from exceeding 3%. In some embodiments, the method further comprises maintaining the level of basic species at about less than 2%, or preventing the level of basic species from exceeding 2%.

In some embodiments, the method further comprises maintaining the level of main species at about 40-75%, or preventing the level of main species from dropping below 40%. In some embodiments, the method further comprises maintaining the level of main species at about 55-75%, or preventing the level of main species from dropping below 55%. In some embodiments, the method further comprises maintaining the level of main species at about 55-75%, or preventing the level of main species from dropping below 60%.

In certain embodiments, the present invention is directed to a method of producing a composition comprising an anti-IL-1R1 antibody, or antigen-binding portion thereof, having less than about 10%, about 9%, about 8%, about 7%, about 6%, about 5%, about 4%, about 3%, or about 2.5% or about 2% high molecular weight aggregates, the method comprising subjecting a sample comprising the anti-IL-1R1 antibody, or antigen-binding portion thereof, to a chromatography resin, wherein the chromatography resin is selected from a group consisting of a cation exchange chromatography resin and an anion exchange chromatography resin, or combinations thereof.

In certain embodiments, the present invention is directed to a method of producing a composition comprising an anti-IL-1R1 antibody, or antigen-binding portion thereof, having about 1-10% high molecular weight aggregates, the method comprising subjecting a sample comprising the anti-IL-1R1 antibody, or antigen-binding portion thereof, to a chromatography resin, wherein the chromatography resin is selected from a group consisting of a cation exchange chromatography resin and an anion exchange chromatography resin, or combinations thereof.

In some embodiments, the composition comprises about 1-10%, about 1-9%, about 1-8%, about 1-7%, about 1-6%, about 1-5%, about 1-4%, about 1-3.5%, or about 1-3% high molecular weight aggregates, and ranges within one or more of the preceding. In some embodiments, the composition comprises about 1-5% high molecular weight aggregates. In some embodiments, the composition comprises about 1-3.5% high molecular weight aggregates. In some embodiments, the composition comprises about 1-3% high molecular weight aggregates. In some embodiments, the composition comprises about 1-2% high molecular weight aggregates.

In some embodiments, the present invention provides a method of maintaining the level of high molecular weight aggregates at less than about 10%, about 9%, about 8%, about 7%, about 6%, about 5%, about 4%, about 3%, about 2.5%, or about 2% in a composition comprising an anti-IL-1R1 antibody, or antigen-binding portion thereof, the method comprising subjecting a sample comprising the anti-IL-1R1 antibody, or antigen-binding portion thereof, to a chromatography resin, wherein the chromatography resin is selected from a group consisting of a cation exchange chromatography resin and an anion exchange chromatography resin, or combinations thereof.

In some embodiments, the method maintains the level of high molecular weight aggregates in the composition at less about 9%, about 8%, about 7%, about 6%, about 5%, about 4%, or about 3%, or about 2.5%, or about 2%, and ranges within one or more of the preceding.

In some embodiments, the present invention provides a method of maintaining the level of high molecular weight aggregates at about 1-10% in a composition comprising an anti-IL-1R1 antibody, or antigen-binding portion thereof, the method comprising subjecting a sample comprising the anti-IL-1R1 antibody, or antigen-binding portion thereof, to a chromatography resin, wherein the chromatography resin is selected from a group consisting of a cation exchange chromatography resin and an anion exchange chromatography resin, or combinations thereof.

In some embodiments, the method maintains the level of high molecular weight aggregates in the composition at about 1-10%, about 1-9%, about 1-8%, about 1-7%, about 1-6%, about 1-5%, about 1-4%, about 1-3.5%. or about 1-3%, or about 1-2%, and ranges within one or more of the preceding. In some embodiments, the method maintains the level of high molecular weight aggregates in the composition at about 1-5%. In some embodiments, the method maintains the level of high molecular weight aggregates in the composition at about 1-3.5%. In some embodiments, the method maintains the level of high molecular weight aggregates in the composition at about 1-3%. In some embodiments, the method maintains the level of high molecular weight aggregates in the composition at about 1-2%.

In some embodiments, the present invention provides a method of preventing the level of high molecular weight aggregates from exceeding about 10%, about 9%, about 8%, about 7%, about 6%, about 5%, about 4%, about 3%, or about 2.5% in a composition comprising an anti-IL-1R1 antibody, or antigen-binding portion thereof, the method comprising subjecting a sample comprising the anti-IL-1R1 antibody, or antigen-binding portion thereof, to a chromatography resin, wherein the chromatography resin is selected from a group consisting of a cation exchange chromatography resin and an anion exchange chromatography resin, or combinations thereof.

In some embodiments, the method prevents the level of high molecular weight aggregates from exceeding about 9%, about 8%, about 7%, about 6%, about 5%, about 4%, about 3%, or about 2.5% in the composition.

In certain embodiments, the method further comprises maintaining the level of antibody monomer at about 90-99.9%, or preventing the level of antibody monomer from dropping below 90%.

In some embodiments, the present invention provides a method of producing a composition comprising an anti-IL-1R1 antibody, or antigen-binding portion thereof, having more than about 90%, about 91%, about 92%, about 93%, about 94%, about 95%, about 96%, about 97%, about 98%, or about 99% antibody monomer, the method comprising subjecting a sample comprising the anti-IL-1R1 antibody, or antigen-binding portion thereof, to a chromatography resin, wherein the chromatography resin is selected from a group consisting of a cation exchange chromatography resin and an anion exchange chromatography resin, or combinations thereof, thereby producing the composition comprising the anti-IL-1R1 antibody, or antigen-binding portion thereof, having more than about 90%, about 91%, about 92%, about 93%, about 94%, about 95%, about 96%, about 97%, about 98%, or about 99% antibody monomer.

In some embodiments, the present invention provides a method of producing a composition comprising an anti-IL-1R1 antibody, or antigen-binding portion thereof, having about 90-99.9%, about 90-99%, about 95-99%, about 96-99%, about 96-99.5%, about 97-99%, or about 98-99% antibody monomer, the method comprising subjecting a sample comprising the anti-IL-1R1 antibody, or antigen-binding portion thereof, to a chromatography resin, wherein the chromatography resin is selected from a group consisting of a cation exchange chromatography resin and an anion exchange chromatography resin, or combinations thereof, thereby producing the composition comprising the anti-IL-1R1 antibody, or antigen-binding portion thereof, having about 90-99.9%, about 90-99%, about 95-99%, about 96-99%, about 96-99.5%, about 97-99%, or about 98-99% antibody monomer.

In some embodiments, the present invention provides a method of maintaining the level of antibody monomer at more than about 90%, about 91%, about 92%, about 93%, about 94%, about 95%, about 96%, about 97%, about 98%, or about 99% in a composition comprising an anti-IL-1R1 antibody, or antigen-binding portion thereof, the method comprising subjecting a sample comprising the anti-IL-1R1 antibody, or antigen-binding portion thereof, to a chromatography resin, wherein the chromatography resin is selected from a group consisting of a cation exchange chromatography resin and an anion exchange chromatography resin, or combinations thereof, thereby maintaining the level of antibody monomer at more than about 90%, about 91%, about 92%, about 93%, about 94%, about 95%, about 96%, about 97%, about 98%, or about 99% in the composition.

In some embodiments, the present invention provides a method of maintaining the level of antibody monomer at about 90-99.9%, about 90-99%, about 95-99%, about 96-99.5%, about 96-99%, about 97-99%, or about 98-99% in a composition comprising an anti-IL-1R1 antibody, or antigen-binding portion thereof, the method comprising subjecting a sample comprising the anti-IL-1R1 antibody, or antigen-binding portion thereof, to a chromatography resin, wherein the chromatography resin is selected from a group consisting of a cation exchange chromatography resin and an anion exchange chromatography resin, or combinations thereof, thereby maintaining the level of antibody monomer at about 90-99.9%, about 90-99%, about 95-99%, about 96-99.5%, about 96-99%, about 97-99%, or about 98-99% in the composition.

In some embodiments, the present invention provides a method of preventing the level of antibody monomer from dropping below about 90%, about 91%, about 92%, about 93%, about 94%, about 95%, about 96%, about 97%, about 98%, or about 99% in a composition comprising an anti-IL-1R1 antibody, or antigen-binding portion thereof, the method comprising subjecting a sample comprising the anti-IL-1R1 antibody, or antigen-binding portion thereof, to a chromatography resin, wherein the chromatography resin is selected from a group consisting of a cation exchange chromatography resin and an anion exchange chromatography resin, or combinations thereof, thereby preventing the level of antibody monomer from dropping below about 90%, about 91%, about 92%, about 93%, about 94%, about 95%, about 96%, about 97%, about 98%, or about 99% in the composition comprising the anti-IL-1R1 antibody, or antigen-binding portion thereof.

In some embodiments, the method prevents the level of antibody monomer from dropping below about 91%, about 92%, about 93%, about 94%, about 95%, about 96%, about 97%, about 98%, or about 99% in the composition.

In some embodiments, the method further comprises maintaining the level of high molecular weight aggregates at about 1-10%, or preventing the level of high molecular weight aggregates from exceeding about 10%.

In certain embodiments, the compositions of the present invention may be produced using the downstream process technologies (e.g., purification), as described herein, following cell culture of a protein.

In one embodiment, the downstream process technologies described herein produce a composition comprises an antibody or antigen-binding portion thereof, for example, an anti-IL-1R1 antibody such as KPL-387, having a consistently low level of variants, e.g., a consistently low level of product-related substances, e.g., protein aggregates, or charged species (for example, acidic species or basic species).

In some embodiments, the methods result in a composition comprising an antibody or antigen-binding portion thereof, for example, an anti-IL-1R1 antibody such as KPL-387, wherein the composition comprises less than about 55%, about 54%, about 53%, about 52%, about 51%, about 50%, about 49%, about 48%, about 47%, about 46%, about 45%, about 44%, about 43%, about 42%, about 41%, about 40%, about 39%, about 38%, about 37%, about 36%, about 35%, about 34%, about 34.5%, about 33%, about 32%, about 31%, about 30%, about 29%, about 28%, about 27%, about 26%, about 25%, about 24%, about 23%, about 22%, about 21%, about 20%, about 19%, about 18%, about 17%, about 16%, about 15%, about 14%, about 13%, about 12%, about 11%, or about 10% acidic species of the antibody, and ranges within one or more of the preceding. In some embodiments, the composition comprises less than about 55% acidic species. In some embodiments, the composition comprises less than about 40% acidic species. In another embodiment, the composition comprises less than 39% acidic species. In another embodiment, the composition comprises less than 38% acidic species. In another embodiment, the composition comprises less than 37% acidic species. In another embodiment, the composition comprises less than 36% acidic species. In another embodiment, the composition comprises less than 35% acidic species. In another embodiment, the eluate fraction comprises less than 34.5% acidic species. In another embodiment, the eluate fraction comprises less than 34% acidic species.

In some embodiments, the methods result in a composition comprising an antibody or antigen-binding portion thereof, for example, an anti-IL-1R1 antibody such as KPL-387, wherein the composition comprises about 30-55%, about 31-55%, about 32-55%, about 33-55%, about 34-55%, about 35-55%, about 30-40%, about 31-40%, about 32-40%, about 33-40%, about 34-40%, about 35-40%, about 31-39%, about 31-38%, about 31-37%, about 31-36%, about 32-39%, about 32-38%, about 32-37%, about 32-36%, about 33-39%, about 33-38%, about 33-37%, about 33-36%, about 34-39%, about 34-38%, about 34-37%, or about 34-36% of the acidic species, and ranges within one or more of the preceding. In some embodiments, the composition comprises about 30-55% acidic species. In some embodiments, the composition comprises about 30-40% acidic species. In some embodiments, the composition comprises about 34-36% acidic species.

In some embodiments, the methods result in a composition comprising an antibody or antigen-binding portion thereof, for example, an anti-IL-1R1 antibody such as KPL-387, wherein the composition comprises less than about 15%, about 14%, about 13%, about 12%, about 11%, about 10%, about 9%, about 8%, about 7%, about 6%, about 5%, about 4.5%, about 4%, about 3%, about 2%, or about 1% of the basic species, and ranges within one or more of the preceding. In some embodiments, the composition comprises less than about 15% basic species. In some embodiments, the composition comprises less than about 14% basic species. In some embodiments, the composition comprises less than about 13% basic species. In some embodiments, the composition comprises less than about 12% basic species. In some embodiments, the composition comprises less than about 11% basic species. In some embodiments, the composition comprises less than about 10% basic species. In some embodiments, the composition comprises less than about 5% basic species. In some embodiments, the composition comprises less than about 4% basic species. In some embodiments, the composition comprises less than about 3% basic species. In some embodiments, the composition comprises less than about 2% basic species.

In some embodiments, the methods result in a composition comprising an antibody or antigen-binding portion thereof, for example, an anti-IL-1R1 antibody such as KPL-387, wherein the composition comprises about 0.1-10%, about 0.1-9%, about 0.1-8%, about 0.1-7%, about 0.1-6%, about 0.1-5%, about 0.1-4%, about 0.1-3%, about 0.1-2%, about 1-15%, about 1-14%, about 1-13%, about 1-12%, about 1-11%, about 1-10%, about 1-9%, about 1-8%, about 1-7%, about 1-6%, about 1-5%, about 2-5%, about 2-4%, about 4.5-5.5%, about 1-4%, about 1-3%, or about 1-2% of the basic species, and ranges within one or more of the preceding. In some embodiments, the composition comprises about 0.1-10% basic species. In some embodiments, the composition comprises about 1-15% basic species. In some embodiments, the composition comprises about 1-10% basic species. In some embodiments, the composition comprises about 1-5% basic species. In some embodiments, the composition comprises about 2-4% basic species. In some embodiments, the composition comprises about 1-4% basic species.

In some embodiments, the methods result in a composition comprising an antibody or antigen-binding portion thereof, for example, an anti-IL-1R1 antibody such as KPL-387, wherein the composition comprises more than about 40%, about 41%, about 42%, about 43%, about 44%, about 45%, about 46%, about 47%, about 48%, about 49%, about 50%, about 55%, about 60%, about 61%, about 62%, about 63%, about 64%, about 65%, about 66%, about 67%, about 68%, about 69%, about 70%, about 75%, about 80%, about 85%, about 90%, about 95% or about 99% main species of the antibody, and ranges within one or more of the preceding. In a particular embodiment, the composition comprises more than 40% main species. In a particular embodiment, the composition comprises more than 55% main species. In a particular embodiment, the composition comprises more than 56% main species. In a particular embodiment, the composition comprises more than 57% main species. In a particular embodiment, the composition comprises more than 58% main species. In a particular embodiment, the composition comprises more than 59% main species. In another embodiment, the composition comprises more than 60% main species. In another embodiment, the composition comprises more than 61% main species. In another embodiment, the composition comprises more than 62% main species.

In some embodiments, the methods result in a composition comprising an antibody or antigen-binding portion thereof, for example, an anti-IL-1R1 antibody such as KPL-387, wherein the composition comprises about 40-75%, about 40-70%, about 40-65%, about 40-60%, about 40-55%, about 40-50%, about 55-95%, about 55-85%, about 55-75%, about 55-70%, about 60-70%, about 60-65%, or about 60-63% main species of the antibody, and ranges within one or more of the preceding. In some embodiments, the composition comprises about 40-75% main species. In some embodiments, the composition comprises about 55-75% main species. In some embodiments, the composition comprises about 60-63% main species.

In some embodiments, the methods result in a composition comprising an antibody or antigen-binding portion thereof, for example, an anti-IL-1R1 antibody such as KPL-387, wherein the composition comprises about 30-55% acidic species, about 1-15% basic species, and/or about 40-75% main species.

In some embodiments, the methods result in a composition comprising an antibody or antigen-binding portion thereof, for example, an anti-IL-1R1 antibody such as KPL-387, wherein the composition comprises about 30-40% acidic species, about 1-5% basic species, and/or about 55-75% main species.

In some embodiments, the methods result in a composition comprising an antibody or antigen-binding portion thereof, for example, an anti-IL-1R1 antibody such as KPL-387, wherein the composition comprises about 34-36% acidic species, about 1-5% basic species, and/or about 60-63% main species.

In some embodiments, the methods result in a composition comprising an antibody or antigen-binding portion thereof, for example, an anti-IL-1R1 antibody such as KPL-387, wherein the composition comprises less than about 10%, about 9%, about 8%, about 7%, about 6%, about 5%, about 4%, about 3%, about 2%, or about 1% high molecular weight aggregates, and ranges within one or more of the preceding. In some embodiments, the composition comprises less than about 4% high molecular weight aggregates. In some embodiments, the composition comprises less than about 3% high molecular weight aggregates. In some embodiments, the composition comprises less than about 2% high molecular weight aggregates.

In some embodiments, the methods result in a composition comprising an antibody or antigen-binding portion thereof, for example, an anti-IL-1R1 antibody such as KPL-387, wherein the composition comprises about 1-10%, about 1-9%, about 1-8%, about 1-7%, about 1-6%, about 1-5%, about 1-4%, about 1-3.5%, about 1-3%, or about 1-2% high molecular weight aggregates, and ranges within one or more of the preceding. In some embodiments, the composition comprises about 1-10% high molecular weight aggregates. In some embodiments, the composition comprises about 1-3.5% high molecular weight aggregates. In some embodiments, the composition comprises about 1-3% high molecular weight aggregates. In some embodiments, the composition comprises about 1-2% high molecular weight aggregates.

In some embodiments, the methods result in a composition comprising an antibody or antigen-binding portion thereof, for example, an anti-IL-1R1 antibody such as KPL-387, wherein the composition comprises more than about 90%, about 91%, about 92%, about 93%, about 94%, about 95%, about 96%, about 97%, about 98%, or about 99% antibody monomer. In some embodiments, the composition comprises more than about 96% antibody monomer. In some embodiments, the composition comprises more than about 97% antibody monomer. In some embodiments, the composition comprises more than about 98% antibody monomer. In some embodiments, the composition comprises more than about 99% antibody monomer.

In some embodiments, the methods result in a composition comprising an antibody or antigen-binding portion thereof, for example, an anti-IL-1R1 antibody such as KPL-387, wherein the composition comprises about 90-99.9%, about 90-99%, about 95-99%, about 96-99%, about 96.5-99%, about 97-99%, or about 98-99% antibody monomer, and ranges within one or more of the preceding. In some embodiments, the composition comprises about 90-99% antibody monomer. In some embodiments, the composition comprises about 96.5-99% antibody monomer. In some embodiments, the composition comprises about 97-99% antibody monomer.

Protein Purification

Following upstream production of a protein of interest, e.g., an antibody or antigen-binding portion thereof, for example, an anti-IL-1R1 antibody such as KPL-387, downstream process technologies can be used to purify the protein. For example, but not by way of limitation, once a clarified solution or mixture comprising the protein of interest, for example, an antibody or antigen binding fragment thereof, has been obtained, separation of the protein of interest from the protein variants, e.g., product-related substance, e.g., protein aggregates, fragments, or charged species, e.g., acidic species or basic species; and/or process-related impurities, e.g., host cell proteins, can be effected using a combination of different purification techniques, including, but not limited to, ion exchange separation steps, mixed mode separation steps, affinity separation steps, and hydrophobic interaction separation steps singularly or in combination. The separation steps separate mixtures of proteins on the basis of their charge, degree of hydrophobicity, or size, or any combination thereof, depending on the particular form of separation, including chromatographic separation. In one aspect of the invention, separation is performed using chromatography, including cationic, anionic, and hydrophobic interaction. Several different chromatography resins are available for each of these techniques, allowing accurate tailoring of the purification scheme to the particular protein involved. Each of the separation methods result in the protein traversing at different rates through a column, to achieve a physical separation that increases as they pass further through the column, or adhere selectively to the separation medium. The proteins are then differentially eluted by different elution buffers. In some cases, the protein of interest is separated from variants and/or impurities when the variants and/or impurities preferentially adhere to the column's resin and the protein of interest does not, i.e., the protein of interest is present in the flow through fraction, while in other cases the protein of interest will adhere to the column's resin, while the variants and/or impurities are extruded from the column's resin during a wash cycle.

In certain embodiments, a composition of the present invention comprising a protein of interest, e.g., an antibody or antigen-binding portion thereof, for example, an anti-IL-1R1 antibody such as KPL-387, is produced using chromatographic separation to identify the particular conditions, e.g., salt concentration, pH, buffer, temperature, load amount and conditions, washing conditions, and elution condition, sufficient to elicit the desired fractionation profiles, e.g., fractionation of product-related substances, e.g., protein aggregates, fragments, or charged species, e.g., acidic species or basic species; and/or process-related impurities, e.g., host cell proteins, of a sample comprising the protein of interest and at least one such variants and/or impurities. In certain embodiments, the method further comprises pooling the resulting fractions comprising the desired compositions.

Primary Recovery and Virus Inactivation

In certain embodiments, the initial steps of the purification methods of the present invention involve the clarification and primary recovery of the protein of interest, e.g., an antibody or antigen-binding portion thereof, for example, an anti-IL-1R1 antibody such as KPL-387, from a sample matrix. In certain embodiments, the primary recovery will include one or more centrifugation steps to separate the protein of interest from the cells and cell debris. Centrifugation of the sample can be performed at, for example, but not by way of limitation, 7,000 g to approximately 12,750 g. In the context of large scale purification, such centrifugation can occur on-line with a flow rate set to achieve, for example, but not by way of limitation, a turbidity level of 150 NTU in the resulting supernatant. Such supernatant can then be collected for further purification, or in-line filtered through one or more depth filters for further clarification of the sample.

In certain embodiments, the primary recovery will include the use of one or more depth filtration steps to clarify the sample matrix and thereby aid in purifying the antibodies of interest in the present invention. In other embodiments, the primary recovery will include the use of one or more depth filtration steps post centrifugation to further clarify the sample matrix. Non-limiting examples of depth filters that can be used in the context of the instant invention include the Millistak+ X0HC, F0HC, D0HC, A1HC, B1HC depth filters (EMD Millipore), Cuno™ model 30/60ZA, 60/90 ZA, VR05, VR07, delipid depth filters (3M Corp.). A 0.2 µm filter such as Sartorius's 0.45/0.2 µm Sartopore™ bi-layer or Millipore's Express SHR or SHC filter cartridges typically follows the depth filters.

In certain embodiments, the primary recovery process can also be a point at which to reduce or inactivate viruses that can be present in the sample matrix. For example, any one or more of a variety of methods of viral reduction/inactivation can be used during or after the primary recovery phase of purification including heat inactivation (pasteurization), pH inactivation, buffer/detergent treatment, UV and γ-ray irradiation and the addition of certain chemical inactivating agents such as β-propiolactone or e.g., copper phenanthroline as described in U.S. Pat. No. 4,534,972. In certain embodiments of the present invention, the sample matrix is exposed to detergent viral inactivation during or after the primary recovery phase. In other embodiments, the sample matrix may be exposed to low pH inactivation during or after the primary recovery phase.

In those embodiments where viral reduction/inactivation is employed, the sample mixture can be adjusted, as needed, for further purification steps. For example, following low pH viral inactivation, the pH of the sample mixture is typically adjusted to a more neutral pH, e.g., from about 4.5 to about 8.5, from about 5 to about 8, from about 5.5 to about 7.5, or from about 6 to about 7, prior to continuing the purification process. Additionally, the mixture may be diluted with water for injection (WFI) to obtain a desired conductivity.

Affinity Chromatography

It is advantageous to subject a sample produced by the techniques of the instant invention to affinity chromatography to further purify the protein of interest, e.g., an antibody or antigen-binding portion thereof, for example, an anti-IL-1R1 antibody such as KPL-387, away from variants and/or impurities. In certain embodiments the chromatographic material is capable of selectively or specifically binding to the protein of interest ("capture"). Non-limiting examples of such chromatographic material include: Protein A, Protein G, chromatographic material comprising, for example, an antigen bound by an antibody of interest, and chromatographic material comprising an Fc binding protein. In specific embodiments, the affinity chromatography step involves subjecting the primary recovery sample to a column comprising a suitable Protein A resin. In certain embodiments, Protein A resin is useful for affinity purification and isolation of a variety of antibody isotypes, particularly IgG1, IgG2, and IgG4. Protein A is a bacterial cell wall protein that binds to mammalian IgGs primarily through their Fc regions. In its native state, Protein A has five IgG binding domains as well as other domains of unknown function.

There are several commercial sources for Protein A resin. Suitable resins include, but not limited to, MabSelect PrismA, Amsphere A3, Gore membrane, MabSelect SuRe LX, MabSelect SuRe™, MabSelect, MabSelect Xtra, Protein A Sepharose, ProSep HC, ProSep Ultra, ProSep Ultra Plus, and MapCapture.

The Protein A column can be equilibrated with a suitable buffer prior to sample loading. Following the loading of the column, the column can be washed one or multiple times using a suitable set of buffers. The Protein A column can then be eluted using an appropriate elution buffer. For example, glycine-HCL or citric acid can be used as an elution buffer. The eluate can be monitored using techniques well known to those skilled in the art. The eluate fractions of interest can be collected and then prepared for further processing.

The Protein A eluate may subject to a viral inactivation step either by detergent or low pH, provided this step is not performed prior to the Protein A capture operation. A proper detergent concentration or pH and time can be selected to obtain desired viral inactivation results. After viral inactivation, the Protein A eluate is usually pH and/or conductivity adjusted for subsequent purification steps.

The Protein A eluate may be subjected to filtration through a depth filter to remove turbidity and/or various impurities from the antibody of interest prior to additional chromatographic polishing steps. Examples of depth filters include, but not limited to, Millistak+X0HC, F0HC, D0HC, A1HC, and B1HC Pod filters (EMD Millipore), or Zeta Plus 30ZA/60ZA, 60ZA/90ZA, delipid, VR07, and VR05 filters (3M). The Protein A eluate pool may need to be conditioned to proper pH and conductivity to obtain desired impurity removal and product recovery from the depth filtration step.

The invention is not limited to capture of the protein of interest using Protein A chromatography. A non-Protein A chromatography capture step can also be carried out. For example, cation exchange capture and non-chromatographic methods, such as aqueous two phase extraction or precipitation, or other methods known in the art, can be used.

Cation Exchange Chromatography

The compositions of the present invention comprising a protein of interest, e.g., an antibody or antigen-binding portion thereof, for example, an anti-IL-1R1 antibody such as KPL-387, can be produced by subjecting a sample comprising a protein of interest, to a cation exchange (CEX) separation step. In certain embodiments, the CEX step occurs after the above-described affinity chromatography, e.g., Protein A affinity, step.

The use of a cationic exchange material versus an anionic exchange material, such as those anionic exchange materials discussed in detail herein, is based on the local charges of the protein of interest in a given solution. Thereof, it is within the scope of this invention to employ a cationic exchange step prior to the use of an anionic exchange step, or an anionic exchange step prior to the use of a cationic exchange step. Furthermore, it is within the scope of this invention to employ only a cationic exchange step, only an anionic exchange step, or any serial combination of the two (including serial combinations of one or both ion exchange steps with the other chromatographic separation technologies described herein).

In performing the separation, the initial protein mixture can be contacted with the cation exchange material by using any of a variety of techniques, e.g., using a batch purification technique or a chromatographic technique, as described above in connection with Protein A.

For example, in the context of batch purification, cation exchange material is prepared in, or equilibrated to, the desired starting buffer. Upon preparation, or equilibration, a slurry of the cation exchange material is obtained. In some embodiments, the protein of interest, e.g., antibody, solution is contacted with the CEX resin to allow for protein adsorption to the resin. The solution comprising the variants and/or impurities may not bind to the CEX resin. Alternatively, in other embodiments, the solution comprising the variants and/or impurities may bind tighter to the CEX resin than the protein of interest. The resin can be subjected to one or more washing steps and/or elution steps. Alternatively, the variants and/or impurities may bind to the resin, while the protein of interest does not.

A packed cation-exchange chromatography column, cation-exchange membrane device, cation-exchange monolithic device, or depth filter media can be operated either in bind-elute mode, flow-through mode, or a hybrid mode wherein the product exhibits binding to the chromatographic material, yet can be washed from the column using a buffer that is the same or substantially similar to the loading buffer. In the bind-elute mode, the column or the membrane device is first conditioned with a buffer with appropriate ionic strength and pH under conditions where certain proteins will be immobilized on the resin based matrix. For example, in certain embodiments, during the feed load, the protein of interest will be adsorbed to the resin due to electrostatic attraction. After washing the column or the membrane device with the equilibration buffer or another buffer with different pH and/or conductivity, the product recovery is achieved by increasing the ionic strength (i.e., conductivity) of the elution buffer to compete with the solute for the charged sites of the anion exchange matrix. Changing the pH and thereby altering the charge of the solute is another way to achieve elution of the solute. The change in conductivity or pH may be gradual (gradient elution) or stepwise (step elution). In the flow-through mode, the column or the membrane device is operated at selected pH and conductivity such that the protein of interest does not bind to the resin or the membrane while the acidic species will either be retained on the column or will have a distinct elution profile as compared to the protein of interest. In the context of this hybrid strategy, acidic species will bind to the chromatographic material (or Flow Through) in a manner distinct from the protein of interest, e.g., while the protein of interest and certain aggregates and/or fragments of the protein of interest may bind the chromatographic material, washes that preferentially remove the protein of interest can be applied. The column is then regenerated before next use.

In certain embodiments, in the context of chromatographic separation, a chromatographic apparatus, commonly cylindrical in shape, is employed to contain the chromatographic support material (e.g., CEX resin) prepared in an appropriate buffer solution. The chromatographic apparatus, if cylindrical, can have a diameter of about 5 mm to about 2 meters, and a height of 5 cm to 50 cm, and in certain embodiments, particularly for large scale processing, a height of ≤30 cm is employed. Once the chromatographic material is added to the chromatographic apparatus, a sample containing the protein of interest, e.g., an antibody, is contacted to the chromatographic resin to induce separation. Any portion of the solution that does not bind to the chromatographic resin, e.g., which may comprise the protein of interest or the variants and/or impurities, e.g., product-related substances, e.g., protein aggregates, fragments, charged variants, e.g. acidic or basic species, and/or process-related impurities, e.g., host cell proteins, depending on the CEX resin being employed, is separated from the chromatographic resin by washing the resin and collecting fractions. The chromatographic resin can be subjected to one or more wash steps. If desired, the chromatographic resin can then be contacted with a solution designed to desorb or elute any components of the solution that have bound to the chromatographic resin.

In certain embodiments, a wash step can be performed in the context of CEX chromatography using conditions similar to the load conditions or alternatively by changing the pH and/or the ionic strength/conductivity of the wash buffer in a step wise or linear gradient manner. The resulting flow through and wash fractions can be analyzed and appropriate fractions pooled to achieve the desired reduction in variants and/impurities.

In certain embodiments, the aqueous salt solution used as both the loading and wash buffer has a pH that is lower than the isoelectric point (pI) of the protein of interest. In certain embodiments, the pH of the loading and wash buffer is about 0 to 5 units lower than the pI of the protein. In certain embodiments, the pH of the loading and wash buffer is about 1 to 2 units lower than the pI of the protein. In certain embodiments, the pH of the loading and wash buffer is about 1 to 1.5 units lower than the pI of the protein.

In certain embodiments, the pH of the loading, wash or elution buffer used in the CEX method is about 3.5-10.5, about 4-10, about 4.5-9.5, about 5-9, abut 5.5-8.5, about 6-8, about 6.5-7.5, about 6-7, about 5-8, about 4-7, about 5-7, about 5.5-6.5, about 5.8-6.2, about 5.8-6.1, about 5.8-6.0, about 5-6, about 4.0-5.0, about 4.5-5, about 5.0-6.1, or about 5-5.5. In certain embodiments, the pH of the loading, wash or elution buffer is about 4.5, 4.6, 4.7, 4.8, 4.9, 5, 5.1, 5.15, 5.2, 5.25, 5.3, 5.35, 5.4, 5.45, 5.5, 5.55, 5.6, 5.65, 5.7, 5.75, 5.8, 5.85, 5.9, 5.95, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.5, 9, 9.5, or 10.

In one embodiment, the pH of the wash buffer is about 4-7, about 4.5-6.5, about 4.8-6.2, about 4.8-5.8, about 5-6, about 5.0-6.1, about 5.2-6.2. In one embodiment the pH of the elution buffer is greater than about 5.7. In one embodiment, the pH of the elution buffer is about 5.8-6.2, about 5.8-6.1, or about 5.8-6.0. In one embodiment, the pH of the elution buffer is about 5.8-6.1.

In one embodiment, the elution step is carried out at a pH of greater than about 5.7, e.g., a pH of about 5.8, about 5.9, about 6.0, or about 6.1. In one embodiment, the elution step is carried out at a pH of about 5.8-6.0. In one embodiment, the elution step is carried out at a pH of about 5.8-6.1.

In one embodiment, a wash buffer and/or an elution buffer are added to achieve a pH of greater than 5.7, e.g., a pH of about 5.8, about 5.9, or about 6.0, or about 6.1, during the elution step. In one embodiment, a wash buffer and/or an elution buffer are added to achieve a pH of about 5.8-6.0 during the elution step. In one embodiment, a wash buffer and/or an elution buffer are added to achieve a pH of about 5.8-6.1 during the elution step.

In one embodiment, a wash buffer of a pH about 4.8-5.8 is added during the CEX method. In another embodiment, an elution buffer of a pH about 6.2 is added. In a further embodiment, a wash buffer of a pH about 4.8-5.8 and an elution buffer of a pH about 6.2 are added to achieve a pH of greater than 5.7 or a pH of about 5.8-6.0 during the elution step.

In one embodiment, a wash buffer of a pH about 5-6 is added during the CEX method. In another embodiment, an elution buffer of a pH about 6 is added. In a further embodiment, a wash buffer of a pH about 5-6 and an elution buffer of a pH about 6 are added to achieve a pH of greater than 5.7 or a pH of about 5.8-6.0 during the elution step.

In one embodiment, a wash buffer of a pH about 5.2-6.2 is added during the CEX method. In another embodiment, an elution buffer of a pH about 5.8 is added. In a further embodiment, a wash buffer of a pH about 5.2-6.2 and an elution buffer of a pH about 5.8 are added to achieve a pH of greater than 5.7 or a pH of about 5.8-6.0 during the elution step.

Buffer systems suitable for use in the CEX methods include, but are not limited to sodium acetate, tris formate, tris acetate, ammonium sulfate, sodium chloride, and sodium sulfate. In certain embodiments, the conductivity and pH of the buffer is adjusted by increasing or decreasing the concentration of cationic or anionic agents. In certain non-limiting embodiments, the cationic agent is selected from the group consisting of sodium, Tris, tromethalmine, ammonium, arginine, histidine, or combinations thereof. In certain non-limiting embodiments, the anionic agent is selected from the group consisting of formate, acetate, citrate, chloride anion, sulphate, phosphate or combinations thereof.

In some embodiments, the wash buffer comprises about 500 mM, 490 mM, 480 mM, 470 mM, 460 mM, 450 mM, 440 mM, 430 mM, 420 mM, 410 mM, 400 mM, 390 mM, 380 mM, 370 mM, 360 mM, 350 mM, 340 mM, 330 mM, 320 mM, 310 mM, 300 mM, 290 mM, 280 mM, 270 mM, 260 mM, 250 mM, 240 mM, 230 mM, 220 mM, 210 mM, 200 mM, 190 mM, 180 mM, 170 mM, 160 mM, 150 mM, 140 mM, 130 mM, 120 mM, 110 mM, 100 mM, 90 mM, 85 mM, 80 mM, 75 mM, 70 mM, 65 mM, 60 mM, 55 mM, 50 mM, 45 mM, 40 mM, 35 mM, 30 mM, 25 mM, 20 mM, 15 mM, 10 mM or 5 mM sodium acetate. In some embodiments, the wash buffer comprises about 10 mM sodium acetate. In some embodiments, the wash buffer comprises about 20 mM sodium acetate. In some embodiments, the wash buffer comprises about 30 mM sodium acetate. In some embodiments, the wash buffer comprises about 40 mM sodium acetate. In some embodiments, the wash buffer comprises about 50 mM sodium acetate. In some embodiments, the wash buffer comprises about 60 mM sodium acetate. In some embodiments, the wash buffer comprises about 70 mM sodium acetate.

In some embodiments, the wash buffer comprises about 1-500 mM, about 10-100 mM, about 10-30 mM, about 20-50 mM, or about 40-70 mM, about 10-250 mM, about 50-200 mM, about 70-150 mM, about 90-130 mM, about 110-130 mM, about 110-120 mM, about 120-125 mM, about 10-150 mM, about 50-150 mM, or about 100-150 mM sodium acetate. In some embodiments, the wash buffer comprises about 20-50 mM sodium acetate. In some embodiments, the wash buffer comprises about 10-30 mM sodium acetate. In some embodiments, the wash buffer comprises about 40-70 mM sodium acetate.

In some embodiments, the wash buffer comprises about 20-50 mM sodium acetate, and a pH of about 5-6. In one embodiment, the wash buffer comprises about 50 mM sodium acetate, and a pH of about 5. In one embodiment, the wash buffer comprises about 20 mM sodium acetate, and a pH of about 6.

In some embodiments, the wash buffer comprises about 10-30 mM sodium acetate, and a pH of about 4.8-5.8. In one embodiment, the wash buffer comprises about 30 mM sodium acetate, and a pH of about 4.8. In one embodiment, the wash buffer comprises about 10 mM sodium acetate, and a pH of about 5.8.

In some embodiments, the wash buffer comprises about 40-70 mM sodium acetate, and a pH of about 5.2-6.2. In one embodiment, the wash buffer comprises about 70 mM sodium acetate, and a pH of about 5.2. In one embodiment, the wash buffer comprises about 40 mM sodium acetate, and a pH of about 6.2.

In some embodiments, the elution buffer comprises about 500 mM, 490 mM, 480 mM, 470 mM, 460 mM, 450 mM, 440 mM, 430 mM, 420 mM, 410 mM, 400 mM, 390 mM, 380 mM, 370 mM, 360 mM, 350 mM, 340 mM, 330 mM, 320 mM, 310 mM, 300 mM, 290 mM, 280 mM, 270 mM, 260 mM, 250 mM, 240 mM, 230 mM, 220 mM, 210 mM, 200 mM, 190 mM, 180 mM, 170 mM, 160 mM, 150 mM, 140 mM, 130 mM, 129 mM, 128 mM, 127 mM, 126 mM, 125 mM, 124 mM, 123 mM, 122 mM, 121 mM, 120 mM, 115 mM, 110 mM, 100 mM, 90 mM, 85 mM, 80 mM, 75 mM, 70 mM, 65 mM, 60 mM, 55 mM, 50 mM, 45 mM, 40 mM, 35 mM, 30 mM, 25 mM, 20 mM, 15 mM, 10 mM or 5 mM sodium acetate. In some embodiments, the elution buffer comprises about 110 mM sodium acetate. In some embodiments, the elution buffer comprises about 120 mM sodium acetate. In some embodiments, the elution buffer comprises about 130 mM sodium acetate.

In some embodiments, the elution buffer comprises about 1-500 mM, about 10-250 mM, about 50-200 mM, about 70-150 mM, about 90-130 mM, about 110-130 mM, about 110-120 mM, about 120-125 mM, about 10-150 mM, about 50-150 mM, or about 100-150 mM sodium acetate. In some embodiments, the elution buffer comprises about 100-150 mM sodium acetate. In some embodiments, the elution buffer comprises about 110-130 mM sodium acetate. In some embodiments, the elution buffer comprises about 110-129 mM sodium acetate.

In some embodiments, the elution buffer comprises about 110-130 mM sodium acetate, and a pH of about 5.8-6.2.

In some embodiments, the elution buffer comprises about 120 mM sodium acetate, and a pH of about 6.

In some embodiments, the elution buffer comprises about 110 mM sodium acetate, and a pH of about 5.8.

In some embodiments, the elution buffer comprises about 130 mM sodium acetate, and a pH of about 6.2.

In some embodiments, the elution buffer comprises about 110-129 mM sodium acetate, and a pH of about 5.8-6.1.

In some embodiments, the elution buffer comprises about 110-125 mM sodium acetate, and a pH of about 5.8-6.1.

In some embodiments, the elution buffer comprises about 110-120 mM sodium acetate, and a pH of about 5.8-6.0.

In some embodiments, the elution buffer comprises about 110-125 mM sodium acetate, and a pH of about 5.8-6.0

Any cation exchange chromatography resins known in the art are suitable for the preparation of the composition of the present invention. Exemplary CEX resins include, but are not limited to, sulphydryl (XS), sulfonate (S), sulfate, carboxymethyl (CM), sulfoethyl (SE), sulfopropyl (SP), phosphate (P) and sulfonate (S). In certain embodiments, the resin employed for a CEX separation is POROS™ XS. POROS™ XS is a strong cation exchanger of a support matrix of cross-linked poly(styrene-divinylbenzene) with a sulfopropyl functionality. In certain embodiments, the resin employed for a CEX separation is Capto™ S Impact. .Capto™ S Impact is a cation exchanger of a high-flow agarose matrix with a sulfonate group and a neutral pyrrolidone. In certain embodiments, the resin employed for a CEX separation is Toyopearl™ sulfate 650. Toyopearl™ sulfate 650 is a cation exchange resin of polymethacrylate beads with a proprietary sulfate containing ligand. In certain embodiments, the resin employed for a CEX separation is Toyopearl™ GigaGap CM 650M. Toyopearl™ CM GigaGap 650M is a cation exchange resin composed of polymethacrylate beads that have been chemically modified to provide a higher number of cationic binding sites and functionalized with carboxymethyl groups. Additional CEX resins include, but are not limited to, Capto™ SP ImpRes, CM™ Ceramic HyperD grade F, Eshmuno™ S, Nuvia™ C Prime, Nuvia™ 5, Poros™ HS; Poros™ XS, Poros™ HQ, Toyopearl™ GigaCap S 650M, Toyopearl™ sulfate 650F, and Toyopearl™ MX Trp 650M. It is noted that CEX chromatography can be used with MM resins, described herein.

In certain embodiments, the protein of interest, e.g., an antibody or antigen-binding portion thereof, for example, an anti-IL-1R1 antibody such as KPL-387, is loaded onto the cation exchange chromatography resin at a level of about about 10-120 g/L, about 20-110 g/L, about 30-1000 g/L, about 40-90 g/L, about 65-95 g/L, about 70-90 g/L or about 75-85 g/L. In certain embodiments, KPL-387 is loaded onto the cation exchange chromatography resin at a level of about 70-90 g/L. In certain embodiments, KPL-387 is loaded onto the cation exchange chromatography resin at a level of about 80-90 g/L. In certain embodiments, KPL-387 is loaded onto the cation exchange chromatography resin at a level of about 70-80 g/L. In certain embodiments, KPL-387 is loaded onto the cation exchange chromatography resin at a level of about 80 g/L.

In certain embodiments, the methods of the instant invention can be used to selectively remove, prevent the increase of, maintain the levels of, significantly reduce, or essentially remove all of, variants and/or impurities, e.g., product-related substances, e.g., protein aggregates, fragments, charged variants, e.g. acidic or basic species, and/or process-related impurities, e.g., Protein A, host cell proteins, impurities from the production of the protein of interest, wherein the impurities are variants and/or impurities, e.g., product-related substances, e.g., protein aggregates, fragments, charged variants, e.g. acidic or basic species, and/or process-related impurities, e.g., host cell proteins, are collected in the flow-through and wash fractions, and the protein of interest is enriched in the elution fraction.

In certain embodiments, the eluate fractions collected from the CEX chromatography step comprises a protein of interest, e.g., an antibody or antigen-binding portion thereof, for example, an anti-IL-1R1 antibody such as KPL-387.

In some embodiments, the eluate fraction comprising an antibody or antigen-binding portion thereof, for example, an anti-IL-1R1 antibody, such as KPL-387, collected following a cation exchange chromatography step, comprises less than about 55%, e.g., about 54%, about 53%, about 52%, about 51%, about 50%, about 49%, about 48%, about 47%, about 46%, about 45%, about 44%, about 43%, about 42%, about 41%, about 40%, about 39%, about 38%, about 37%, about 36%, about 35%, about 34.5%, about 34%, about 33%, about 32%, about 31%, about 30%, about 29%, about 28%, about 27%, about 26%, about 25%, about 24%, about 23%, about 22%, about 21%, about 20%, about 19%, about 18%, about 17%, about 16%, about 15%, about 14%, about 13%, about 12%, about 11%, or about 10% of the acidic species, and ranges within one or more of the preceding. In a particular embodiment, the eluate fraction comprises less than 55% acidic species. In a particular embodiment, the eluate fraction comprises less than 40% acidic species. In a particular embodiment, the eluate fraction comprises less than 39% acidic species. In a particular embodiment, the eluate fraction comprises less than 38% acidic species. In a particular embodiment, the eluate fraction comprises less than 37% acidic species. In another embodiment, the eluate fraction comprises less than 36% acidic species. In another embodiment, the eluate fraction comprises less than 35% acidic species. In another embodiment, the eluate fraction comprises less than 34.5% acidic species. In another embodiment, the eluate fraction comprises less than 34% acidic species.

In some embodiments, the eluate fraction comprising an antibody or antigen-binding portion thereof, for example, an anti-IL-1R1 antibody, such as KPL-387, collected following a cation exchange chromatography step, comprises about 30-55%, about 31-55%, about 32-55%, about 33-55%, about 34-55%, about 35-55%, about 30-40%, about 31-40%, about 32-40%, about 33-40%, about 34-40%, about 35-40%, about 31-39%, about 31-38%, about 31-37%, about 31-36%, about 32-39%, about 32-38%, about 32-37%, about 32-36%, about 33-39%, about 33-38%, about 33-37%, about 33-36%, about 34-39%, about 34-38%, about 34-37%, or about 34-36% of the acidic species, and ranges within one or more of the preceding. In some embodiments, the eluate fraction comprises about 30-55% acidic species. In some embodiments, the eluate fraction comprises about 30-40% acidic species. In some embodiments, the eluate fraction comprises about 34-36% acidic species.

In some embodiments, the eluate fraction comprising an antibody or antigen-binding portion thereof, for example, an anti-IL-1R1 antibody, such as KPL-387, collected following a cation exchange chromatography step, comprises less than about 15%, e.g., about 14%, about 13%, about 12%, about 11%, about 10%, about 9%, about 8%, about 7%, about 6%, about 5%, about 4.5%, about 4%, about 3%, about 2%, or about 1% of the basic species, and ranges within one or more of the preceding. In some embodiments, the eluate fraction comprises less than about 15% basic species. In some embodiments, the eluate fraction comprises less than about 10% basic species. In some embodiments, the eluate fraction comprises less than about 5% basic species. In some embodiments, the eluate fraction comprises less than about 4% basic species. In some embodiments, the eluate fraction comprises less than about 3% basic species. In some embodiments, the eluate fraction comprises less than about 2% basic species.

In some embodiments, the eluate fraction comprising an antibody or antigen-binding portion thereof, for example, an anti-IL-1R1 antibody, such as KPL-387, collected following a cation exchange chromatography step, comprises about 0.1-10%, about 0.1-9%, about 0.1-8%, about 0.1-7%, about 0.1-6%, about 0.1-5%, about 0.1-4%, about 0.1-3%, about 0.1-2%, or about 1-11%, or about 1-12%, or about 1-13%, or about 1-14%, or about 1-15%, about 1-10%, about 1-9%, about 1-8%, about 1-7%, about 1-6%, about 1-5%, about 2-5%, about 2-4%, about 4.5-5.5%, about 1-4%, about 1-3%, or about 1-2% of the basic species, and ranges within one or more of the preceding. In some embodiments, the eluate fraction comprises about 0.1-10% basic species. In some embodiments, the eluate fraction comprises about 1-15% basic species. In some embodiments, the eluate fraction comprises about 1-10% basic species. In some embodiments, the eluate fraction comprises about 1-5% basic species. In some embodiments, the eluate fraction comprises about 2-4% basic species. In some embodiments, the eluate fraction comprises about 1-4% basic species.

In some embodiments, the eluate fraction comprising an antibody or antigen-binding portion thereof, for example, an anti-IL-1R1 antibody, such as KPL-387, collected following a cation exchange chromatography step, comprises more than about 40%, e.g., about 41%, about 42%, about 43%, about 44%, about 45%, about 46%, about 47%, about 48%, about 49%, about 50%, about 55%, about 60%, about 61%, about 62%, about 63%, about 64%, about 65%, about 66%, about 67%, about 68%, about 69%, about 70%, about 75%, about 80%, about 85%, about 90%, about 95% or about 99% main species of the antibody, and ranges within one or more of the preceding. In a particular embodiment, the eluate fraction comprises more than 40% main species. In a particular embodiment, the eluate fraction comprises more than 55% main species. In another embodiment, the eluate fraction comprises more than 56% main species. In another embodiment, the eluate fraction comprises more than 57% main species. In another embodiment, the eluate fraction comprises more than 58% main species. In another embodiment, the eluate fraction comprises more than 59% main species. In another embodiment, the eluate fraction comprises more than 60% main species. In another embodiment, the eluate fraction comprises more than 61% main species. In another embodiment, the eluate fraction comprises more than 62% main species.

In some embodiments, the eluate fraction comprising an antibody or antigen-binding portion thereof, for example, an anti-IL-1R1 antibody, such as KPL-387, collected following a cation exchange chromatography step, comprises about 40-75%, about 40-70%, about 40-65%, about 40-60%, about 40-55%, about 40-50%, about 55-95%, about 55-85%, about 55-75%, about 55-70%, about 60-70%, about 60-65%, or about 60-63% main species of the antibody, and ranges within one or more of the preceding. In some embodiments, the eluate fraction comprises about 40-75% main species. In some embodiments, the eluate fraction comprises about 55-75% main species. In some embodiments, the eluate fraction comprises about 60-63% main species.

In some embodiments, the eluate fraction comprising an antibody or antigen-binding portion thereof, for example, an anti-IL-1R1 antibody, such as KPL-387, collected following a cation exchange chromatography step, comprises about 30-55% acidic species, about 1-15% basic species, and/or about 40-75% main species.

In some embodiments, the eluate fraction comprising an antibody or antigen-binding portion thereof, for example, an anti-IL-1R1 antibody, such as KPL-387, collected following a cation exchange chromatography step, comprises about 30-40% acidic species, about 1-5% basic species, and/or about 55-75% main species.

In some embodiments, the eluate fraction comprising an antibody or antigen-binding portion thereof, for example, an anti-IL-1R1 antibody, such as KPL-387, collected following a cation exchange chromatography step, comprises about 34-36% acidic species, about 1-5% basic species, and/or about 60-63% main species.

In some embodiments, the level of acidic species, the level of main species, or the level of basic species is determined by Imaging Capillary Isoelectric Focusing (iCIEF).

In some embodiments, the eluate fraction comprising an antibody or antigen-binding portion thereof, for example, an anti-IL-1R1 antibody, such as KPL-387, collected following a cation exchange chromatography step, comprises less than about 10%, about 9%, about 8%, about 7%, about 6%, about 5%, about 4%, about 3%, about 2.5%, about 2%, or about 1% high molecular weight aggregates, and ranges within one or more of the preceding. In some embodiments, the eluate fraction comprises less than about 4% high molecular weight aggregates. In some embodiments, the eluate fraction comprises less than about 3% high molecular weight aggregates. In some embodiments, the eluate fraction comprises less than about 2% high molecular weight aggregates. In some embodiments, the eluate fraction comprises less than about 4% high molecular weight aggregates and less than about 100 ppm of host cell proteins (HCP), and, optionally, less than about 1.6 ppm Protein A (ProA).

In some embodiments, the eluate fraction comprising an antibody or antigen-binding portion thereof, for example, an anti-IL-1R1 antibody, such as KPL-387, collected following a cation exchange chromatography step, comprises about 1-10%, about 1-9%, about 1-8%, about 1-7%, about 1-6%, about 1-5%, about 1-4%, about 1-3.5%, or about 1-3%, about 1-2.5%, or about 1-2% high molecular weight aggregates, and ranges within one or more of the preceding. In some embodiments, the eluate fraction comprises about 1-10% high molecular weight aggregates. In some embodiments, the eluate fraction comprises about 1-3.5% high molecular weight aggregates. In some embodiments, the eluate fraction comprises about 1-3% high molecular weight aggregates. In some embodiments, the eluate fraction comprises about 1-2% high molecular weight aggregates. In some embodiments, the eluate fraction comprises about 1-3% high molecular weight aggregates and less than about 100 ppm of host cell proteins (HCP), and, optionally, less than about 1.6 ppm Protein A (ProA).

In some embodiments, the eluate fraction comprising an antibody or antigen-binding portion thereof, for example, an anti-IL-1R1 antibody, such as KPL-387, collected following a cation exchange chromatography step, comprises more than about 90%, about 91%, about 92%, about 93%, about 94%, about 95%, about 96%, about 97%, about 98%, or about 99% antibody monomer. In some embodiments, the eluate fraction comprises more than about 96% antibody monomer. In some embodiments, the eluate fraction comprises more than about 97% antibody monomer. In some embodiments, the eluate fraction comprises more than about 98% antibody monomer. In some embodiments, the elution fraction comprises more than about 99% antibody monomer. In some embodiments, the eluate fraction comprises more than about 96% antibody monomer and less than about 100 ppm of host cell proteins (HCP), and, optionally, less than about 1.6 ppm Protein A (ProA).

In some embodiments, the eluate fraction comprising an antibody or antigen-binding portion thereof, for example, an anti-IL-1R1 antibody, such as KPL-387, collected following a cation exchange chromatography step, comprises about 90-99.9%, about 90-99%, about 95-99%, about 96-99%, about 96.5-99%, about 97-99%, or about 98-99% antibody monomer, and ranges within one or more of the preceding. In some embodiments, the eluate fraction comprises about 96.5-99% antibody monomer. In some embodiments, the eluate fraction comprises about 90-99% antibody monomer. In some embodiments, the eluate fraction comprises about 97-99% antibody monomer. In some embodiments, the eluate fraction comprises about 97-99% antibody monomer and less than about 100 ppm of host cell proteins (HCP), and, optionally, less than about 1.6 ppm Protein A (ProA).

In certain embodiments, the loading, pH, conductivity of the CEX chromatography step, as well as elution pH and/or conductivity, can be modified to achieve a desired distribution of variants and/or impurities away from the protein of interest, e.g., the antibody or antigen binding portion thereof, for example, an anti-IL-1R1 antibody such as KPL-387.

In certain embodiments, a CEX chromatographic separation can be performed and combinations of fractions can be pooled to achieve a combination of desired process-related impurity and/or product-relates substance levels, in addition to, or in place of merely modulating charge variant concentration.

In certain embodiments, spectroscopy methods such as UV, NIR, FTIR, Fluorescence, Raman may be used to monitor levels of variants and/or impurities, e.g., product-related substances, e.g., charge variants, aggregates, fragments of the protein of interest, and/or process-related impurities, e.g., host cell proteins, in an on-line, at-line or in-line mode, which can then be used to control the level of variants and/or impurities in the pooled material collected from the CEX effluent. In certain embodiments, on-line, at-line or in-line monitoring methods can be used either on the effluent line of the chromatography step or in the collection vessel, to enable achievement of the desired product quality/recovery. In certain embodiments, the UV signal can be used as a surrogate to achieve an appropriate product quality/recovery, wherein the UV signal can be processed appropriately, including, but not limited to, such processing techniques as integration, differentiation, moving average, such that normal process variability can be addressed and the target product quality can be achieved. In certain embodiments, such measurements can be combined with in-line dilution methods such that ion concentration/conductivity of the load/wash can be controlled by feedback and hence facilitate product quality control.

In certain embodiments, a combination of CEX and AEX methods can be used to prepare compositions of the invention comprising a protein of interest, e.g., an antibody or antigen-binding portion thereof, for example, an anti-IL-1R1 antibody such as KPL-387, including certain embodiments where one technology is used in a complementary/supplementary manner with another technology. In some embodiments, such a combination can be performed such that certain sub-species are removed predominantly by one technology, such that the combination provides the desired final composition/product quality. In some embodiments, such combinations include the use of additional chromatography, filtration, nanofiltration, ultrafiltration/diafiltration (UF/DF) steps so as to achieve the desired product quality.

Anion Exchange Chromatography

In certain embodiments, the compositions comprising a protein of interest, e.g., an antibody or antigen-binding portion thereof, for example, an anti-IL-1R1 antibody such as KPL-387, are produced by subjecting the sample comprising a protein of interest to an anion exchange separation step. In some embodiments, the anion exchange step occurs after the above-described affinity chromatography, e.g., Protein A affinity, step. In some embodiments, the anion exchange step occurs after the cation exchange step. In certain embodiments, the anion exchange step occurs before the cation exchange step.

The use of an anionic exchange material versus a cationic exchange material, such as those cation exchange materials discussed in detail above, is based on the local charges of the protein of interest in a given solution. Thereof, it is within the scope of this invention to employ an anionic exchange step prior to the use of a cationic exchange step, or a cationic exchange step prior to the use of an anionic exchange step. Furthermore, it is within the scope of this invention to employ only an anionic exchange step, only a cationic exchange step, or any serial combination of the two (including serial combinations of one or both ion exchange steps with the other chromatographic separation technologies described herein).

In performing the separation, the initial protein composition can be contacted with the anion exchange material by using any of a variety of techniques, e.g., using a batch purification technique or a chromatographic technique, as described above.

In certain embodiments, the aqueous salt solution used as both the loading and wash buffer has a pH at or near the isoelectric point (pI) of the protein of interest. In certain embodiments, the pH of the loading and wash buffer is about 0 to 2 units higher or lower than the pI of the protein of interest. In certain embodiments, the pH of the loading and wash buffer is about 0 to 0.5 units higher or lower than the pI of the protein of interest. In certain embodiments, the pH of the loading and wash buffer is at the pI of the protein of interest.

In certain embodiments, the pH of the loading, wash or elution buffer is about 3-10, about 4-10, about 4.5-9.5, about 5-9, abut 5.5-8.5, about 6-8, about 6.5-7.5, about 6-7, about 7-7.5, about 5-8, about 4-7, about 5-7, about 5-6, about 4.5-5, about 5-5.5, about 5.0-6.1, about 7-7.5, about 7-7.6, about 7.1-7.5, or about 7.2-7.4. In certain embodiments, the pH of the loading, wash or elution buffer is about 5, 5.1, 5.15, 5.2, 5.25, 5.3, 5.35, 5.4, 5.45, 5.5, 5.55, 5.6, 5.65, 5.7, 5.75, 5.8, 5.85, 5.9, 5.95, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.5, 9, 9.5, or 10.

Buffer systems suitable for use in the AEX methods include, but are not limited to pyridine, piperazine, L-histidine, Bis-tris, Bis-tris propane, imidazole, N-Ethylmorpholine, TEA (triethanolamine), Tris, Tris acetate, sodium acetate, Morpholine, N-Methyldiethanolamine, AMPD (2-amino-2-methyl-1,3-propanediol), diethanolamine, ethanolamine, AMP (2-amino-2-methyl-1-propaol), piperazine, 1,3-Diaminopropane, piperidine. In certain embodiments, the conductivity and pH of the buffer is adjusted by increasing or decreasing the concentration of cationic or anionic agents. In certain non-limiting embodiments, the cationic agent is selected from the group consisting of sodium, Tris, tromethalmine, ammonium, arginine, histidine, or combinations thereof. In certain non-limiting embodiments, the anionic agent is selected from the group consisting of formate, acetate, citrate, chloride anion, sulphate, phosphate or combinations thereof.

In some embodiments, the loading buffer comprises about 500 mM, 490 mM, 480 mM, 470 mM, 460 mM, 450 mM, 440 mM, 430 mM, 420 mM, 410 mM, 400 mM, 390 mM, 380 mM, 370 mM, 360 mM, 350 mM, 340 mM, 330 mM, 320 mM, 310 mM, 300 mM, 290 mM, 280 mM, 270 mM, 260 mM, 250 mM, 240 mM, 230 mM, 220 mM, 210 mM, 200 mM, 190 mM, 180 mM, 170 mM, 160 mM, 150 mM, 140 mM, 130 mM, 120 mM, 110 mM, 100 mM, 90 mM, 85 mM, 80 mM, 75 mM, 70 mM, 65 mM, 60 mM, 55 mM, 50 mM, 45 mM, 40 mM, 35 mM, 30 mM, 25 mM, 20 mM, 15 mM, 10 mM or 5 mM Tris acetate. In some embodiments, the loading buffer comprises about 20 mM Tris acetate. In some embodiments, the loading buffer comprises about 1-500 mM, about 10-250 mM, about 10-150 mM, about 10-100 mM, about 20-90 mM, about 30-80 mM, about 40-70 mM, or about 50-60 mM, about 40-60 mM, about 10-30 mM, or about 15-25 mM Tris acetate. In some embodiments, the loading buffer comprises about 40-60 mM Tris acetate.

A packed anion-exchange chromatography column, anion-exchange membrane device, anion-exchange monolithic device, or depth filter media can be operated either in bind-elute mode, flow-through mode, or a hybrid mode wherein the product exhibits binding to the chromatographic material, yet can be washed from the column using a buffer that is the same or substantially similar to the loading buffer. In the bind-elute mode, the column or the membrane device is first conditioned with a buffer with appropriate ionic strength and pH under conditions where certain proteins will be immobilized on the resin based matrix. For example, in certain embodiments, during the feed load, the protein of interest will be adsorbed to the resin due to electrostatic attraction. After washing the column or the membrane device with the equilibration buffer or another buffer with different pH and/or conductivity, the product recovery is achieved by increasing the ionic strength (i.e., conductivity) of the elution buffer to compete with the solute for the charged sites of the anion exchange matrix. Changing the pH and thereby altering the charge of the solute is another way to achieve elution of the solute. The change in conductivity or pH may be gradual (gradient elution) or stepwise (step elution). In the flow-through mode, the column or the membrane device is operated at selected pH and conductivity such that the protein of interest does not bind to the resin or the membrane while the acidic species will either be retained on the column or will have a distinct elution profile as compared to the protein of interest. In the context of this hybrid strategy, acidic species will bind to the chromatographic material (or Flow Through) in a manner distinct from the protein of interest, e.g., while the protein of interest and certain aggregates and/or fragments of the protein of interest may bind the chromatographic material, washes that preferentially remove the protein of interest can be applied. The column is then regenerated before next use.

Any anion exchange chromatography resins known in the art are suitable for the preparation of the composition of the present invention. Non-limiting examples of AEX resin include diethylaminoethyl (DEAE), quaternary aminoethyl (QAE) and quaternary amine (Q) groups. In certain embodiments, the resin employed for an AEX separation is POROS™ XQ. POROS™ XQ is a strong anion exchanger of a support matrix of cross-linked poly(styrene-divinylbenzene) functionalized with quaternary amines. In certain embodiments, the resin employed for an AEX separation is Capto™ Q ImRes. Capto™ Q™ ImRes is a strong anion exchanger of high-flow agarose resin functionalized with quaternary amines. Additional non-limiting examples include: Sartobind Q, POROS™ HQ, Fractogel TMAE, Q sepharose Fast Flow, POROS™ 50PI, POROS™ 50HQ, Capto™ DEAE, Toyopearl™ QAE-550, Toyopearl™ DEAE-650, Toyopearl™ GigaCap Q-650, Fractogel® EMD TMAE Hicap, Sartobind STIC® PA nano, Sartobind Q nano; CUNO™ BioCap and X0HC.

In certain embodiments, the protein of interest, e.g., an antibody or antigen-binding portion thereof, for example, an anti-IL-1R1 antibody such as KPL-387, is loaded onto the anion exchange chromatography resin at a level of about 1-10 g/mL membrane volume (MV), about 2-9 g/mL MV, about 3-8 g/mL MV, about 3-6 g/mL MV, about 2.5-5 g/mL MV, about 3-5 g/mL MV or about 3.5-5 g/mL MV. In certain embodiments, the protein of interest is loaded onto the anion exchange chromatography resin at a level of about 3.5-5 g/mL MV. In certain embodiments, the protein of interest is loaded onto the anion exchange chromatography resin at a level of about 3.5 g/mL MV.

In certain embodiments, the methods of the instant invention can be used to selectively remove, prevent the increase of, maintain the levels of, significantly reduce, or essentially remove all of variants and/or impurities, e.g., product-related substances, e.g., protein aggregates, fragments, charged variants, e.g. acidic or basic species, and/or process-related impurities, e.g., host cell proteins, from the protein of interest, e.g., an antibody or antigen-binding portion thereof, for example, an anti-IL-1R1 antibody such as KPL-387, wherein the variants and/or impurities, e.g., product-related substances, e.g., protein aggregates, fragments, e.g., half antibody, charged variants, e.g. acidic or basic species, and/or process-related impurities, e.g., host cell proteins, are collected in the eluate fractions, and the protein of interest is enriched in the Flow Through fractions.

In some embodiments, the flow-through fraction comprising an antibody or antigen-binding portion thereof, for example, an anti-IL-1R1 antibody, such as KPL-387, collected following an anion exchange chromatography step, comprises less than about 55%, e.g., about 54%, about 53%, about 52%, about 51%, about 50%, about 49%, about 48%, about 47%, about 46%, about 45%, about 44%, about 43%, about 42%, about 41%, about 40%, about 39%, about 38%, about 37%, about 36%, about 35%, about 34.5%, about 34%, about 33%, about 32%, about 31%, about 30%, about 29%, about 28%, about 27%, about 26%, about 25%, about 24%, about 23%, about 22%, about 21%, about 20%, about 19%, about 18%, about 17%, about 16%, about 15%, about 14%, about 13%, about 12%, about 11%, or about 10% of the acidic species, and ranges within one or more of the preceding. In a particular embodiment, the flow-through fraction comprises less than 55% acidic species. In a particular embodiment, the flow-through fraction comprises less than 40% acidic species. In another embodiment, the flow-through fraction comprises less than 39% acidic species. In another embodiment, the flow-through fraction comprises less than 38% acidic species. In another embodiment, the flow-through fraction comprises less than 37% acidic species. In another embodiment, the flow-through fraction comprises less than 36% acidic species. In another embodiment, the flow-through fraction comprises less than 35% acidic species. In another embodiment, the eluate fraction comprises less than 34.5% acidic species. In another embodiment, the eluate fraction comprises less than 34% acidic species.

In some embodiments, the flow-through fraction comprising an antibody or antigen-binding portion thereof, for example, an anti-IL-1R1 antibody, such as KPL-387, collected following an anion exchange chromatography step, comprises about 30-55%, about 31-55%, about 32-55%, about 33-55%, about 34-55%, about 35-55%, about 30-40%, about 31-40%, about 32-40%, about 33-40%, about 34-40%, about 35-40%, about 31-39%, about 31-38%, about 31-37%, about 31-36%, about 32-39%, about 32-38%, about 32-37%, about 32-36%, about 33-39%, about 33-38%, about 33-37%, about 33-36%, about 34-39%, about 34-38%, about 34-37%, or about 34-36% of the acidic species, and ranges within one or more of the preceding. In some embodiments, the flow-through fraction comprises about 30-55% acidic species. In some embodiments, the flow-through fraction comprises about 30-40% acidic species. In some embodiments, the flow-through fraction comprises about 34-36% acidic species.

In some embodiments, the flow-through fraction comprising an antibody or antigen-binding portion thereof, for example, an anti-IL-1R1 antibody, such as KPL-387, collected following an anion exchange chromatography step, comprises less than about 15%, e.g., about 14%, about 13%, about 12%, about 11%, about 10%, about 9%, about 8%, about 7%, about 6%, about 5%, about 4%, about 3%, about 2%, or about 1% of the basic species, and ranges within one or more of the preceding. In some embodiments, the flow-through fraction comprises less than about 15% basic species. In some embodiments, the flow-through fraction comprises less than about 10% basic species. In some embodiments, the flow-through fraction comprises less than about 5% basic species. In some embodiments, the elua flow-through te fraction comprises less than about 4% basic species. In some embodiments, the elua flow-through te fraction comprises less than about 3% basic species. In some embodiments, the elua flow-through te fraction comprises less than about 2% basic species.

In some embodiments, the flow-through fraction comprising an antibody or antigen-binding portion thereof, for example, an anti-IL-1R1 antibody, such as KPL-387, collected following an anion exchange chromatography step, comprises about 0.1-10%, about 0.1-9%, about 0.1-8%, about 0.1-7%, about 0.1-6%, about 0.1-5%, about 0.1-4%, about 0.1-3%, about 0.1-2%, about 1-11%, about 1-12%, about 1-13%, about 1-14%, about 1-15%, about 1-10%, about 1-9%, about 1-8%, about 1-7%, about 1-6%, about 1-5%, about 2-5%, about 2-4%, about 1-4%, about 1-3%, or about 1-2% of the basic species, and ranges within one or more of the preceding. In some embodiments, the flow-through fraction comprises about 0.1-10% basic species. In some embodiments, the flow-through fraction comprises about 1-15% basic species. In some embodiments, the flow-through fraction comprises about 1-10% basic species. In some embodiments, the flow-through fraction comprises about 1-5% basic species. In some embodiments, the flow-through fraction comprises about 2-4% basic species. In some embodiments, the flow-through fraction comprises about 1-4% basic species.

In some embodiments, the flow-through fraction comprising an antibody or antigen-binding portion thereof, for example, an anti-IL-1R1 antibody, such as KPL-387, collected following an anion exchange chromatography step, comprises more than about 40%, e.g., about 41%, about 42%, about 43%, about 44%, about 45%, about 46%, about 47%, about 48%, about 49%, about 50%, about 55%, about 60%, about 61%, about 62%, about 63%, about 64%, about 65%, about 66%, about 67%, about 68%, about 69%, about 70%, about 75%, about 80%, about 85%, about 90%, about 95% or about 99% main species of the antibody, and ranges within one or more of the preceding. In a particular embodiment, the flow-through fraction comprises more than 40% main species. In a particular embodiment, the flow-through fraction comprises more than 55% main species. In another embodiment, the flow-through fraction comprises more than 56% main species. In another embodiment, the flow-through fraction comprises more than 57% main species. In another embodiment, the flow-through fraction comprises more than 58% main species. In another embodiment, the flow-through fraction comprises more than 59% main species. In another embodiment, the flow-through fraction comprises more than 60% main species. In another embodiment, the flow-through fraction comprises more than 61% main species. In another embodiment, the flow-through fraction comprises more than 62% main species.

In some embodiments, the flow-through fraction comprising an antibody or antigen-binding portion thereof, for example, an anti-IL-1R1 antibody, such as KPL-387, collected following an anion exchange chromatography step, comprises about 40-75%, about 40-70%, about 40-65%, about 40-60%, about 40-55%, about 40-50%, about 55-95%, about 55-85%, about 55-75%, about 55-70%, about 60-70%, about 60-65%, or about 60-63% main species of the antibody, and ranges within one or more of the preceding. In some embodiments, the flow-through fraction comprises about 40-75% main species. In some embodiments, the flow-through fraction comprises about 55-75% main species. In some embodiments, the flow-through fraction comprises about 60-63% main species.

In some embodiments, the flow-through fraction comprising an antibody or antigen-binding portion thereof, for example, an anti-IL-1R1 antibody, such as KPL-387, collected following an anion exchange chromatography step, comprises about 30-55% acidic species, about 1-15% basic species, and/or about 40-75% main species.

In some embodiments, the flow-through fraction comprising an antibody or antigen-binding portion thereof, for example, an anti-IL-1R1 antibody, such as KPL-387, collected following an anion exchange chromatography step, comprises about 30-40% acidic species, about 1-5% basic species, and/or about 55-75% main species.

In some embodiments, the flow-through fraction comprising an antibody or antigen-binding portion thereof, for example, an anti-IL-1R1 antibody, such as KPL-387, collected following an anion exchange chromatography step, comprises about 34-36% acidic species, about 1-5% basic species, and/or about 60-63% main species.

In some embodiments, the level of acidic species, the level of main species, or the level of basic species is determined by Imaging Capillary Isoelectric Focusing (iCIEF).

In some embodiments, the flow-through fraction comprising an antibody or antigen-binding portion thereof, for example, an anti-IL-1R1 antibody, such as KPL-387, collected following an anion exchange chromatography step, comprises less than about 10%, about 9%, about 8%, about 7%, about 6%, about 5%, about 4%, about 3%, about 2%, or about 1% high molecular weight aggregates, and ranges within one or more of the preceding. In some embodiments, the flow-through fraction comprises less than about 3% high molecular weight aggregates. In some embodiments, the flow-through fraction comprises less than about 2% high molecular weight aggregates.

In some embodiments, the flow-through fraction comprising an antibody or antigen-binding portion thereof, for example, an anti-IL-1R1 antibody, such as KPL-387, collected following an anion exchange chromatography step, comprises about 1-10%, about 1-9%, about 1-8%, about 1-7%, about 1-6%, about 1-5%, about 1-4%, about 1-3%, or about 1-2% high molecular weight aggregates, and ranges within one or more of the preceding. In some embodiments, the flow-through fraction comprises about 1-10% high molecular weight aggregates. In some embodiments, the flow-through fraction comprises about 1-3% high molecular weight aggregates. In some embodiments, the flow-through fraction comprises about 1-2% high molecular weight aggregates.

In some embodiments, the flow-through fraction comprising an antibody or antigen-binding portion thereof, for example, an anti-IL-1R1 antibody, such as KPL-387, collected following an anion exchange chromatography step, comprises more than about 90%, about 91%, about 92%, about 93%, about 94%, about 95%, about 96%, about 97%, about 98%, or about 99% antibody monomer. In some embodiments, the flow-through fraction comprises more than about 97% antibody monomer. In some embodiments, the flow-through fraction comprises more than about 98% antibody monomer. In some embodiments, the flow-through fraction comprises more than about 99% antibody monomer.

In some embodiments, the flow-through fraction comprising an antibody or antigen-binding portion thereof, for example, an anti-IL-1R1 antibody, such as KPL-387, collected following an anion exchange chromatography step, comprises about 90-99.9%, about 90-99%, about 95-99%, about 96-99%, about 97-99%, or about 98-99% antibody monomer, and ranges within one or more of the preceding. In some embodiments, the flow-through fraction comprises about 90-99% antibody monomer. In some embodiments, the flow-through fraction comprises about 97-99% antibody monomer.

In certain embodiments, the loading, pH, conductivity of the AEX chromatography step, as well as elution pH and/or conductivity, can be modified to achieve a desired distribution of variants and/or impurities away from the protein of interest, e.g., the antibody or antigen binding portion thereof, for example, an anti-IL-1R1 antibody such as KPL-387.

In certain embodiments, an AEX chromatographic separation can be performed and combinations of fractions can be pooled to achieve a combination of desired process-related impurity and/or product-relates substance levels, in addition to, or in place of merely modulating charge variant concentration.

In certain embodiments, spectroscopy methods such as UV, NIR, FTIR, Fluorescence, Raman may be used to monitor levels of variants and/or impurities, e.g., product-related substances, e.g., charge variants, aggregates, fragments of the protein of interest, and/or process-related impurities, e.g., host cell proteins, in an on-line, at-line or in-line mode, which can then be used to control the level of variants and/or impurities in the pooled material collected from the AEX effluent. In certain embodiments, on-line, at-line or in-line monitoring methods can be used either on the effluent line of the chromatography step or in the collection vessel, to enable achievement of the desired product quality/recovery. In certain embodiments, the UV signal can be used as a surrogate to achieve an appropriate product quality/recovery, wherein the UV signal can be processed appropriately, including, but not limited to, such processing techniques as integration, differentiation, moving average, such that normal process variability can be addressed and the target product quality can be achieved. In certain embodiments, such measurements can be combined with in-line dilution methods such that ion concentration/conductivity of the load/wash can be controlled by feedback and hence facilitate product quality control.

In certain embodiments, a combination of CEX and/or AEX methods can be used to prepare compositions of the invention comprising a protein of interest, e.g., an antibody or antigen-binding portion thereof, for example, an anti-IL-1R1 antibody such as KPL-387, including certain embodiments where one technology is used in a complementary/supplementary manner with another technology. In some embodiments, such a combination can be performed such that certain sub-species are removed predominantly by one technology, such that the combination provides the desired final composition/product quality. In some embodiments, such combinations include the use of additional chromatography, filtration, nanofiltration, ultrafiltration/diafiltration (UF/DF) steps so as to achieve the desired product quality.

Viral Filtration/Nanofiltration

Certain embodiments of the present invention employ nanofiltration steps to reduce the viral load and concentrate the protein of interest, e.g., an antibody, or antigen binding portion thereof, for example, an anti-IL-1R1 antibody such as KPL-387. Following the intermediate/final polishing chromatography step, the eluate pool may be subjected to a nanofiltration step. In an embodiment, the nanofiltration step is accomplished via one or more nanofilters or viral filters. In a particular embodiment, the nanofiltration step may be accomplished via a filter train comprised of a prefilter and a nanofilter or viral filters. The filters may be any known in the art to be useful for this purpose and may include, for example, EMD Millipore Viresolve VPro, Viresolve NFP, Viresolve NFR, Viresolve Pro Filter, Pellicon or Millipak filters, Sartorius Vivaspin, ViroStart CPV, or Sartopore filters, Pall Ultipor DVD, DV50, DV20 filtres, or Planova 15N, 20N, and 35N virus removal filters from Asashi Kasei Pharma. In certain embodiments, the nanofiltration filter has a mean pore size of between about 15 nm and about 200 nm. In a specific embodiment, the nanofilter may have a mean pore size of between about 15 nm and about 72 nm, or between about 19 nm and about 35 nm, or of at or about 15 nm, 19 nm, 35 nm, or 72 nm. One of skill in the art will understand that the selection of types and numbers of filters will be dependent on the volume of sample being processed and the desired filtration performance.

Ultrafiltration/Diafiltration

Certain embodiments of the present invention employ ultrafiltration and diafiltration steps to further concentrate and formulate the protein of interest, e.g., an antibody, or antigen binding portion thereof, for example, an anti-IL-1R1 antibody such as KPL-387. The nanofiltration step may be followed by ultrafiltration and diafiltration to achieve the targeted drug substance concentration and buffer condition before formiulation.

Ultrafiltration is described in detail in: Microfiltration and Ultrafiltration: Principles and Applications, L. Zeman and A. Zydney (Marcel Dekker, Inc., New York, N.Y., 1996); and in: Ultrafiltration Handbook, Munir Cheryan (Technomic Publishing, 1986; ISBN No. 87762-456-9). One filtration process is Tangential Flow Filtration as described in the Millipore catalogue entitled "Pharmaceutical Process Filtration Catalogue" pp. 177-202 (Bedford, Mass., 1995/96).

Ultrafiltration is generally considered to mean filtration using filters with a pore size of smaller than 0.1 km. By employing filters having such small pore size, the volume of the sample can be reduced through permeation of the sample buffer through the filter membrane pores while proteins, such as antibodies, are retained above the membrane surface.

Diafiltration is a method of using membrane filters to remove and exchange salts, sugars, and non-aqueous solvents, to separate free from bound species, to remove low molecular-weight species, and/or to cause the rapid change of ionic and/or pH environments. Microsolutes are removed most efficiently by adding solvent to the solution being diafiltered at a rate approximately equal to the permeate flow rate. This washes away microspecies from the solution at a constant volume, effectively purifying the retained protein of interest. In certain embodiments of the present invention, a diafiltration step is employed to exchange the various buffers used in connection with the instant invention, optionally prior to further chromatography or other purification steps, as well as to remove impurities from the protein preparations.

One of ordinary skill in the art can select appropriate membrane filter device for the UF/DF operation. Examples of membrane cassettes suitable for the present invention include, but not limited to, Pellicon 2 or Pellicon 3 cassettes with 10 kD, 30 kD or 50 kD membranes from EMD Millipore, Kvick 10 kD, 30 kD or 50 kD membrane cassettes from GE Healthcare, and Centramate or Centrasette 10 kD, 30 kD or 50 kD cassettes from Pall Corporation.

Upon completion of the diafiltration step, the protein concentration of the solution can be adjusted to with the diafiltration buffer to a final concentration of between about 5% and about 20% (w/v), or between about 10% and about 20% (w/v), or between about 15% and about 20% (w/v), or between about 18% and about 20% (w/v), or to a final concentration of about 5%, or 6%, 7%, 8%, 9%, 10%, 11%, 12%, 13%, 14%, 15%, 16%, 17%, 18%, 19%, or 20% for formulation.

In some embodiments, the formulated solution can be further sterilized by first filtering through a membrane filter with an absolute pore size of 0.2 micron or less with or without pre-filter. Then the solution is aseptically dispensed into final containers for proper sealing, with samples taken for testing.

Exemplary Purification Strategies

In certain embodiments, primary recovery can proceed by sequentially employing pH reduction, centrifugation, and filtration steps to remove cells and cell debris (including HCPs) from the production bioreactor harvest. In certain embodiments, the present invention is directed to subjecting a sample mixture from said sample to one or more affinity (e.g., protein A), AEX, and/or CEX purification steps. Certain embodiments of the present invention may include further purification steps, which can be performed prior to, during, or following the affinity and/or ion exchange chromatography steps. Examples of additional purification procedures include ethanol precipitation, isoelectric focusing, reverse phase HPLC, chromatography on silica, chromatography on heparin Sepharose™, further anion exchange chromatography and/or further cation exchange chromatography, chromatofocusing, SDS-PAGE, ammonium sulfate precipitation, hydroxylapatite chromatography, gel electrophoresis, and dialysis.

In certain embodiments the unbound Flow Through and wash fractions can be further fractionated and a combination of fractions providing a target product purity can be pooled.

In certain embodiments the protein concentration can be adjusted to achieve a differential partitioning behavior between the antibody product and the variants and/or impurities, e.g., the product-related substances and/or the process-related impurities, such that the purity and/or yield can be further improved. In certain embodiments the loading can be performed at different protein concentrations during the loading operation to improve the product quality/yield of any particular purification step. In certain embodiments the column temperature can be independently varied to improve the separation efficiency and/or yield of any particular purification step.

In certain embodiments, the loading, washing and/or elution buffer matrices can be different or composed of mixtures of chemicals, while achieving similar "resin inter-action" behavior such that the above novel separation can be effected. For example, but not by way of limitation, the loading and washing buffers can be different, in terms of ionic strength or pH, while remaining substantially similar in function in terms of the washout of the product achieved during the wash step.

In certain embodiments, the loading, washing and/or eluting steps can be controlled by in-line, at-line or off-line measurement of the variants and/or impurities levels, e.g., the product related substance levels and/or the process-related impurity levels, either in the column effluent, or the collected pool or both, so as to achieve the target product quality and/or yield. In certain embodiments, the loading concentration can be dynamically controlled by in-line or batch or continuous dilutions with buffers or other solutions to achieve the partitioning necessary to improve the separation efficiency and/or yield.

E. Methods of Assaying Sample Purity

Assaying Charged Variants

The levels of charged variants, e.g., acidic or basic species, in the samples produced using the techniques described herein may be analyzed by any charged based separation techniques known in the art. For example, charged variants, e.g., acidic species, or basic species, can be detected by charged based separation techniques such as isoelectric focusing (IEF) gel electrophoresis, capillary iso-electric focusing (cIEF) gel electrophoresis, cation exchange chromatography (CEX) and anion exchange chromatography (AEX).

Acidic species are variants with lower apparent pI and basic species are variants with higher apparent pI when antibodies are analyzed using IEF based methods. When analyzed by chromatography-based methods, acidic species and basic species are defined based on their retention times relative to the main peak. Acidic species are the variants that elute earlier than the main peak from CEX or later then than the main peak from AEX, basic species are the variants that elute later than the main peak from CEX or earlier than the main peak from AEX.

In certain embodiments, the charged variants are assayed by an ion exchange chromatography step. In some embodiments, quantitation is based on the relative area percent of detected peaks.

Assaying Size Variants/Isoforms

In certain embodiments, the levels of aggregates, monomer, fragments, half antibody and antibody isoforms in the samples produced using the techniques described herein are analyzed. In certain embodiments, the aggregates, monomer, and fragments are measured using a size exclusion chromatographic (SEC) method for each molecule. In certain embodiments, quantification is based on the relative area of detected peaks. In some embodiments, the level of half antibody is measured using non-reduced capillary electrophoresis sodium dodecyl sulfate (CE-SDS). Any additional technique, such as mass spectroscopy, can also be used for assaying size variants. In some embodiments, the levels of antibody isoforms are measured using reverse phase chromatography.

The present invention is further illustrated by the following examples which should not be construed as limiting in any way.

EXAMPLES

Example 1: Downstream Process for Antibody Purification

This Example describes the downstream process parameters, operational targets and ranges, and in-process controls developed for 200 L scale KPL-387 downstream manufacturing process (FIG. 1).

KPL-387 is a fully humanized immunoglobulin G2 (IgG2) monoclonal antibody that binds human interleukin-1 receptor 1 (IL1R1), inhibiting the activity of interleukin-la (IL-1α) and interleukin-1β (IL-1β). The antibody is comprised of two light chains (233 residues) and two heavy chains (463 residues).

Step 1: MabSelect PrismA Protein A Capture Chromatography Process

Figure 2:
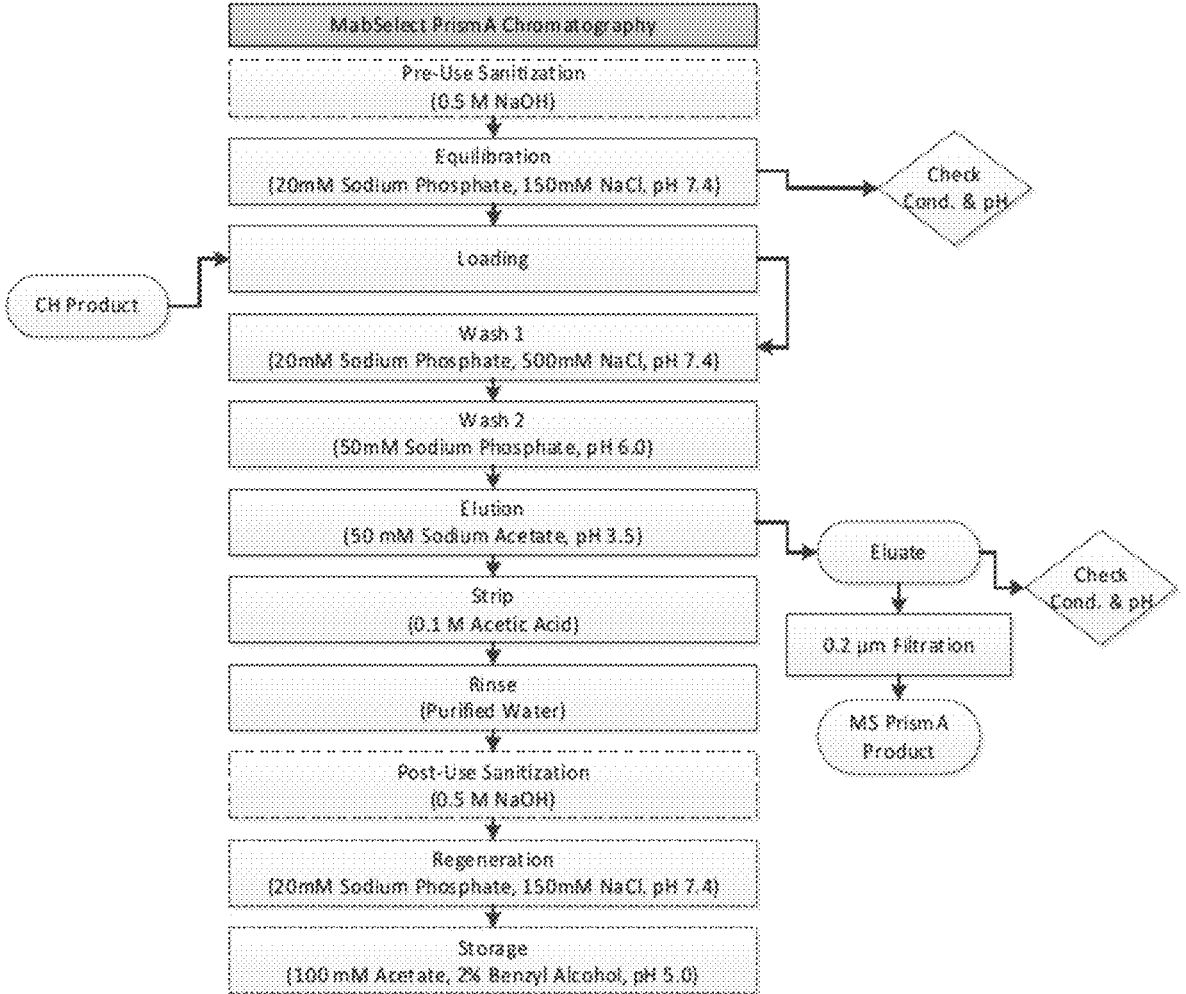
FIG. 2 is a flow diagram depicting the process for the Protein A affinity chromatography step.

The clarified harvest (CH) is held at 2-8° C. and loaded onto a Cytiva MabSelect PrismA Protein A capture chromatography column. This stage results in reduction in process volume and reduction of process-related impurities, such as host cell proteins (HCP) and aggregates. The Pro A step is outlined in FIG. 2. The expected yield across this stage is approximately 95%. The MabSelect PrismA product pool is processed through low pH viral inactivation as described in Step 2.

TABLE 1

Step 1 Operating Parameters - Capture Chromatography

| Process Step | Parameter | Unit | Target | Range |
|---|---|---|---|---|
| All steps | Flow Direction | N/A | Down flow | |
| Pre-Use | Volume | CV | 3 | ≥3 |
| Sanitization (0.5M NaOH) | Linear Flow Rate | cm/hr | 300 for 1 CV, then 152 | ≤330 |
| | Contact Time | Minutes | 15 | 15-30 |
| Equilibration (20 mM Sodium Phosphate, 150 mM NaCl, pH 7.4) | Volume | CV | 4 | ≥3.8 |
| | Linear Flow Rate | cm/hr | 300 | 270-330 |
| | pH | pH | 7.4 | 7.2-7.6 |
| | Conductivity | mS/cm | | |
| Load | Loading Mass Ratio | g/L Resin | 55 | TBD ≤55 |
| | Load Temperature | ° C. | 2-25° C. | |
| | Linear Flow Rate | cm/hr | 200 | 180-220 |
| Wash 1 (20 mM Sodium Phosphate, 500 mM NaCl, pH 7.4) | Volume | CV | 5 | ≥4.8 |
| | Linear Flow Rate | cm/hr | 300 | 270-330 |
| Wash 2 (50 mM Sodium Phosphate, pH 6.0) | Volume | CV | 5 | ≥4.8 |
| | Linear Flow Rate | cm/hr | 300 | 270-330 |

TABLE 1-continued

Step 1 Operating Parameters - Capture Chromatography

| Process Step | Parameter | Unit | Target | Range |
|---|---|---|---|---|
| Elution (50 mM Sodium Acetate, pH 3.5) | Linear Flow Rate | cm/hr | 300 | 270-330 |
| | Start Collection at UV280 | AU/cm | 0.25 | N/A |
| | End Collection at UV280 | AU/cm | 0.25 | N/A |
| Post-Collection Eluate pH | Mixing Rate | RPM | TBD in MFG | |
| | Mixing Time | Minutes | TBD in MFG | |
| | Eluate pH | pH | 4.2 | |
| 0.2 μm Filter | Membrane Type | Description | | |
| | Load Capacity | L/m² | TBD in MFG | |
| Strip (0.1M Acetic Acid) | Volume | CV | 2 | ≥1.8 |
| | Linear Flow Rate | cm/hr | 300 | 270-330 |
| Purified Water Rinse | Volume | CV | 2 | ≥1.8 |
| | Linear Flow Rate | cm/hr | 300 | 270-330 |
| Post-Use Sanitization (0.5M NaOH) | Volume | CV | 3 | ≥3 |
| | Linear Flow Rate | cm/hr | 300 for 1 CV, then 152 | ≤330 |
| | Contact Time | Minutes | 15 | 15-30 |
| Regeneration (20 mM Sodium Phosphate, 150 mM NaCl, pH 7.4) | Volume | CV | 3 | ≥3.8 |
| | Linear Flow Rate | cm/hr | 300 | 270-330 |
| | pH | pH | 7.4 | 7.3-7.5 |
| | Conductivity | mS/cm | FIO | FIO |
| Storage (100-200 mM Acetate, 2% Benzyl Alcohol, pH 5.0) | Volume | CV | 3 | ≥2.8 |
| | Linear Flow Rate | cm/hr | 300 | ≤330 |
| Hold Storage | Cold Storage Condition | ° C. | 2-8 | |
| | | Hours | ≤168 | |
| | Ambient Storage Condition | ° C. | 15-25 | |
| | | Hours | ≤168 | |

Step 2: Low pH Viral Inactivation

Figure 3:
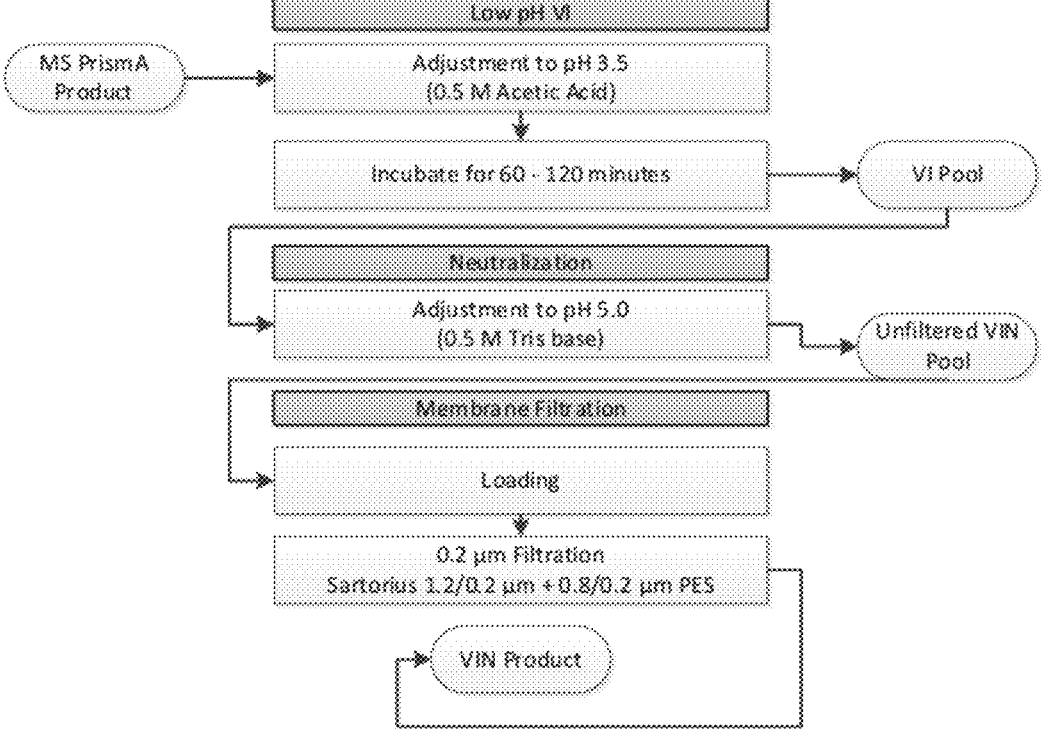
FIG. 3 is a flow diagram depicting the process for the viral inactivation step.

The affinity chromatography eluate from Step 1 is pooled and processed through viral inactivation by low pH hold. This step is designed to inactivate enveloped viruses. The pH of the staffing material is lowered through the addition of acetic acid. The pool is adequately mixed to ensure a homogeneous mixture has been achieved. Once mixing is completed and the product pool is within the pH range, the viral inactivation time begins. After the target inactivation time has passed the solution is adjusted to a higher pH using Tris base. The neutralized eluate is then filtered with a dual layer 0.8/0.2 μm PES filter into a bioprocess container for storage. The expected yield across this step is >95%. The low pH hold step is outlined in FIG. 3. The process parameters for the pH adjustment are shown in Table 2. The filtered VIN Product is processed through cation exchange chromatography as described in Step 3.

TABLE 2

Step 2 Process Parameters - Low pH Viral Inactivation

| Process Step | Parameter | Unit | Target | Range |
|---|---|---|---|---|
| Operating Parameters for All Adjustments | Operation Temperature | ° C. | 20 | ≥15 ≤25 |
| | Mixing Rate | RPM | TBD in MFG | |
| | Mixing Time | Minutes | TBD in MFG | |
| Low pH Titration and Incubation | Low pH Titrant Addition | MS PrismA Product weight % (w/w) | 23 | TBD |

TABLE 2-continued

| | Step 2 Process Parameters - Low pH Viral Inactivation | | | |
|---|---|---|---|---|
| Process Step | Parameter | Unit | Target | Range |
| | pH After Adjustment | pH | 3.5 | ≥3.4 ≤3.6 |
| | Mixing during low pH hold | ON/OFF | | OFF |
| | Incubation Time after pH Target Achieved | Minutes | 60 | ≥60 ≤120 |
| Neutralization | Neutralization Titration | VI Pool Fraction weight % (w/w) | 15 | TBD |
| | pH After Adjustment | pH | 5.0 | 4.9-5.1 |
| Filtration Operating Conditions | Filter Type | Description | | |
| | Membrane Loading Ratio | L/m² | | ≤150 |
| | Differential Pressure | bar (psid) | | ≤2.0 (≤29) |
| Hold Storage | Cold Storage Condition | ° C. | | 2-8 |
| | | Hours | | ≤TBD |
| | Ambient Storage Condition | ° C. | | 15-25 |
| | | Hours | | ≤TBD |

Step 3: POROS XS Cation Exchange Chromatography

Figure 4:
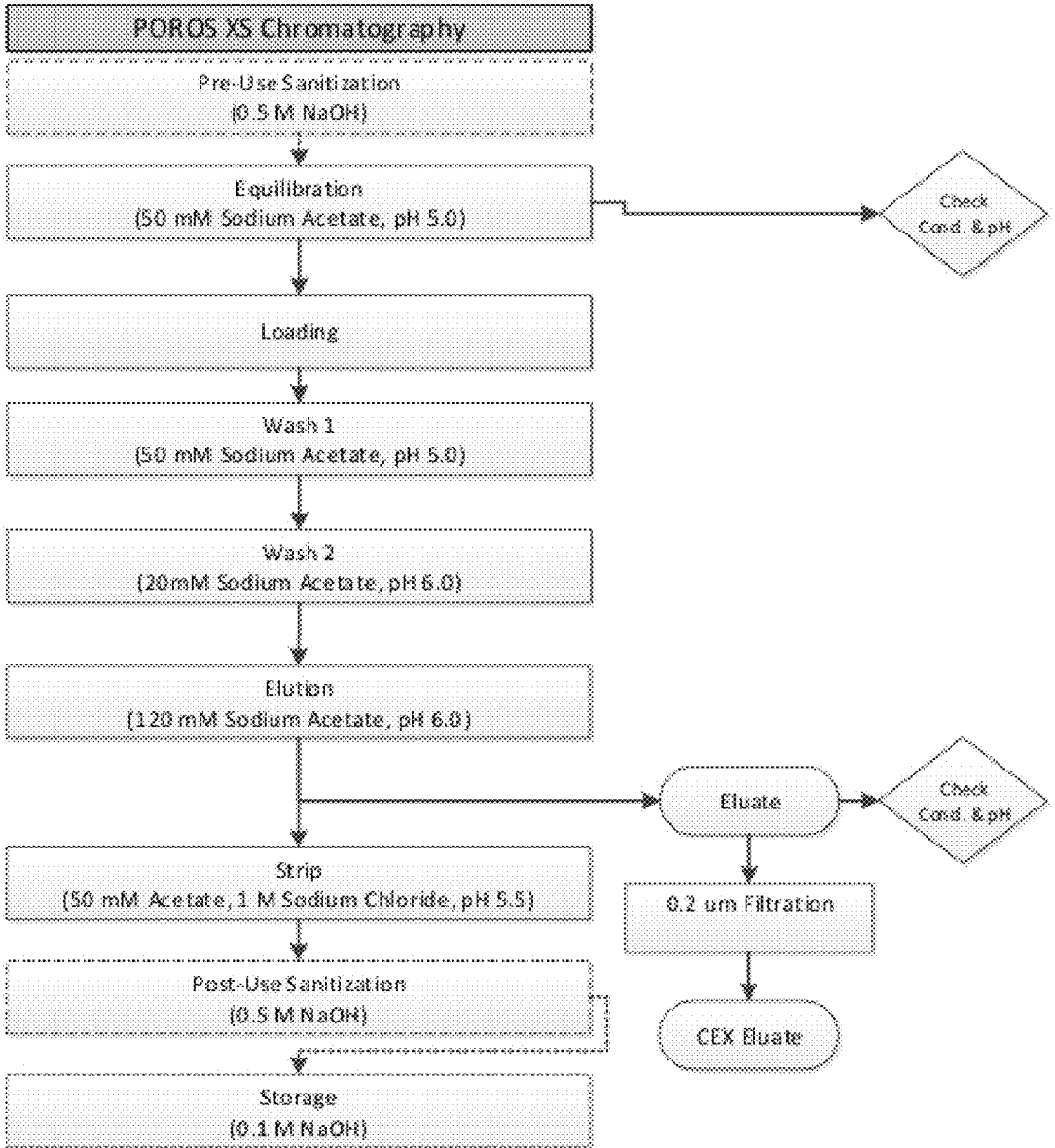
FIG. 4 is a flow diagram depicting the process for the cation exchange chromatography step.

The flow diagram is outlined in FIG. 4. Development results indicate, CX column reduces impurities, including high molecular weight (HMW) species, low molecular weight (LMW) species, and host cell protein (HCP). Bound antibody is eluted with higher pH and salt buffer. Expected yield across this stage is >90%. Multiple CEX cycles are performed with VI pool produced from a single reactor run. Each CEX eluate is filtered inline during elution through 0.2 μm filter and into a bioprocess container. CEX eluates are pooled prior to subsequent AEX purification.

TABLE 3

| | Step 3 Operating Parameters - Cation Exchange Chromatography | | | |
|---|---|---|---|---|
| Process Step | Parameter | Unit | Target | Range |
| All Steps | Flow Direction | N/A | Downflow | |
| Pre-Use Sanitization (0.5M NaOH) | Volume | CV | 3 | ≥3 |
| | Linear Flow Rate | cm/hr | 300 for 1CV, then 76 | ≤330 |
| | Contact Time | Minutes | 30 | 30-60 |
| Equilibration (50 mM Sodium Acetate, pH 5.0) | Volume | CV | 4 | ≥3.8 |
| | Linear Flow Rate | cm/hr | 300 | 270-330 |
| | pH | pH | 5.0 | 4.8-5.2 |
| Load | Conductivity | mS/cm | | |
| | Loading | g/L Resin | 80 | ≤80 |
| | Load Temperature | ° C. | 18 | 15-25 |
| | Linear Flow Rate | cm/hr | 300 | 270-330 |
| Chase (50 mM Sodium Acetate, pH 5.0) | Volume | CV | 3 | ≥2.8 |
| | Linear Flow Rate | cm/hr | 300 | 270-330 |
| Wash 2 (20 mM Sodium Acetate, pH 6.0) | Volume | CV | 5 | ≥4.8 |
| | Linear Flow Rate | cm/hr | 300 | 270-330 |
| Elution (120 mM Sodium Acetate, pH 6.0) | Linear Flow Rate | cm/hr | 300 | 270-330 |
| | Start Collection | AU/cm | 1 | N/A |
| | End Collection at UV280 | AU/cm | 1 | N/A |
| | End Collection CV | CV | 3-5 | FIO |
| Post-Use Strip (50 mM Acetate, 1M Sodium Chloride, pH 5.5) | Volume | CV | 3 | ≥2.8 |
| | Linear Flow Rate | cm/hr | 300 | 270-330 |

TABLE 3-continued

| | Step 3 Operating Parameters - Cation Exchange Chromatography | | | |
|---|---|---|---|---|
| Process Step | Parameter | Unit | Target | Range |
| Post-Use Sanitization (0.5M NaOH) | Volume | CV | 3 | ≥3 |
| | Linear Flow Rate | cm/hr | 300 for 1CV, then 76 | ≤330 |
| | Contact Time | minutes | 30 | 30-60 |
| Storage (0.1M Sodium Hydroxide) | Volume | CV | 3 | ≥2.8 |
| | Linear Flow Rate | cm/hr | 300 | 270-330 |
| Filtration Operating Conditions | Membrane Type | Description | 0.45/0.2 μm PES | |
| | Load Capacity | L/m² | 268 | Non-critical |
| Hold Storage | Cold Storage Condition | ° C. | | 2-8 |
| | | Hours | | ≤TBD |
| | Ambient Storage Condition | ° C. | | 15-25 |
| | | Hours | | ≤TBD |

Step 4: Sartobind Q Membrane Anion Exchange Chromatography

Figure 5:
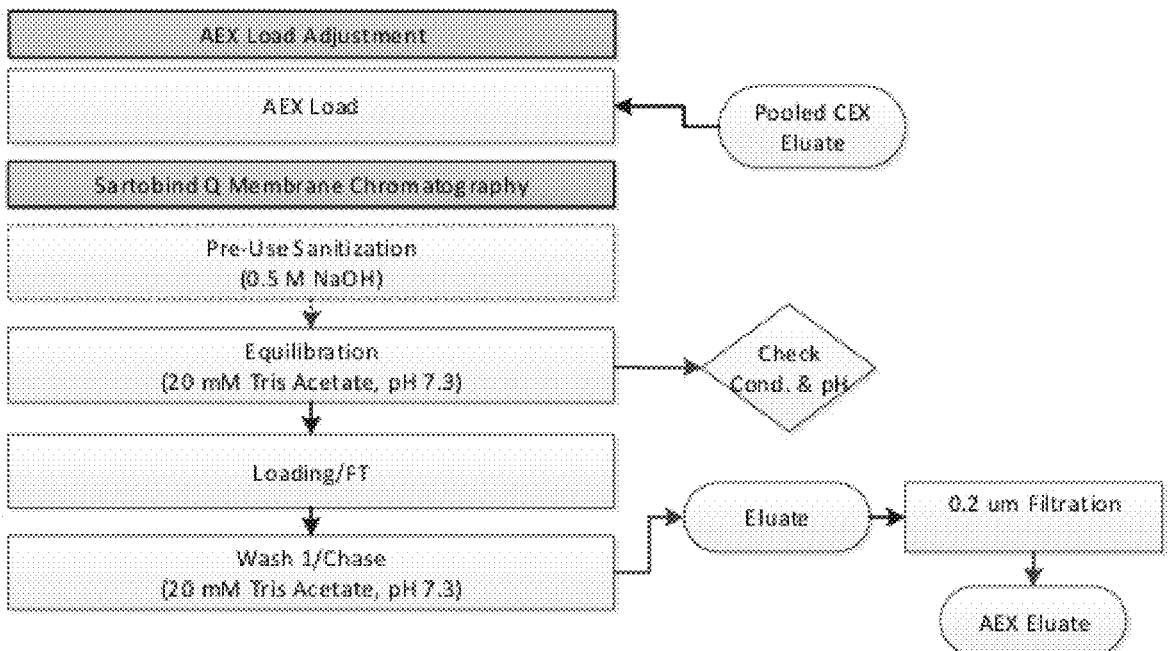
FIG. 5 is a flow diagram depicting the process for the anion exchange chromatography step.

This step is outlined in FIG. 5. The POROS XS Eluate Product from Step 3 is pH adjusted, and filtered in-line prior to loading onto the Sartobind Q AEX membrane. This step reduces impurities, including high molecular weight (HMW) species, low molecular weight (LMW) species, and host cell protein (HCP). The AEX flowthrough is processed through viral filtration as described in Step 5.

TABLE 4

| | Step 4 Operating Parameters- Sartobind Q Operations | | | |
|---|---|---|---|---|
| Process Step | Parameter | Unit | Target | Range |
| All Steps | Flow Direction | N/A | Downflow | |
| Sanitization (0.5M NaOH) | Volume | MV | 60 | ≥60 |
| | Linear Flow Rate | MV/min | 1 | ≤1 |
| | Contact Time | Minutes | 60 | ≥60 |
| Equilibration (20 mM Tris Acetate pH 7.3) | Volume | MV | 100 | ≥100 |
| | Linear Flow Rate | MV/min | 5 | <5 |
| | pH | pH | 7.3 | 7.1-7.5 |
| | Conductivity | mS/cm | | |
| Load | Loading | g/mL MV | 3.5 | ≤5 |
| | Load pH | pH | 7.3 | 7.2-7.4 |
| | Load Conductivity | mS/cm | FIO | FIO |
| | Load Temperature | ° C. | 18 | 15-25 |
| | Linear Flow Rate | MV/min | 5 | ≤5 |
| | Start Collection at UVA280 | AU/cm | 0.1 | N/A |
| Chase (20 mM Tris Acetate pH 7.3) | Linear Flow Rate | MV/min | 5 | ≤5 |
| | End Collection at UVA280 | AU/cm | 0.1 | N/A |
| 0.2 μm Filter | Membrane Type | Description | | |
| | Load Capacity | L/m² | | 280 |
| Hold Storage | Cold Storage Condition | ° C. | | 2-8 |
| | | Hours | | ≤TBD[1] |
| | Ambient Storage Condition | ° C. | | 15-25 |
| | | Hours | | ≤TBD |

Step 5: Viral Filtration with Millipore Viresolve Pro Filter

Figure 6:
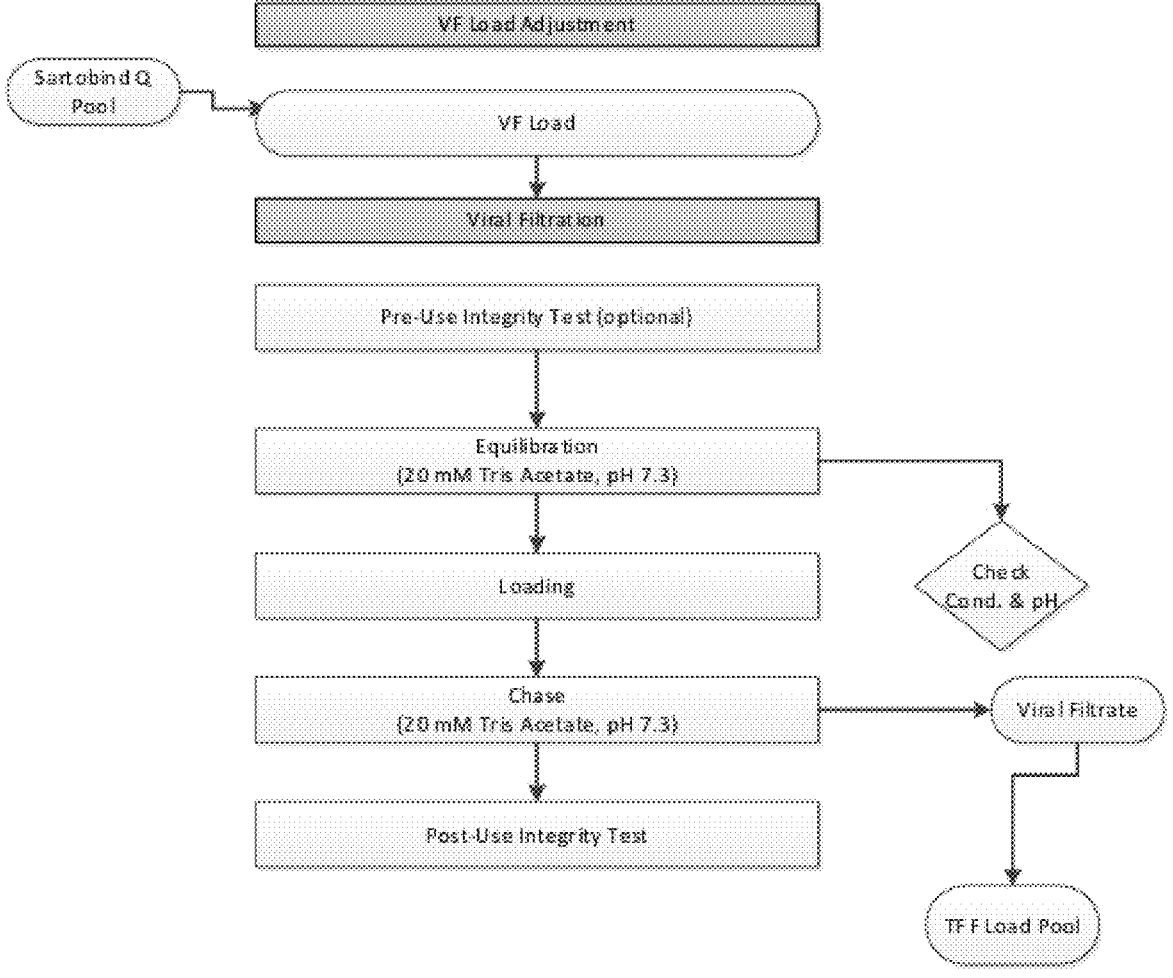
FIG. 6 is a flow diagram depicting the process for the viral filtration step.

The pooled flow-through from Sartobind Q chromatography in Step 4 is processed over the Viresolve Pro virus removal filter at constant pressure. The post-use viral filter integrity test should be conducted in accordance with site procedures and manufacturer recommendations. This step is outlined in FIG. 6. The expected yield across this step is >95%.

TABLE 5

| | Step 5 Operating Parameters - Viral Filtration | | | |
| --- | --- | --- | --- | --- |
| Process Step | Parameter | Unit | Target | Range |
| Pre-Filter | Membrane | Description | Viresolve Pro Shield H | |
| Viral Filter | Membrane | Description | Viresolve Pro Device | |
| Pre-Use | Viral Filter Inlet | bar (psid) | 2.0 (29.0) | 1.7-2.3 (24.6- |
| Sanitization | Pressure | | | 33.4) |
| (0.5M NaOH) | Volume | L/m² | 30 | ≥30 |
| | Contact Time | Minutes | 30 | ≥30 |
| Filter Flush | Viral Filter Inlet | bar (psid) | 2.0 (29.0) | 1.7-2.3 (24.6- |
| (Purified Water) | Pressure | | | 33.4) |
| | Volume | L/m² | 50 | ≥50 |
| Equilibration | Viral Filter Inlet | bar (psid) | 2.0 (29.0) | 1.7-2.3 (24.6- |
| (20 mM Tris | Pressure | | | 33.4) |
| Acetate, pH 7.3) | Volume | L/m² | 20 | ≥20 |
| | Effluent pH | pH | 7.3 | 7.1-7.5 |
| | Effluent Conductivity | mS/cm | | |
| Load | Viral Filter Differential Pressure | bar (psid) | 2.0 (29.0) | 1.7-2.3 (24.6- 33.4) |
| | Pre-Filter Load Capacity | L/m² | | ≤289 |
| | Viral Filter Load Capacity | L/m² | | ≤289 |
| Chase | Viral Filter Inlet | bar (psid) | 2.0 (29.0) | <2.3 (<33.4) |
| (50 mM Tris | Pressure | | | |
| Acetate, pH 7.3) | Volume | L/m² | 20 | ≤30 |
| Post-Use Integrity Test | Test Results | PASS/FAIL | PASS | |
| Hold Storage | Cold Storage Condition | °C. | 2-8 | |
| | | Hours | ≤TBD | |
| | Ambient Storage Condition | °C. | 15-25 | |
| | | Hours | ≤168 | |

Step 6: Ultrafiltration/Diafiltration, Formulation, and Filtration

Figure 7:
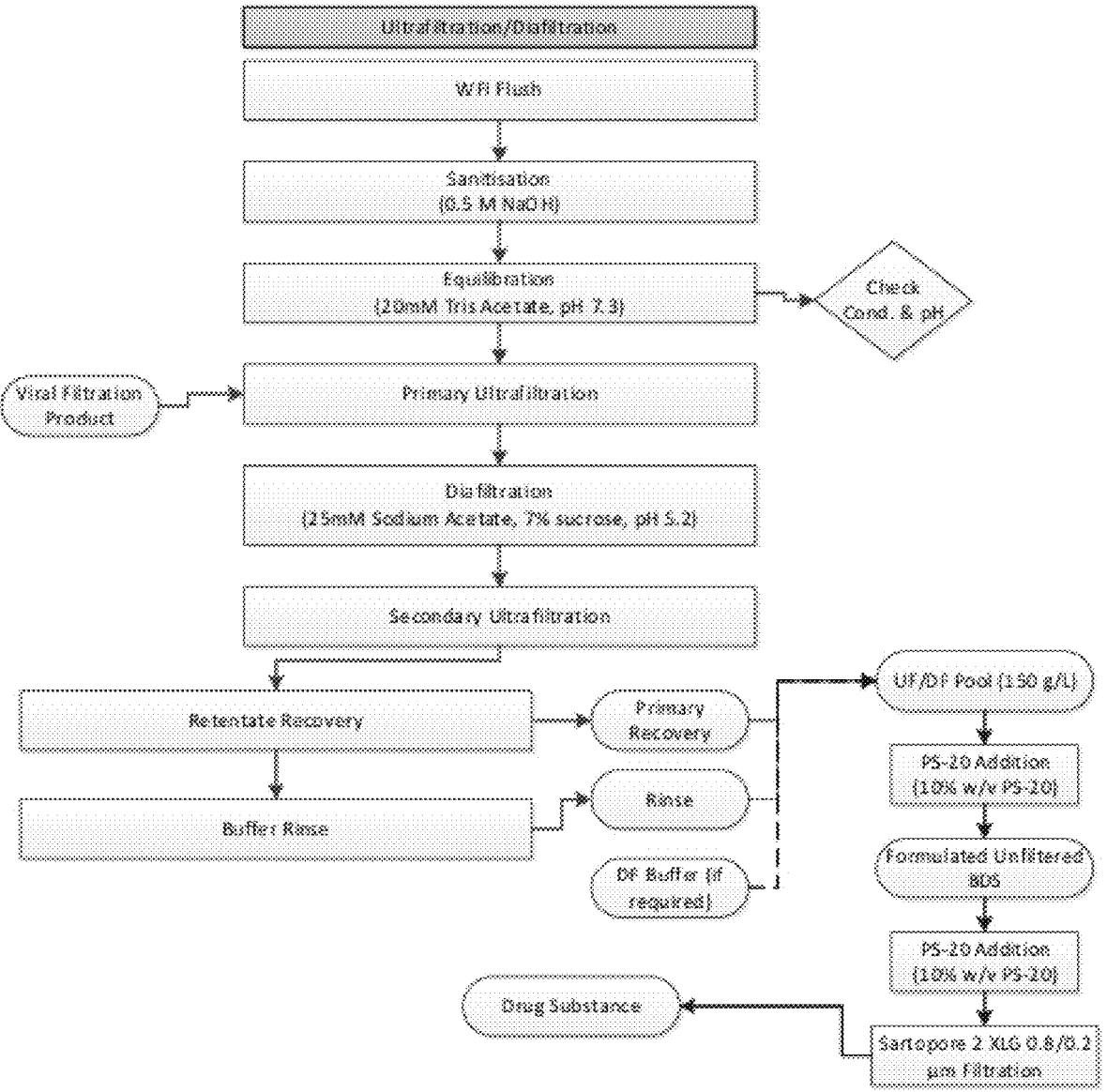
FIG. 7 is a flow diagram depicting the process for the ultrafiltration/diafiltration, formulation and filtration steps.

The Ultrafiltration/Diafltration (UF/DF) system is assembled according to vendor procedures and sanitized prior to each use. The viral filtrate is concentrated to a target concentration of 30 g ML using Repligen SIUS, 30 kDa ProStream cassettes. The retentate is diafiltered (DF) for 7 diavolumes (DV) with 25 mM Sodium Acetate, 7% Sucrose, pH 5.2. The diafiltered retentate is then over-concentrated to a target of 165 g/L. The UF/DF system is drained and rinsed with DF buffer. Pending protein concentration determination, the retentate and flush may be combined. The UF/DF pool is formulated with the addition of 10% w/v polysorbate 20 to achieve a final target concentration of 150 g/L in 25 mM Sodium Acetate, 7% sucrose, 0.02% P20, pH 5.2. The formulated UF/DF pool is filtered through a final 0.2 μm filter. The step is outlined in FIG. 7. The expected yield for this step (including cassette flush) is >90%.

TABLE 6

| | Step 6 Operating Parameters - Ultrafiltration/Diafiltration, Formulation, and Filtration | | | |
| --- | --- | --- | --- | --- |
| Process Step | Parameter | Unit | Target | Range |
| Operating | Membrane type | Description | SIUS ProStream 30 kDa | |
| Conditions | Temperature | °C. | 18 | 15-25 |
| | Membrane loading | g/m² | 400 | ≤500 |
| System Flush | Feed Flux | L/m²/hour | 300 | 200-400 |
| (Purified Water) | TMP | bar | 1 | 0.8-1.2 |
| | Volume through Permeate side | L/m² | ≥20 | |
| Sanitization | Feed Flux | L/m²/hour | 300 | 200-400 |
| (0.5M NaOH) | TMP | bar | 1 | 0.8-1.2 |
| | Sanitization time | minutes | 30 | ≥30 |
| System Flush | Feed Flux | L/m²/hour | 300 | 200-400 |
| (Purified Water) | TMP | bar | 1 | 0.8-1.2 |
| | Volume through Retentate side | L/m² | ≥20 | |
| | Volume through Permeate side | L/m² | ≥20 | |
| Equilibration | Feed Flux | L/m²/hour | 300 | 200-400 |
| (20 mM Tris | TMP | bar | 1 | 0.8-1.2 |
| Acetate, pH 7.3) | Volume through Retentate side | L/m² | ≥20 | |
| | Volume through Permeate side | L/m² | ≥20 | |

TABLE 6-continued

Step 6 Operating Parameters - Ultrafiltration/Diafiltration,
Formulation, and Filtration

| Process Step | Parameter | Unit | Target | Range |
|---|---|---|---|---|
| | Permeate pH | pH | 7.3 | 7.1-7.5 |
| | Permeate Conductivity | mS/cm | | |
| Primary Concentration | Feed Flux | L/m²/hour | 375 | 300-400 |
| | TMP | bar | 1 | 0.8-1.2 |
| | Concentration at end of the step | g/L | 30 | 25-35 |
| Diafiltration (25 mM Acetate, 7% sucrose, pH 5.2) | Diavolumes | DV | 7 | ≥7 |
| | TMP | bar | 1 | 0.8-1.2 |
| | Final Permeate pH | pH | 5.4 | 5.3-5.5 |
| | Final Permeate conductivity | mS/cm | | |
| Secondary Consideration | Feed Flux | L/m2/hour | 100 | 50-50 |
| | TMP | bar | 1 | 0.8-1.4 |
| | Depolarization Recirculation (Permeate Closed) | Minutes | 5 | 5-10 |
| | Concentration at end of the step (confirm by offline A280) | g/L | 165 | 165-175 |
| Low Flux Recirculation | Feed Flux | L/m²/hour | 100 | 50-150 |
| | Recirculation Time | Minutes | 5 | 5-10 |
| | Retentate Valve | OPEN/ CLOSED | FULLY OPEN | |
| | Permeate Valve | OPEN/ CLOSED | CLOSED | |
| Primary Recovery Rinse (25 mM Sodium Acetate, 7% Sucrose, pH 5.2) | Method | Description | Air displacement | |
| | Flush volume | L | 1.2x calculated system holdup volume | |
| | Recirculation Time | Minutes | 5 | 5-10 |
| Primary Recovery Pool | Mixing Rate | RPM | TBD in MFG | |
| | Mixing Time | Minutes | TBD in MFG | |
| UF/DF Pool (Primary Recovery + Rinse) | Target Concentration | g/L | 150 | 140-160 |
| | Mixing Rate | RPM | TBD in MFG | |
| | Mixing Time | Minutes | TBD in MFG | |
| Unfiltered BDS | Target Concentration | g/L | 150 | 140-160 |
| Dilution (25 mM Sodium Acetate, 7% Sucrose, pH 5.2) | Mixing Rate | RPM | TBD in MFG | |
| | Mixing Time | Minutes | TBD in MFG | |
| Polysorbate 20 Addition (10% w/v Polysorbate 20) | Polysorbate 20 Addition Ratio | kg/L | 0.002 | TBD |
| Final Filtration Operating Conditions | Membrane | Description | | |
| | Membrane Loading Ratio | L/m² | 54 | |
| | Differential Pressure | bar (psid) | <2.0 (<29.0) | |
| Final Filtration Load | Blowdown Method | Description | Air displacement | TBD |
| Final Filter Post-Use Integrity Test | Test Results | PASS/FAIL | PASS | |
| Hold Storage | Cold Storage | ° C. | 2-8 | |
| | Condition | Hours | ≤24 | |
| | Ambient Storage | ° C. | 15-25 | |
| | Condition | Hours | ≤24 | |

Representative performance data for each step are included in tables below.

TABLE 7.1

Protein A Performance Data

| Cycle | 1 | 2 |
|---|---|---|
| Column Height (cm) | 18.5 | |
| Column ID (cm) | 20 | |
| Resin | Mabselect PrismA | |
| Load Concentration (g/L) | 2.06 | |
| Resin Challenge (g/L resin) | 41 | 37 |
| Elution Volume (CV) | 3.0 | 5.4 |
| Elution Concentration (g/L) | 13.7 | 6.9 |
| Elution Total Protein (g) | 240 | 217 |
| Yield (%) | 100 | 99 |
| SEC (% Main/% HMW) | 99.4/0.6 | 95.9/4.1 |
| NR-CE-SDS (% Main/% Imp.) | 96.5/2.1 | 96.6/2.2 |
| R-CE-SDS (% Main/% Frag/% Other) | 92.4/6.2/1.3 | 92.3/6.2/1.5 |
| icIEF (% Main/% Acidic/% Basic) | 61.4/34.2/4.4 | 65.5/31.5/3.0 |
| HCP Eluate Pool (ppm) | 611 | |

TABLE 7.2

Viral Inactivation Performance Data

| | |
|---|---|
| Cycles Pooled: | 1.2 |
| Pool Concentration (g/L) | 9.2 |
| Pool Total Protein (g) | 445 |
| Initial pH | 4.0 |
| Viral Inactivation pH | 3.6 |
| Viral Inactivation Time (min) | 60 |
| Neutralized pH | 5.0 |
| Neutralized Conductivity (mS/cm) | 3.32 |
| 0.5M Acetic Acid Added (% w/w of Pool) | 12 |
| 0.5M Tris Base Added (% w/w of Pool) | 12 |
| Prefilter Area (m2) | 0.26 |
| Polishing Filter Area (m2) | 0.26 |
| Throughput achieved through a single filter at filter train fouling (L/m2) | 201 |
| Filtered VIN Pool Volume (L) | 60.2 |
| Filtered VIN Pool Concentration (mg/mL) | 7.3 |
| Yield % | 99 |

TABLE 7.3

CEX Performance

| Cycle | 1 |
|---|---|
| Column Height (cm) | 19.0 |
| Column ID (cm) | 20 |
| Resin | POROS XS |
| Load Concentration (g/L) | 7.3 |
| Resin Challenge (g/L resin) | 72 |
| Elution Volume (CV) | 4.5 |
| Elution Concentration (g/L) | 15.3 |
| Elution Total Protein (g) | 411 |
| Yield (%) | 96 |

| | Load |
|---|---|
| SEC (% Main/% HMW) | 99.2/0.8 |
| NR-CE-SDS (% Main/% Imp.) | 96.9/2.0 |
| R-CE-SDS (% Main/% Frag/% Other) | 92.5/6.5/1.0 |
| icIEF (% Main/% Acidic/% Basic) | 62.9/32.5/4.5 |
| HCP (ppm) | 174 |
| rProa (ppm) | 10.18 |
| rDNA (pg/mg) | 139 |

TABLE 7.4

AEX Performance

| Cycle | 1 |
|---|---|
| Membrane Volume (ml) | 150 |
| Membrane | Sartobind Q |
| Load Concentration (g/L) | 15.1 |
| Membrane Challenge (g/mL membrane) | 2.6 |
| Elution Volume (L) | 28.0 |
| Elution Concentration (g/L) | 13.8 |
| FT Total Protein (g) | 391 |
| Yield (%) | 99 |

| | Load |
|---|---|
| SEC (% Main/% HMW) | 98.7/1.3 |
| NR-CE-SDS (% Main/% Imp.) | 96.5/2.1 |
| R-CE-SDS (% Main/% Frag/% Other) | 93.5/5.5/1.3 |
| icIEF (% Main/% Acidic/% Basic) | 61.4/34.1/4.5 |
| HCP (ppm) | 13 |
| rProa (ppm) | 1.37 |
| rDNA (pg/mg) | 7 |

TABLE 7.5

VF Performance

| | |
|---|---|
| Membrane Area (m2) | 0.22 |
| Load Concentration (g/L) | 14.4 |
| Throughput (L/m2) | 148 |
| Load Challenge (g/m2) | 2135 |
| Filtrate Concentration (g/L) | 12.6 |
| Filtrate Total Protein | 443 |
| Yield (%) | 94 |

| | Load | Filtrate |
|---|---|---|
| SEC (% Main/% HMW) | 98.5/1.5 | 98.4/1.6 |
| NR-CE-SDS (% Main/% Imp.) | 96.6/2.0 | 95.5/2.1 |
| R-CE-SDS (% Main/% Frag/% Other) | 92.9/5.9/1.2 | 91.9/5.8/2.3 |
| icIEF (% Main/% Acidic/% Basic) | 61.7/34.2/4.1 | 62.1/34.0/3.9 |
| HCP (ppm) | 3 | 0 |
| rProa (ppm) | 1.41 | |
| rDNA (pg/mg) | <1 | <1 |

TABLE 7.6

UFDF and Final Filtration Performance

| | |
|---|---|
| Membrane Area (m$^2$) | 1 |
| Load Concentration (g/L) | 11.58 |
| Membrane Challenge (g/m$^2$) | 307 |
| Filtrate Concentration (g/L) | 100.35 |
| Filtrate Total Protein | 285 |
| Yield (%) | 94 |
| Final Filter Throughput (L/m$^2$) | 44 |

TABLE 8

| | | Drug Substance Performance | | | |
|---|---|---|---|---|---|
| Test | | KPL-387 Lot 1 | KPL-387 Lot 2 | KPL-387 Lot 3 | KPL-387 Lot 4 |
| Appearance | Color and state | ≤BY4, Slightly Brownish-Yellow Liquid | BY4, Slightly Brownish-Yellow Liquid | BY5, Slightly Brownish-Yellow Liquid | Slightly Brownish-Yellow Liquid |
| | Clarity | Slighly Opalescent | Clear | Slightly Opalescent | Clear |
| pH | | 5.3 | 5.3 | 5.3 | 5.3 |
| Total Protein Concentration (A280) | | 103 | 152 | 100.7 | 153.4 |
| Imaging Capillary Isoelectric Focusing (iCIEF) | Main PI | 7.6 | 7.6 | 7.6 | 7.6 |
| | Main Peak | 61.2% | 60.7% | 61.7% | 62.8% |
| | Acidic Species | 34.9% | 35.5% | 35.8% | 35.3% |
| | Basic Species | 4.0% | 3.8% | 2.5% | 1.9% |
| Capillary Electrophoresis Sodium Dodecyl Sulfate-Non-reducing (CE-SDS-NR) | Main Peak | 97.6% | 97.5% | 97.7% | 98.4% |
| | Total Fragments | 0.9% | 1.0% | 1.4% | 0.8% |
| | Total Aggregate | NT | NT | 0.8% | 0.8% |
| Capillary Electrophoresis Sodium Dodecyl Sulfate-Reduced (CE-SDS-R) | Heavy Chain + Light Chain peaks | 92.7% | 92.3% | 95.9% | 96.5% |
| | peak 1 | NT | NT | 2.4% | 2.0% |
| | Total impurities | 7.3% | 7.7% | 1.8% | 1.5% |
| Size Exclusion Chromatography (HPLC) | Monomer | 98.4% | 97.9% | 98.7% | 98.5% |
| | High molecular weight species | 1.6% | 2.1% | 1.3% | 1.5% |
| | Low molecular weight species | 0.0% | ND | ND | ND |
| Host Cell Protein (ELISA) | | 0.03 | NT | 1 | 1 |
| Host Cell DNA (qPCR) | | <0.1 | NT | <0.1 | <0.08 |
| Residual Protein A (ELISA) | | 0.37 | NT | <0.276 | <0.276 |
| Endotoxin (LAL) | | NT | NT | ≤0.005 | ≤0.003 |
| Bioburden (TAMC and TYMC) | | 0 CFU/ 10 mL TAMC | NT | 0 CFU/ 10 mL TAMC | 0 CFU/ 10 mL TAMC |
| | | 0 CFU/ 10 mL TYMC | NT | 0 CFU/ 10 mL TYMC | 0 CFU/ 10 mL TYMC |
| OSMO | | 290 | 310 | NT | NT |

Example 2: CEX Robustness Study

Studies were undertaken to investigate the robustness of the purification process designed for KPL-387. To evaluate the effect of pH of the CEX elution conditions on product quality, a robustness study was performed that included three experimental cycles to evaluate the performance of two alternative purification scenarios: low yield/high quality (−Y/+Q) and high yield/low quality (+Y/−Q) as compared to control runs that were performed at target operating conditions for KPL-387 purification. Buffers used for each cycle of the CEX robustness study are shown in Table 9. The process parameters for the CLX elution studies are shown in Table 10. Performance data for the CLX robustness study is shown in Table 11.

TABLE 9

| | Buffers | |
|---|---|---|
| Robustness Study | Description | Purpose |
| Control | 50 mM sodium acetate pH 5.0 | CEX Equil/Wash 1 |
| | 20 mM sodium acetate pH 6.0 | CEX Wash 2 |
| | 120 mM sodium acetate pH 6.0 | CEX Elution |
| high yield/ low quality (+Y/−Q) | 30 mM sodium acetate pH 4.8 | CEX Robusness Wash 1 (+Y/−Q) |
| | 10 mM sodium acetate pH 5.8 | CEX Wash 2 (+Y/−Q) |
| | 130 mM sodium acetate pH 6.2 | CEX Elution (+Y/−Q) |

TABLE 9-continued

| Buffers | | |
|---|---|---|
| Robustness Study | Description | Purpose |
| low yield/ high quality (−Y/+Q) | 70 mM sodium acetate pH 5.2 | CEX Robustness Wash 1 (−Y/+Q) |
| | 40 mM sodium acetate pH 6.2 | CEX Wash 2 (−Y/+Q) |
| | 110 mM sodium acetate pH 5.8 | CEX Elution (−Y/+Q) |

TABLE 10

CEX Performance

| Run | Challenge (g/L) | Yield (%) | Elution Pool pH | Elution Pool Conductivity (mS/cm) |
|---|---|---|---|---|
| Control | 80 | 87 | 5.9 | 7.6 |
| −Y/+Q | 80 | 67 | 5.8 | 6.9 |
| +Y/−Q | 80 | 84 | 5.7 | 7.7 |

TABLE 11

CEX Analytical Results

| Run | SEC (% Main/% HMW) | HCP (ppm) | rProA (ppm) |
|---|---|---|---|
| Load | 99.5/0.5 | 373 | 3.2 |
| Control | 97.6/2.4 | 17 | 0.8 |
| −Y/+Q | 99.1/0.9 | 29 | 0.3 |
| +Y/−Q | 95.9/4.1 | 100 | 1.6 |

Notably, these results unexpectedly demonstrate that elution of KPL-387 from the CLX column with an elution buffer at a pH of 6.2 or above and/or a sodium acetate at 130 mM or above resulted in an increase in HMW species, HCP and contaminating ProA, which are all highly undesirable impurities.

Example 3: IL-1R1 Antibody Stability Study

This Example describes the effect of acidic species on KPL-387 stability (FIG. 8). Purified KPL-387 drug substance was sourced from three different lots, each with varying levels of acidic species at baseline (level of acidic species in Lot 1<Lot 2<Lot 3). All samples of KPL-387 drug substance were formulated in the same liquid formulation and the stability of KPL-387 was tested by storing them at 5, 25 or 40° C. for 1 to 6 months at 100 mg/ml or 150 mg/ml (as indicated in FIG. 8), and assessed for the ΔHMW % by SEC. FIG. 8 shows the ΔHMW % in each sample over time. Notably, the results surprisingly demonstrate a positive correlation between the baseline level of acidic species in a sample and an increase in the amount of higher molecular weight aggregates of KPL-387 that form over time. These data demonstrate the importance of maintaining an acceptable level, or preventing an increase, of acidic species throughout the downstream purification process KPL-387. Indeed, acidic species present in the purified KPL-387 can be detrimental to product stability by promoting an increase in high molecular weight aggregates during longterm storage.

Example 4: Effects of Acidic Species on Antibody Potency

This Example describes the effect of acidic species on KPL-387 binding potency. Charge variants from an anti IL1-R1 antibody drug substance sample were enriched and analyzed to assess their impact on potency using an ELISA based analytical method. During development it was determined that a combination of displacement chromatography and bind and elute chromatography could be effective at separating and enriching charge variants (acid, main, and basic) to enable analysis by ELISA. A representative sample was loaded onto a Capto S ImpRes cation exchange column. Prior to loading, the material was titrated to pH 5.0 using acetic acid.

During loading, an absorbency increase was observed, and displaced product was collected and labeled as fraction 1. The column was washed with 50 mM sodium acetate, pH 5.0 and product began to elute. This was collected and labeled as fraction 2. A second wash was applied to the column and absorbency returned to baseline. Elution buffer, 120 mM sodium acetate pH 6.0, was then applied to the column and a sharp peak was observed and collected as fraction 3. The levels of the acidic species of KPL-387 varied between fractionated pools 1, 2 and 3, as shown below in Table 12 and FIG. 9.

The Capto SP ImpRes fractions were submitted for analysis using icIEF (Imaged Capillary Isoelectric Focusing) and potency by ELISA. Relative potency was assessed in a binding ELISA assay in which the binding of KPL-387 to human IL1R1 was quantified and compared to a reference standard. Potency was assessed relative to the binding curve generated in the same assay for the reference standard. The reportable value is a relative potency calculated as a percentage of the Reference Standard's EC50 relative to the EC50 of the sample.

As shown in Table 12 and FIG. 9, it is evident that samples with enriched acidic species exhibited lower potency as compared to the reference standard.

TABLE 12

Effect of Charge Variant on Antibody Binding Potency by ELISA

| Sample Name | % relative potency by ELISA | Total Peak Area % | | |
|---|---|---|---|---|
| | | % Acidic | % Main | % Basic |
| KPL-387 Reference Standard | 100 | 35.5 | 61.1 | 3.3 |
| Fractionated Pool 1 | 68 | 56.8 | 42.0 | 1.1 |
| Fractionated Pool 2 | 93 | 42.7 | 56.0 | 1.4 |
| Fractionated Pool 3 | 102 | 30.8 | 65.3 | 3.9 |

Example 5: Upstream Manufacturing Process

This Example evaluates the effects of various parameters of the upstream manufacturing process on maintaining a consistent charge profile with a goal of controlling charge heterogeneity and balancing expression levels.

To determine and verify the optimal bioreactor process condition, specifically harvest day and cell viability at harvest, a representative bioreactor was operated for a 24-day production run. Key operating parameters, including seeding density, metabolite feed strategy, gassing strategy, pH control, and agitation, were maintained consistently within historical ranges to ensure comparability and consistency.

Figure 10:
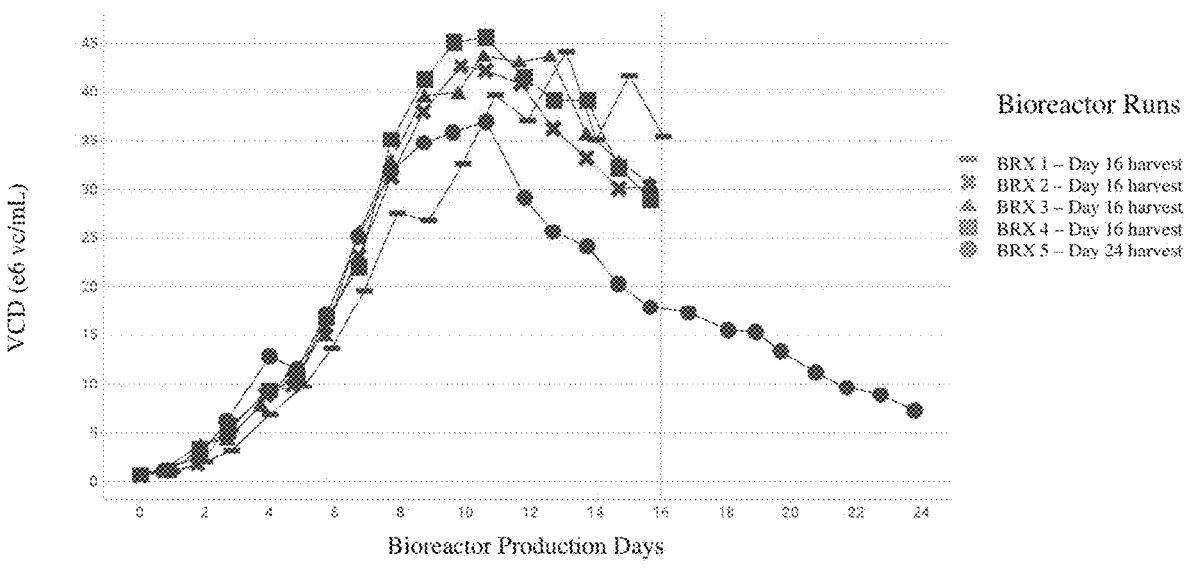
FIG. 10 is a graph depicting the correlation between the bioreactor production days and the viable cell density (VCD) at harvest.
Figure 11:
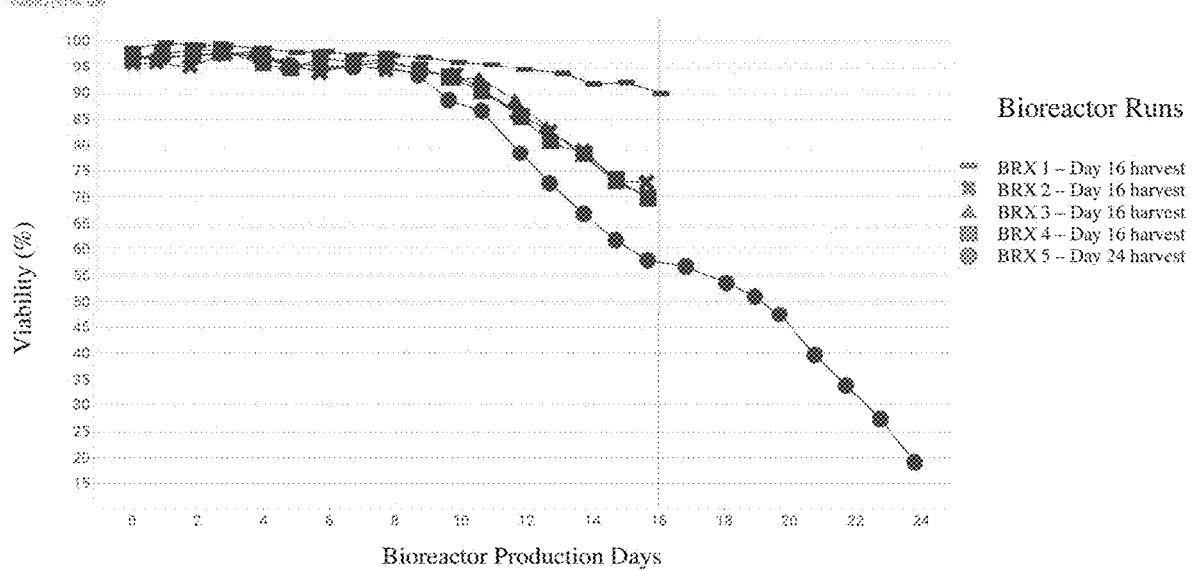
FIG. 11 is a graph depicting the correlation between the bioreactor production days and the cell viability.

It was observed that viability and viable cell density began to decline, and continued to rapidly decline, post day 12. On day 24, viable cell density reached $7.5 \times 10^6$ cells/mL, which is approximately ⅕ of peak viable cell density, and viability reached <20% suggesting significant cell death and apoptosis. Viable cell density and viability trends compared to historical batches can be found in FIG. 10 and FIG. 11, respectively.

Figure 12:
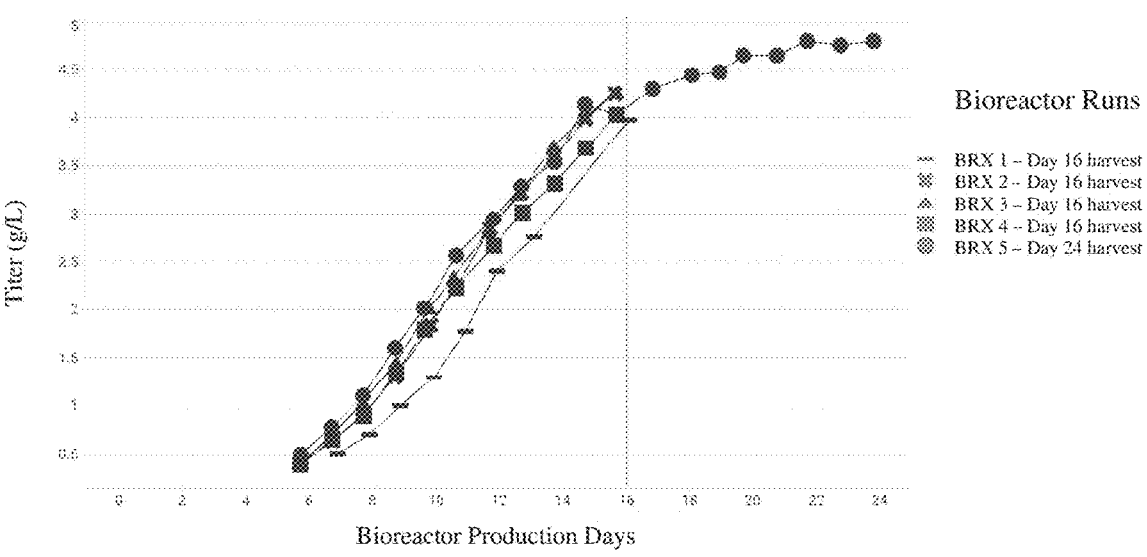
FIG. 12 is a graph depicting the correlation between the bioreactor production days and the cumulative antibody expression levels.

Samples were analyzed for expression (titer) starting on day 5 to determine the impact of increased production days on cumulative expression levels. FIG. 12 shows that expression is linear through day 16 and the slope declines from day 17 through day 24.

Figure 13:
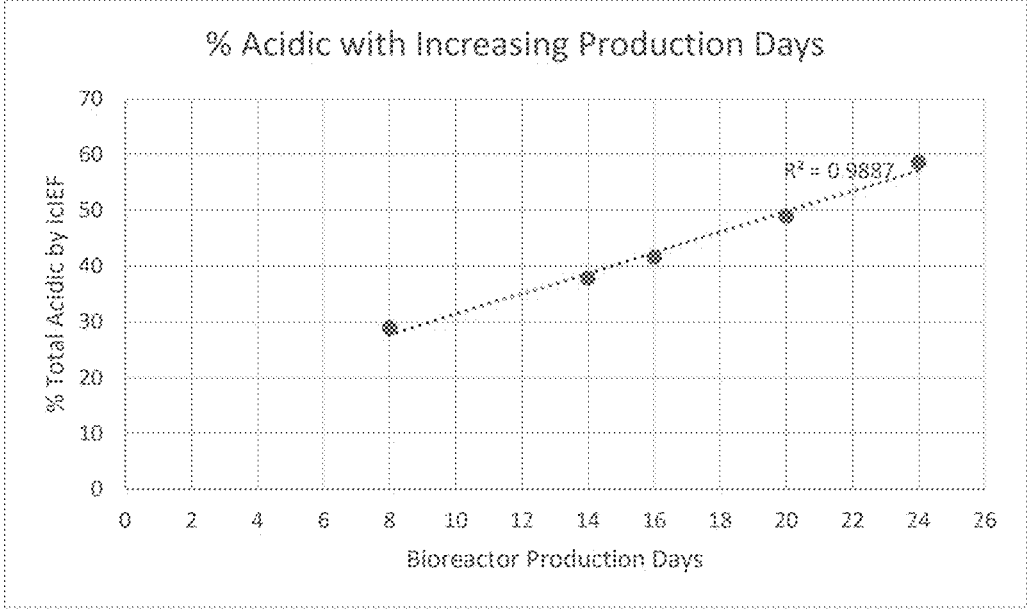
FIG. 13 is a graph depicting the correlation between the bioreactor production days and the acidic species levels.

Samples at various production days were tested using icIEF to determine levels of charge variants as shown in FIG. 13 and Table 13. Charge variants were separated and quantified by imaging capillary isoelectric focusing. Samples were injected onto a capillary cartridge, focused, and detected by Fluorescence. The main isoform pI and the percent peak area of lower pI isoforms (acidic species), main isoform, and higher pI isoforms (basic species) were reported relative to the total isoforms peak area.

These data demonstrated that acidic variants increased at a rapid linear rate with increasing production days. Culture viability was also examined as part of the increasing duration. As viability decreases with increasing production days, acidic variant levels continued to increase, suggesting viability controls are also a means to ensure that appropriate charge variants are controlled to maintain an appropriate product quality while balancing product yield. Additionally, upon harvest clarification and ambient hold for an additional 4 days (cell free), the harvest pool continued to exhibit increased acidic variants, but at a slower rate compared to production.

TABLE 13

Effect of Culture Duration on Levels of Charge Variants by icIEF

| Culture Production Days | pI | % Total Acidic | % Main | % Total Basic |
|---|---|---|---|---|
| KPL-387 Reference Standard | 7.6 | 34.8 | 61.7 | 3.5 |
| 8 days | 7.6 | 28.9 | 66.6 | 4.5 |
| 14 days | 7.6 | 37.8 | 58.9 | 3.3 |
| 16 days | 7.6 | 41.6 | 55.8 | 2.6 |
| 20 days | 7.6 | 49.0 | 48.9 | 2.1 |
| 24 days | 7.6 | 58.6 | 39.3 | 2.2 |
| 24 days with 4 day ambient clarified harvest hold | 7.6 | 61.7 | 36.6 | 1.7 |

In addition to assessing production day duration and viability on charge variants, levels of KPL-387 isoforms (IgG2 isoforms A, A/B and B) were monitored throughout the course of the study. Isoform profile was assessed using reverse phase chromatography performed using Ultra Performance Liquid Chromatography (UPLC) and reverse phase column to separate isoforms based on their hydrophobicity. The reported value was a percent area of an isoform compared to total area for all peaks.

Figure 14:
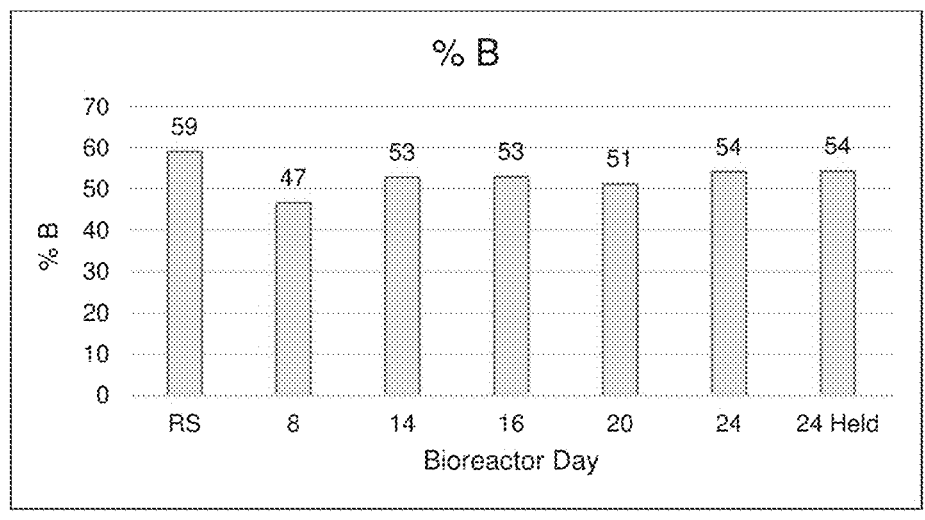
FIG. 14 is a graph depicting the levels of antibody isoforms (A, B and A/B) under different bioreactor production days.
Figure 14:
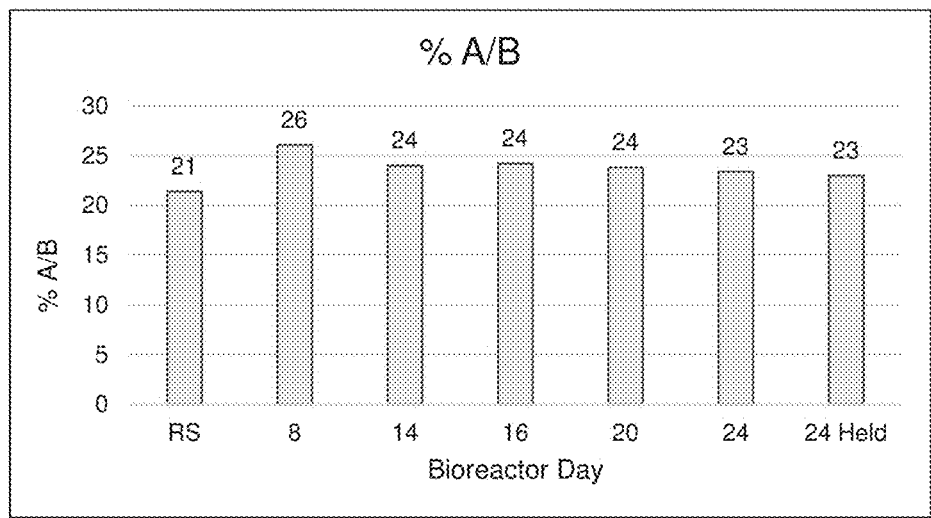
Figure 14:
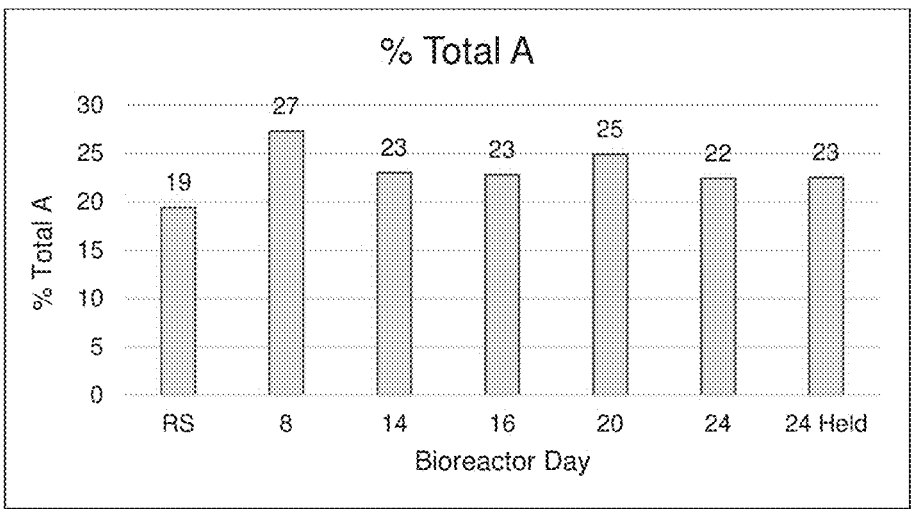

FIG. 14 show that the relative levels of isoforms A, A/B and B were maintained throughout the duration of the production reactor and were not impacted during harvest hold. Table 14 shows samples from several production runs harvested on day 16, demonstrating that isoform B is the predominant isoform with isoform A/B being the second and isoform A being the third.

TABLE 14

Isoform Levels in KPL-387 Drug Substance Harvested on Day 16

| Sample | | Results | | |
|---|---|---|---|---|
| ID# | Sample Name | % Total B | % Total A/B | % Total A |
| RS | KPL-387 Reference standard | 58.7 | 21.7 | 19.6 |
| 1 | KPL-387 DS | 70.1 | 15.5 | 14.4 |
| 2 | KPL-387 DS | 55.5 | 23.3 | 21.1 |
| 3 | KPL-387 DS | 70.4 | 15.7 | 13.9 |
| 4 | KPL-387 DS | 65.3 | 19.4 | 15.4 |
| 5 | KPL-387 DS | 53.0 | 24.2 | 22.8 |

Figure 15:
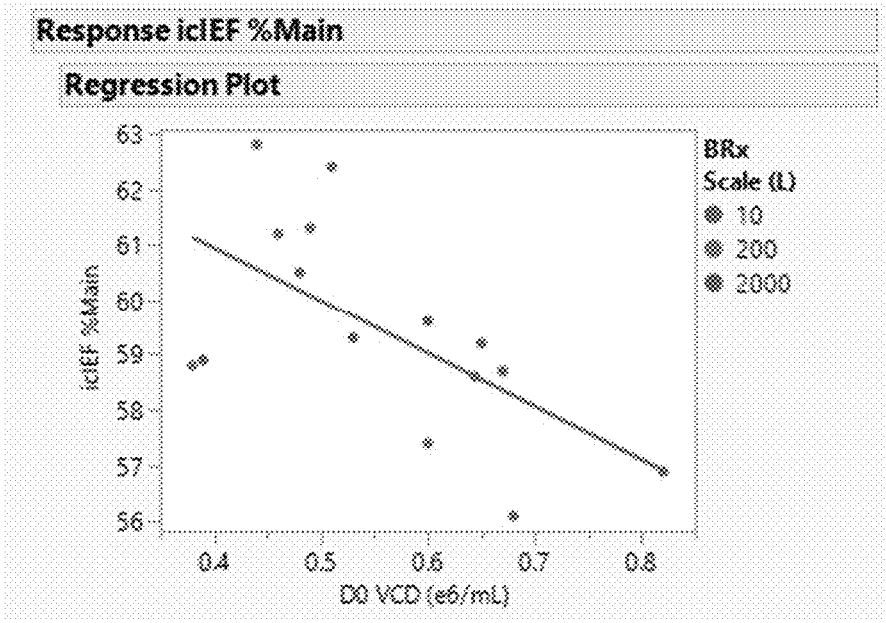
FIG. 15 is a graph depicting the correlation between seeding density and the main (top) or acidic (bottom) species levels.
Figure 15:
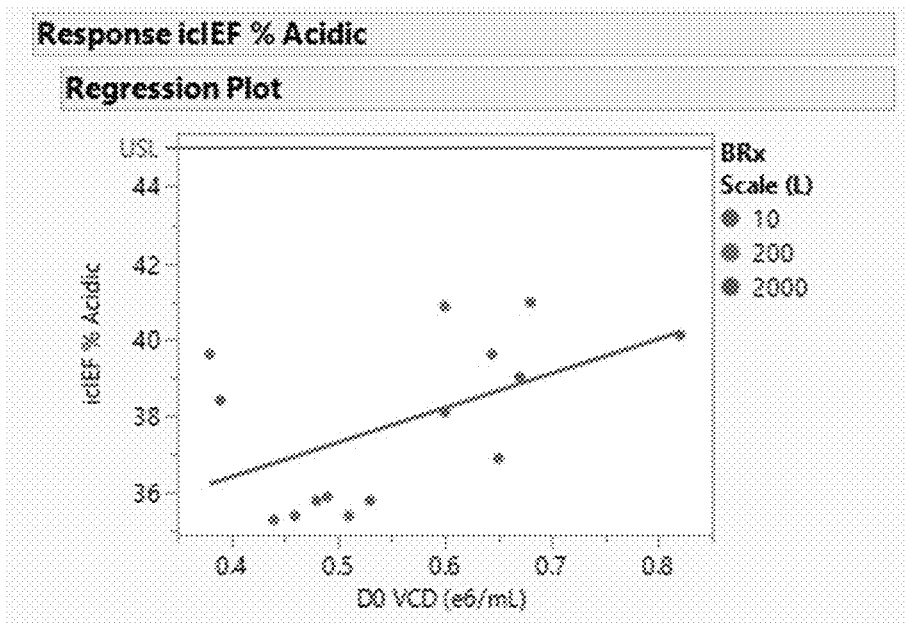

The effect of seeding density on charge variants was also evaluated. As shown in FIG. 15, higher seeding densities lead to higher acidic species.

Based on the data demonstrated in this example, it is clear that cell culture duration, seeding density, and end of culture viability play a pivotal role in shaping the charge heterogeneity of KPL-387. These parameters must be monitored closely and controlled to maximize yield (expression) and maintain product quality. Since acidic variants of KPL-387 can significantly affect the biological potency, stability, and potentially other quality attributes, controlling bioreactor parameters is critical for ensuring consistent product quality. While some degree of charge heterogeneity is inevitable and acceptable, specific process parameters must be developed and controlled for each therapeutic antibody program to account for unpredictable effects that charge heterogeneity may have on the antibody's critical quality attributes. Such efforts are necessary to ensure that the product quality is within defined limits from batch to batch, and understanding the mechanistic links between production process and functional outcomes is critical for modern biopharmaceutical development.

In conclusion, process controls have been established to preserve charge variant profile while balancing expression levels. These controls include a cell culture duration of no more than 16 days, when inoculated at a seeding density of $0.4\times10^6$ to $0.6\times10^6$ cells/mL, and a criterion to harvest if the cell viability is expected to be below 60% within 24 hours. Additionally, this process has shown to retain isoform levels within predefined ranges and isoforms levels do not shift with increasing production duration and decreasing viability.

The invention claimed is:

1. A method of reducing the level of acidic species of an anti-IL-1R1 antibody, or antigen-binding portion thereof, in a clarified harvest from a cell culture, wherein the anti-IL-1R1 antibody or antigen-binding portion thereof, comprises a heavy chain variable region comprising a CDR1 having an amino acid sequence of SEQ ID NO:1, a CDR2 having an amino acid sequence of SEQ ID NO:2, and a CDR3 having an amino acid sequence of SEQ ID NO:3, and a light chain variable region comprising a CDR1 having an amino acid sequence of SEQ ID NO:4, a CDR2 having an amino acid sequence of SEQ ID NO:5, and a CDR3 having an amino acid sequence of SEQ ID NO:6 with the amino acid sequence of SEQ ID NO:1, a CDR2 having the amino acid sequence of SEQ ID NO:2, and a CDR3 having the amino acid sequence of SEQ ID NO:3, and a light chain variable region comprising a CDR1 having the amino acid sequence of SEQ ID NO: 4, a CDR2 having the amino acid sequence of SEQ ID NO:5, and a CDR3 having the amino acid sequence of SEQ ID NO:6, the method comprising harvesting the cell culture when the viability decreases to no less than 50%, thereby reducing the level of acidic species of the anti-IL-1R1 antibody, or antigen-binding portion thereof, in the clarified harvest.

2. The method of claim 1, wherein the cell culture is harvested when the viability of the cell culture decreases to 55%-100%.

3. The method of claim 1, wherein the cell culture is harvested when the viability of the cell culture decreases to no less than 60%.

4. The method of claim 1, wherein the cell culture is harvested when the viability of the cell culture decreases to 60%.

5. The method of claim 1, further comprising inoculating the cell culture at a seeding density of $0.4 \times 10^6$ to $0.8 \times 10^6$ cells/mL.

6. The method of claim 5, wherein the seeding density of the cell culture is about $0.4 \times 10^6$ cells/mL.

7. The method of claim 1, further comprising incubating the cell culture in a bioreactor for no more than 20 days.

8. The method of claim 1, wherein the cell culture is incubated in the bioreactor for no more than 16 days.

9. The method of claim 1, further comprising maintaining the viability of the cell culture at a level of at least 50%.

10. The method of claim 9, wherein the viability of the cell culture is maintained at a level of 50%-100%.

11. The method of claim 1,
(a) wherein the clarified harvest comprises less than 55% acidic species of the antibody;
(b) wherein the clarified harvest comprises less than 15% basic species; and/or
(c) wherein the clarified harvest comprises more than 40% main species.

12. The method of claim 1,
(a) wherein the clarified harvest comprises 1-15% basic species of the antibody;
(b) wherein the clarified harvest comprises 40-70% main species of the antibody; and/or
(c) wherein the clarified harvest comprises 30-55% acidic species of the antibody.

13. The method of claim 1,
wherein the clarified harvest comprises 40-80% isoform B, 10-30% isoform A/B, and/or 10-30% isoform A of the antibody.

14. The method of claim 1,
wherein the anti-IL-1R1 antibody, or antigen-binding portion thereof, comprises a heavy chain variable region comprising the amino acid sequence of SEQ ID NO:7, and a light chain variable region comprising the amino acid sequence of SEQ ID NO:8.

15. The method of claim 1, wherein the cell culture is harvested when the viability of the cell culture decreases to 55%-65%.

16. The method of claim 1, further comprising inoculating the cell culture at a seeding density of $0.4 \times 10^6$ to $0.6 \times 10^6$ cells/mL.

17. The method of claim 1, further comprising inoculating the cell culture at a seeding density of $0.5 \times 10^6$ cells/mL.

18. The method of claim 1, further comprising inoculating the cell culture at a seeding density of $0.6 \times 10^6$ cells/mL.

19. The method of claim 1, further comprising incubating the cell culture in a bioreactor for 8 to 16 days.

20. The method of claim 12, wherein the clarified harvest comprises 30-55% acidic species, 1-15% basic species, and 40-70% main species.

21. The method of claim 12, wherein the clarified harvest comprises 30-40% acidic species, 1-5% basic species, and 55-70% main species.

22. The method of claim 12, wherein the clarified harvest comprises 34-36% acidic species, 1-5% basic species, and 60-63% main species.

23. The method of claim 1, wherein the clarified harvest comprises 50-75% isoform B, 15-25% isoform A/B, and/or 10-25% isoform A of the antibody.

24. The method of claim 1, wherein the clarified harvest comprises 45-60% isoform B, 20-30% isoform A/B, and/or 15-30% isoform A of the antibody.

25. The method of claim 1, wherein the anti-IL-1R1 antibody, or antigen-binding portion thereof, comprises a heavy chain comprising the amino acid sequence of SEQ ID NO:9, and a light chain comprising the amino acid sequence of SEQ ID NO: 10.

26. The method of claim 1, wherein the anti-IL-1R1 antibody, or antigen-binding portion thereof, is KPL-387.

27. The method of claim 1, further comprising maintaining the viability of the cell culture at a level of at least 60%.

28. The method of claim 9, wherein the viability of the cell culture is maintained at a level of 60%-100%.

*     *     *     *     *